US012748069B2

(12) United States Patent
Fernandez-Gomez et al.

(10) Patent No.: US 12,748,069 B2
(45) Date of Patent: Sep. 29, 2026

(54) ENCODING STATE CHANGE OF NANOPORE TO REDUCE DATA SIZE

(71) Applicant: Roche Sequencing Solutions, Inc., Pleasanton, CA (US)

(72) Inventors: Santiago Fernandez-Gomez, Sunnyvale, CA (US); Hui Tian, Cupertino, CA (US); Bill Maney, Emerald Hills, CA (US); Seung Shin, San Jose, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 161 days.

(21) Appl. No.: 18/904,910

(22) Filed: Oct. 2, 2024

(65) Prior Publication Data

US 2025/0102459 A1 Mar. 27, 2025

Related U.S. Application Data

(63) Continuation of application No. 17/248,610, filed on Jan. 29, 2021, now Pat. No. 12,135,306, which is a continuation of application No. 14/864,400, filed on Sep. 24, 2015, now Pat. No. 10,935,512.

(51) Int. Cl.
*G01N 27/40* (2006.01)
*G01N 33/487* (2006.01)

(52) U.S. Cl.
CPC ....... *G01N 27/40* (2013.01); *G01N 33/48721* (2013.01)

(58) Field of Classification Search
None
See application file for complete search history.

(56) References Cited

U.S. PATENT DOCUMENTS

| | | | |
|---|---|---|---|
| 8,290,714 B2 | 10/2012 | Ignatius et al. | |
| 10,102,338 B2 * | 10/2018 | Fernandez-Gomez ...................... | G01N 33/48721 |
| 10,935,512 B2 * | 3/2021 | Fernandez-Gomez ...................... | G01N 33/48721 |

(Continued)

FOREIGN PATENT DOCUMENTS

| | | |
|---|---|---|
| JP | 2009508086 A | 2/2009 |
| JP | 2011501806 A | 1/2011 |

(Continued)

OTHER PUBLICATIONS

Lichstein, et al., Studies of the Effect of Sodium Azide on Microbic Growth and Respiration, Journal of Bacteriology, 1944, 47(3), 221-230. (Year: 1944).

(Continued)

*Primary Examiner* — Eman A Alkafawi
*Assistant Examiner* — Suresh K Rajaputra
(74) *Attorney, Agent, or Firm* — Roche Sequencing Solutions, Inc.

(57) ABSTRACT

A system includes a circuit configured to detect a voltage corresponding to an electrical measurement of a nanopore. The system also includes a component configured to compare the voltage to another voltage. Based at least in part on the comparison, a one bit indicator is determined. The one bit indicator indicates whether the voltage indicates a change in a state of the nanopore. In the event it is determined that the voltage indicates the change in the state of the nanopore, a multiple bit signal is provided for output.

15 Claims, 37 Drawing Sheets

(56) References Cited

U.S. PATENT DOCUMENTS

| | | | |
|---|---|---|---|
| 12,135,306 | B2 * | 11/2024 | Fernandez-Gomez ...................... G01N 27/40 |
| 2005/0019784 | A1 | 1/2005 | Su et al. |
| 2006/0148104 | A1 | 7/2006 | Marini et al. |
| 2007/0108068 | A1 | 5/2007 | Suh et al. |
| 2008/0225327 | A1 | 9/2008 | Smith |
| 2009/0150084 | A1 | 6/2009 | Colwell et al. |
| 2010/0166006 | A1 | 7/2010 | Xu |
| 2010/0194469 | A1 | 8/2010 | Amrutur et al. |
| 2010/0301299 | A1 | 12/2010 | Suh et al. |
| 2012/0234679 | A1 | 9/2012 | Garaj |
| 2013/0256118 | A1 | 10/2013 | Meller et al. |
| 2013/0274148 | A1 | 10/2013 | Kain et al. |
| 2014/0037210 | A1 | 2/2014 | Depalov et al. |
| 2014/0154790 | A1 | 6/2014 | Ono et al. |
| 2014/0221249 | A1 | 8/2014 | Chen et al. |
| 2014/0242588 | A1 | 8/2014 | Van Den Boom et al. |
| 2014/0250286 | A1 | 9/2014 | Kondo et al. |
| 2014/0318966 | A1 | 10/2014 | Astier |
| 2014/0354443 | A1 | 12/2014 | Roberson et al. |
| 2015/0107996 | A1 | 4/2015 | Chen |
| 2015/0119259 | A1 | 4/2015 | Ju et al. |
| 2015/0344945 | A1 | 12/2015 | Mandell et al. |
| 2016/0123923 | A1 * | 5/2016 | Chen .................... C12Q 1/6869 204/603 |

FOREIGN PATENT DOCUMENTS

| | | | |
|---|---|---|---|
| JP | 2013-519088 | A | 5/2013 |
| JP | 2015510129 | A | 4/2015 |
| WO | 2006133084 | A2 | 12/2006 |
| WO | 2009045472 | A1 | 4/2009 |
| WO | 2011067559 | A1 | 6/2011 |
| WO | 2011097028 | A1 | 8/2011 |
| WO | 2012164679 | A1 | 12/2012 |
| WO | 2013/123450 | A1 | 8/2013 |
| WO | 2013130635 | A2 | 9/2013 |
| WO | 2014123716 | A1 | 8/2014 |
| WO | 2015057324 | A2 | 4/2015 |

OTHER PUBLICATIONS

Vogelstein et al, Digital PCR, Proceedings of the National Academy of Science USA, Aug. 1999, pp. 9236-9241, vol. 96.

* cited by examiner

```
* WE=Electroplated Pd, 24uL, 500mM KAc, 10mM KCl, CE=AgCl Can
* bilayerpop_gentle, getpore_acetate2 (deactivation at 15pA)
* 011_
JP_P24_1165_SCW2R12C24_130212_Exp0073I
V0 1 0 PULSE(0 0.2 0 500us 500us 99.5ms 200ms)
C0 2 1 300e12
R0 3 2 100e6
* C2 3 0 100e15
S1 3 4 3 0 switch1 ON
.model switch1 sw vt=0 vh=0 ron=1e3 roff=1e12
B1 4 0 I = 0.3 * ( 8.829e10*
v(4)^2 + 8.9292e10*
v(4) )
S2 3 5 0 3 switch2 ON
.model switch2 sw vt=0 vh=0 ron=1e3 roff=1e12
B2 5 0 I = 0.3 * ( 1.2232e9*
v(5)^2 + 8.3668e10*
v(5) )
.END
.tran 50us 27s
```

FIG. 11

ENCODING STATE CHANGE OF NANOPORE TO REDUCE DATA SIZE

CROSS REFERENCE TO RELATED APPLICATIONS

This application is a continuation of U.S. patent application Ser. No. 17/248,610, filed Jan. 29, 2021, entitled ENCODING STATE CHANGE OF NANOPORE TO REDUCE DATA SIZE, which is a continuation of U.S. patent application Ser. No. 14/864,400, filed Sep. 24, 2015, each of which is herein incorporated by reference in its entirety.

BACKGROUND OF THE INVENTION

Advances in micro-miniaturization within the semiconductor industry in recent years have enabled biotechnologists to begin packing traditionally bulky sensing tools into smaller and smaller form factors, onto so-called biochips. Often the amount of data that can be exported out of the biochip is constrained due to limitations in communication bandwidth. As more and more information is generated by the biochip, it would be desirable to reduce the amount of data needed to be exported out of the biochip.

BRIEF DESCRIPTION OF THE DRAWINGS

Various embodiments of the invention are disclosed in the following detailed description and the accompanying drawings.

FIG. 11 illustrates an embodiment of a simulation model that was matched to the data of FIG. 10.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Nanopore membrane devices having pore sizes on the order of one nanometer in internal diameter have shown promise in rapid nucleotide sequencing. When a voltage potential is applied across a nanopore immersed in a conducting fluid, a small ion current attributed to the conduction of ions across the nanopore can be observed. The size of the current is sensitive to the pore size.

A nanopore-based sequencing chip may be used for DNA sequencing. A nanopore-based sequencing chip incorporates a large number of sensor cells configured as an array. For example, an array of one million cells may include 1000 rows by 1000 columns of cells.

Figure 1:
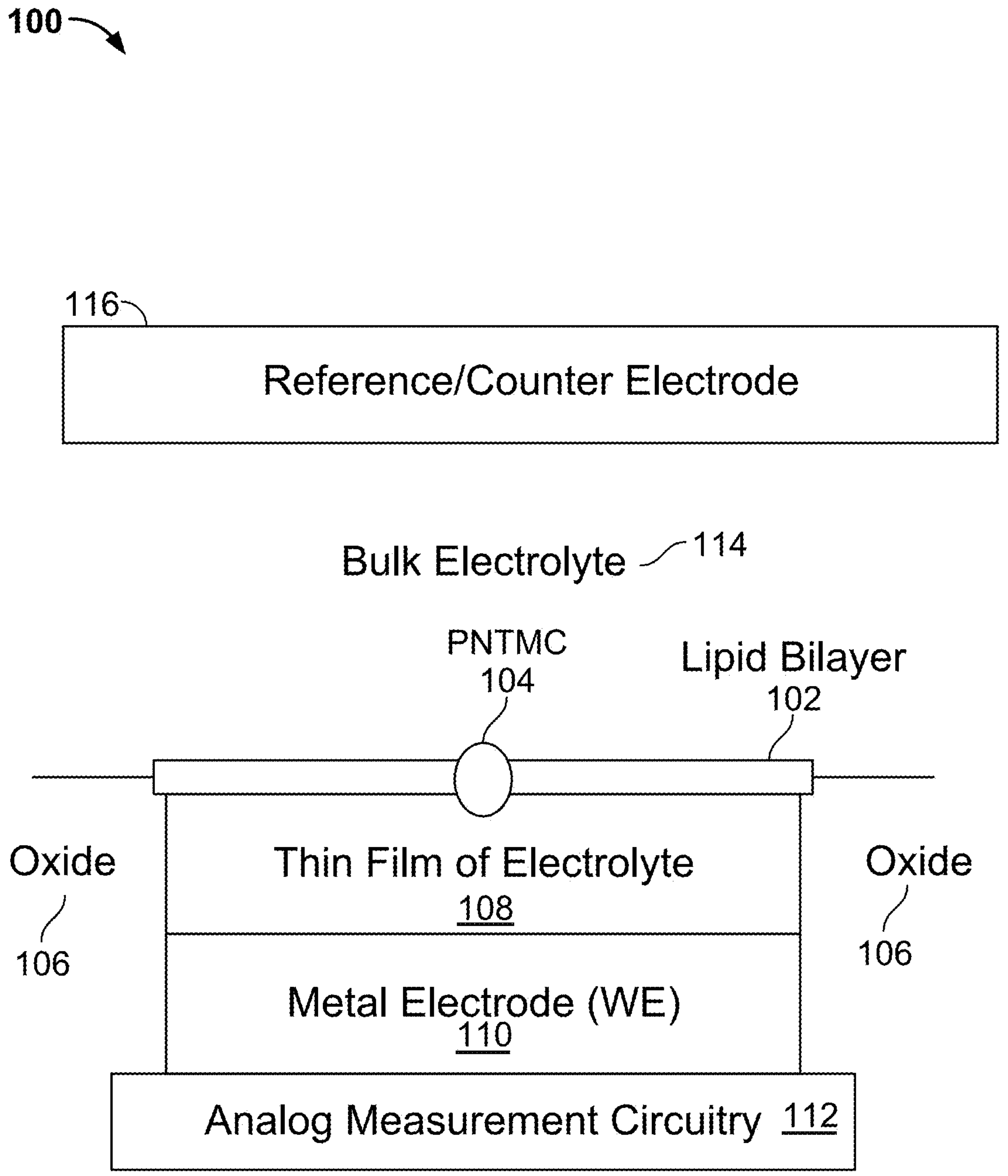
FIG. 1 illustrates an embodiment of a cell 100 in a nanopore-based sequencing chip.

FIG. 1 illustrates an embodiment of a cell 100 in a nanopore-based sequencing chip. A membrane 102 is formed over the surface of the cell. In some embodiments, membrane 102 is a lipid bilayer. The bulk electrolyte 114 containing soluble protein nanopore transmembrane molecular complexes (PNTMC) and the analyte of interest is placed directly onto the surface of the cell. A single PNTMC 104 is inserted into membrane 102 by electroporation. The individual membranes in the array are neither chemically nor electrically connected to each other. Thus, each cell in the array is an independent sequencing machine, producing data unique to the single polymer molecule associated with the PNTMC. PNTMC 104 operates on the analytes and modulates the ionic current through the otherwise impermeable bilayer.

With continued reference to FIG. 1, analog measurement circuitry 112 is connected to a metal electrode 110 covered by a thin film of electrolyte 108. The thin film of electrolyte 108 is isolated from the bulk electrolyte 114 by the ion-impermeable membrane 102. PNTMC 104 crosses membrane 102 and provides the only path for ionic current to flow from the bulk liquid to working electrode 110. The cell also includes a counter electrode (CE) 116, which is an electrochemical potential sensor.

Figure 2:
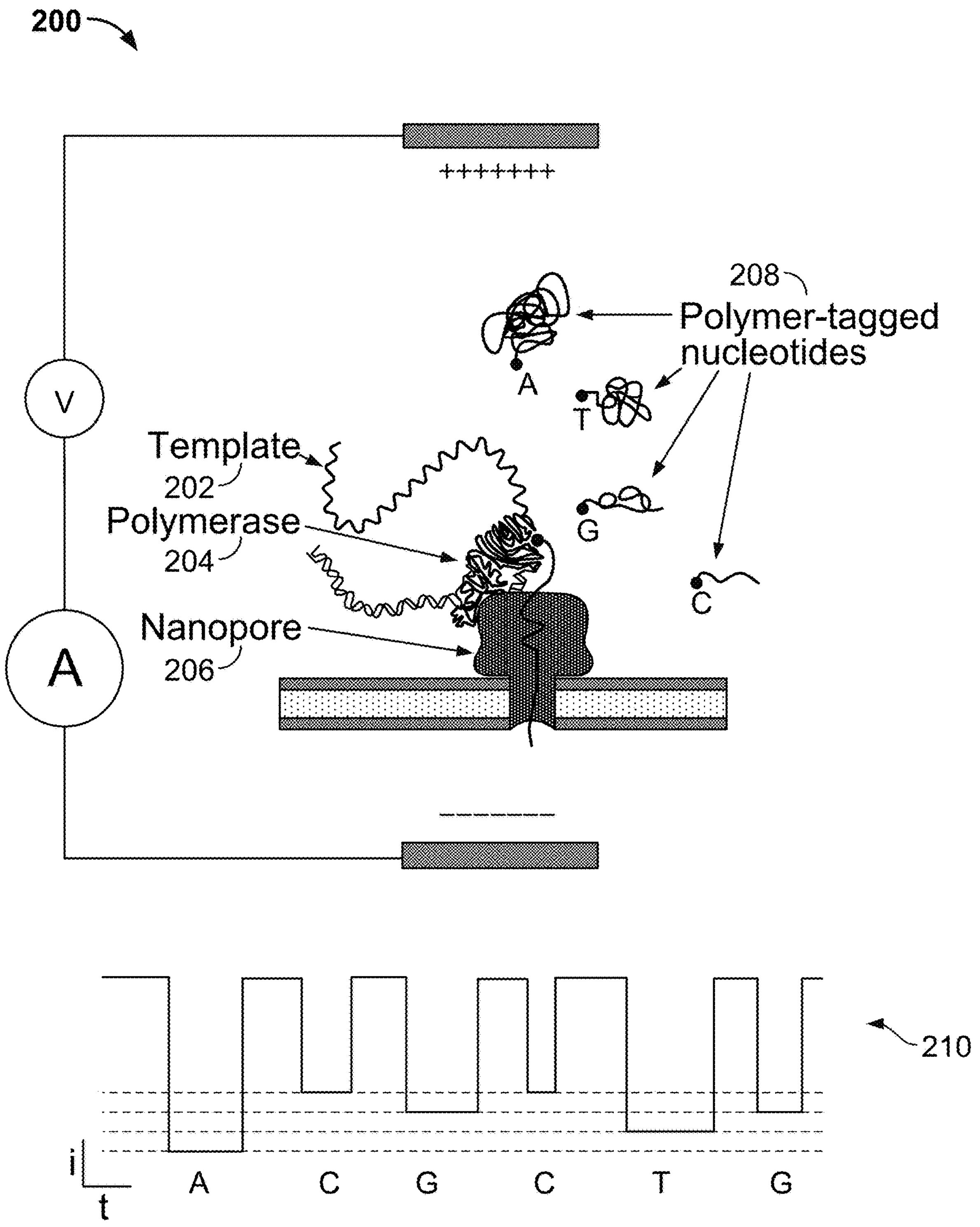
FIG. 2 illustrates an embodiment of a cell 200 performing nucleotide sequencing with the Nano-SBS technique.

In some embodiments, a nanopore array enables parallel sequencing using the single molecule nanopore-based sequencing by synthesis (Nano-SBS) technique. FIG. 2 illustrates an embodiment of a cell 200 performing nucleotide sequencing with the Nano-SBS technique. In the Nano-SBS technique, a template 202 to be sequenced and a primer are introduced to cell 200. To this template-primer complex, four differently tagged nucleotides 208 are added to the bulk aqueous phase. As the correctly tagged nucleotide is complexed with the polymerase 204, the tail of the tag is positioned in the barrel of nanopore 206. The tag held in the barrel of nanopore 206 generates a unique ionic blockade signal 210, thereby electronically identifying the added base due to the tags' distinct chemical structures.

Figure 3:
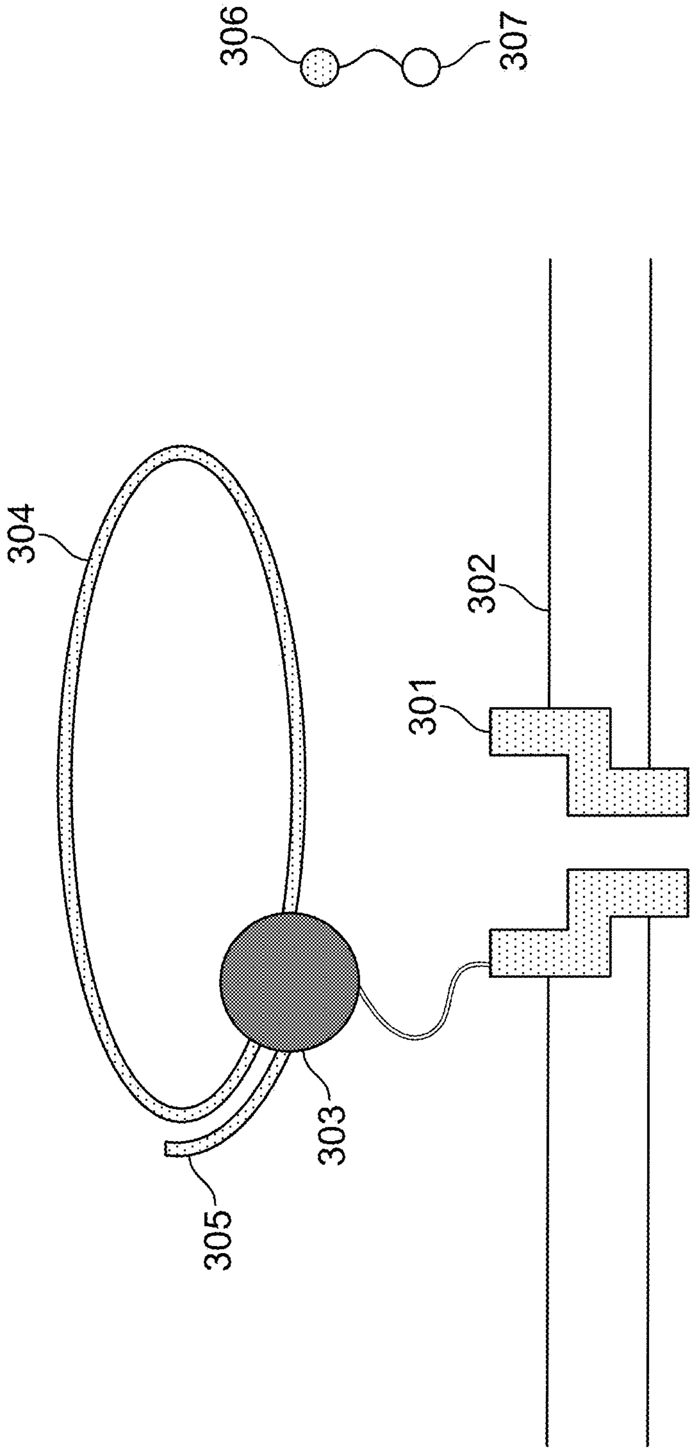
FIG. 3 illustrates an embodiment of a cell about to perform nucleotide sequencing with pre-loaded tags.

FIG. 3 illustrates an embodiment of a cell about to perform nucleotide sequencing with pre-loaded tags. A nanopore 301 is formed in a membrane 302. An enzyme 303 (e.g., a polymerase, such as a DNA polymerase) is associated with the nanopore. In some cases, polymerase 303 is covalently attached to nanopore 301. Polymerase 303 is associated with a nucleic acid molecule 304 to be sequenced. In some embodiments, the nucleic acid molecule 304 is circular. In some cases, nucleic acid molecule 304 is linear. In some embodiments, a nucleic acid primer 305 is hybridized to a portion of nucleic acid molecule 304. Polymerase 303 catalyzes the incorporation of nucleotides 306 onto primer 305 using single stranded nucleic acid molecule 304 as a template. Nucleotides 306 comprise tag species ("tags") 307.

Figure 4:
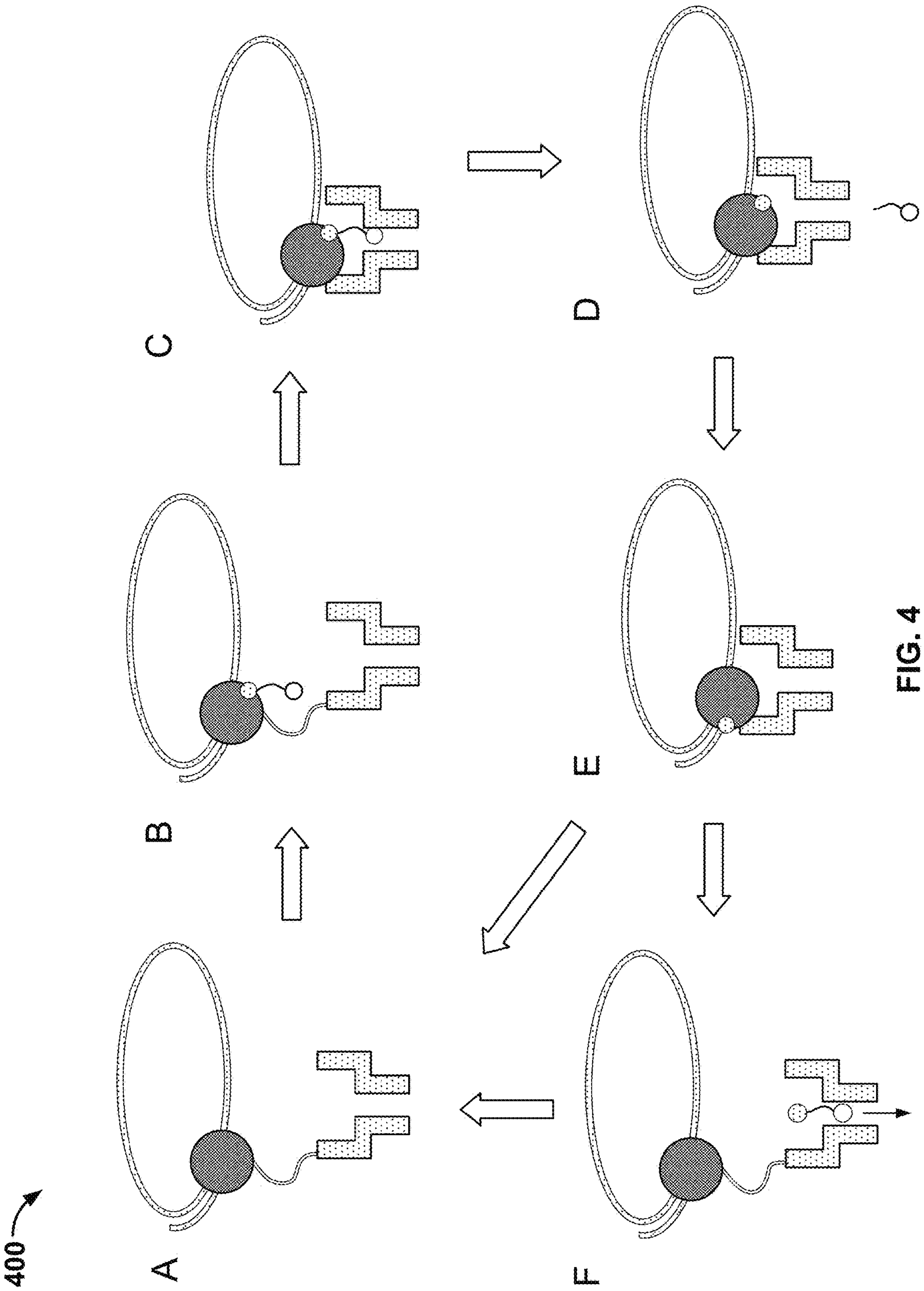
FIG. 4 illustrates an embodiment of a process 400 for nucleic acid sequencing with pre-loaded tags.

FIG. 4 illustrates an embodiment of a process 400 for nucleic acid sequencing with pre-loaded tags. Stage A illustrates the components as described in FIG. 3. Stage C shows the tag loaded into the nanopore. A "loaded" tag may be one that is positioned in and/or remains in or near the nanopore for an appreciable amount of time, e.g., 0.1 millisecond (ms) to 10000 ms. In some cases, a tag that is pre-loaded is loaded in the nanopore prior to being released from the nucleotide. In some instances, a tag is pre-loaded if the probability of the tag passing through (and/or being detected by) the nanopore after being released upon a nucleotide incorporation event is suitably high, e.g., 90% to 99%.

At stage A, a tagged nucleotide (one of four different types: A, T, G, or C) is not associated with the polymerase. At stage B, a tagged nucleotide is associated with the polymerase. At stage C, the polymerase is docked to the nanopore. The tag is pulled into the nanopore during docking by an electrical force, such as a force generated in the presence of an electric field generated by a voltage applied across the membrane and/or the nanopore.

Some of the associated tagged nucleotides are not base paired with the nucleic acid molecule. These non-paired nucleotides typically are rejected by the polymerase within a time scale that is shorter than the time scale for which correctly paired nucleotides remain associated with the polymerase. Since the non-paired nucleotides are only transiently associated with the polymerase, process 400 as shown in FIG. 4 typically does not proceed beyond stage D. For example, a non-paired nucleotide is rejected by the polymerase at stage B or shortly after the process enters stage C.

Before the polymerase is docked to the nanopore, the conductance of the nanopore is ~300 pico Siemens (300 pS). At stage C, the conductance of the nanopore is about 60 pS, 80 pS, 100 pS, or 120 pS corresponding to one of the four types of tagged nucleotides. The polymerase undergoes an isomerization and a transphosphorylation reaction to incorporate the nucleotide into the growing nucleic acid molecule and release the tag molecule. In particular, as the tag is held in the nanopore, a unique conductance signal (e.g., see signal 210 in FIG. 2) is generated due to the tag's distinct chemical structures, thereby identifying the added base electronically. Repeating the cycle (i.e., stage A through E or stage A through F) allows for the sequencing of the nucleic acid molecule. At stage D, the released tag passes through the nanopore.

In some cases, tagged nucleotides that are not incorporated into the growing nucleic acid molecule will also pass through the nanopore, as seen in stage F of FIG. 4. The unincorporated nucleotide can be detected by the nanopore in some instances, but the method provides a means for distinguishing between an incorporated nucleotide and an unincorporated nucleotide based at least in part on the time for which the nucleotide is detected in the nanopore. Tags bound to unincorporated nucleotides pass through the nanopore quickly and are detected for a short period of time (e.g., less than 10 ms), while tags bound to incorporated nucleotides are loaded into the nanopore and detected for a long period of time (e.g., at least 10 ms).

Two types of ionic flow can be driven through the PNTMC-faradaic conduction and non-faradaic conduction. In faradaic conduction, a chemical reaction occurs at the surface of the metal electrode. The faradaic current is the current generated by the reduction or oxidation of some chemical substances at an electrode. In non-faradaic conduction, no chemical reaction happens at the surface of the metal. The changing potential on the double layer capacitance between the metal electrode and the thin film of electrolyte drives the ion flow.

Ionic flow by faradaic conduction has a number of drawbacks. The operational lifespan of an electrode is limited because the metal in the electrode is consumed and depleted as the ionic current flows through the PNTMC, as will be described in greater detail below.

Figure 5B:
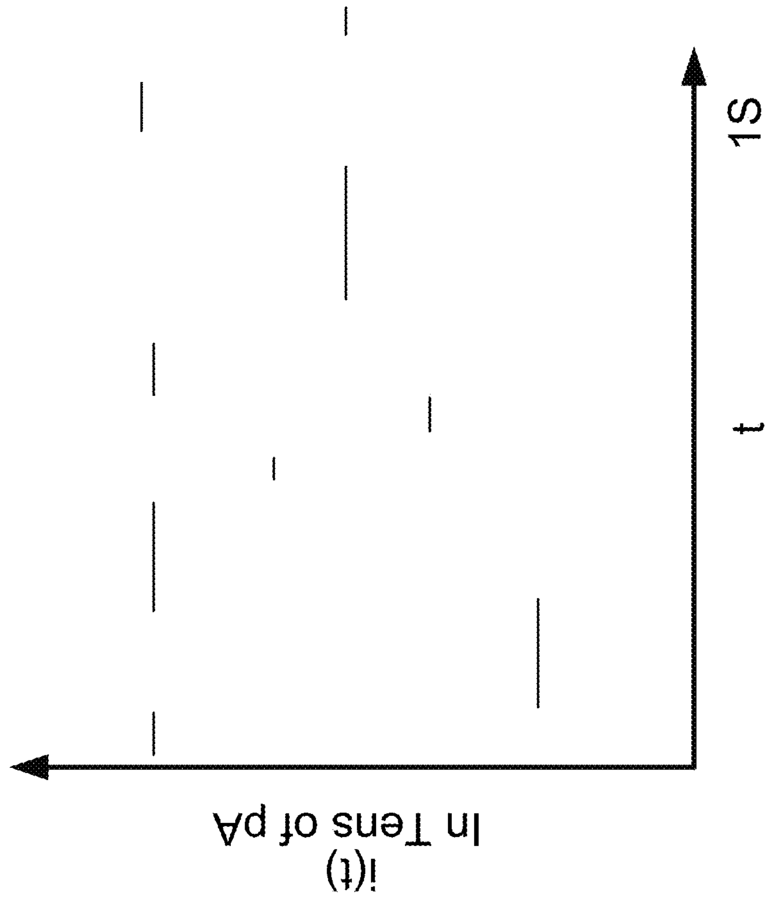
FIG. 5B illustrates the different states of the PNTMC with faradaic conduction.
Figure 5A:
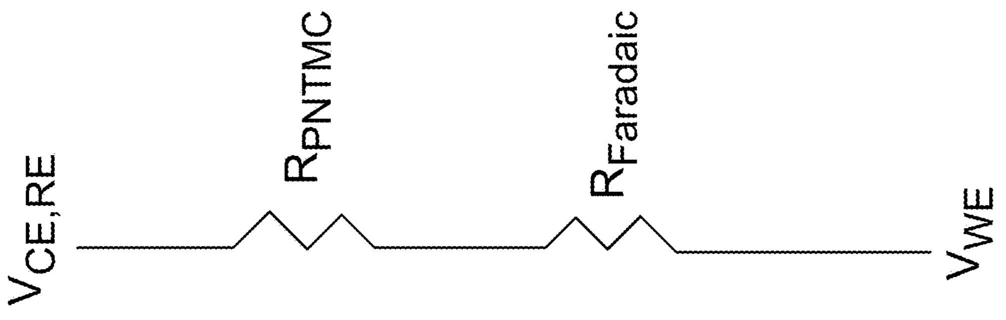
FIG. 5A illustrates an embodiment of a small signal circuit model during faradaic conduction.

FIG. 5A illustrates an embodiment of a small signal circuit model during faradaic conduction. The PNTMC and WE are represented as simple resistors in the small signal circuit model. FIG. 5B illustrates the different states of the PNTMC with faradaic conduction. The ionic current flow, i(t), has five states: the highest current state with an open nanopore channel (not shown) and four lower current states corresponding to each of four different types of nucleotides bound to the active site of the PNTMC. Positive current flow i(t) describes electrons entering the $V_{CE, RE}$ node and leaving the $V_{WE}$ node. Anions (e.g., $Cl^-$) leave the CE, flow through the bulk electrolyte, cross the lipid bilayer via the PNTMC, and continue through the thin film of electrolyte and combine with the metal of the WE.

For example, for an electrode with silver metal (Ag), the chemical reaction is:

$$Ag_{(solid)} + Cl^-_{(aqueous)} \rightarrow AgCl_{(solid)} + electron_{(flows\ in\ analog\ circuit)} \quad \text{Equation 1}$$

As shown in Equation 1 above, an atom of metallic silver is converted to an insoluble salt, silver-chloride (AgCl), for each chloride anion ($Cl^-$) that passes through the PNTMC. In some cases, the silver is depleted within minutes of operation.

To avoid depletion of the metal electrode, the direction of the ionic current flow may be reversed by applying a negative voltage for a similar duration, causing the silver-chloride (AgCl) to be converted back to silver metal. However, recharging or refreshing in this manner causes the silver to be re-deposited as hair-like features on the surface of the metal electrode, which may impact overall performance, especially in chips with smaller cell geometry and thus smaller electrodes.

Another way is to delay the depletion of the metal electrode by applying a voltage to draw the polymerase to the nanopore and pull the tag through or to the proximity of the nanopore for detection, and then turn off the voltage for a period of time, which will cause the tag to be released from the nanopore. Since there is no current while the voltage is turned off, fewer silver atoms are converted and the lifespan of the metal electrode is prolonged. However, the detection time is reduced accordingly.

In addition to depletion of the metal electrode, faradaic conduction also causes an imbalance in the concentration of the bulk electrolyte within the cells over time. For example, there is a net gain of KCl molecules at one electrode but a net loss of KCl molecules at the opposite electrode. This salt concentration buildup at one electrode and salt depletion on the opposite electrode creates undesirable osmotic pressure within the cell.

An alternative type of ionic flow through the PNTMC is via non-faradaic conduction. In non-faradaic conduction, no chemical reaction (reduction or oxidation of chemical substances) occurs at the surface of the metal. The changing potential across the double layer capacitance between the metal electrode and the thin film of electrolyte drives the ion flow.

For non-faradaic conduction, the metal electrode may be made of metals that are resistant to corrosion and oxidation. For example, noble metals such as platinum or gold oxidize with difficulty, and even when they do oxidize, the process is easily reversible. When small potentials (e.g., less than +/−1 V relative to $V_{CE}$) are applied to platinum/gold in an electrolyte, aside from an initial capacitive transient, no ionic current flows. This allows the measurement of electron tunneling from the metal into redox (reduction-oxidation) active species mixed into the electrolyte. Without redox active species (such as Ferricyanide or Ferrocyanide) in the electrolyte, no steady state ionic (or electron or hole) current flows across the metal-liquid interface. Despite the lack of chemical (i.e., bonding) interaction between the platinum/gold and the electrolyte, there is transient physical displacement of ions in the electrolyte from the growth and shrinkage of the ion depletion region at the metal-liquid interface, in response to the applied potential. This ion depletion region is referred to as a "double layer" in electrochemistry parlance. Using an electrical engineering model, a parallel plate capacitor forms where the metal is one plate, the depletion region is the dielectric, and the diffuse distribution of ions in the liquid is the other plate.

Figure 6:
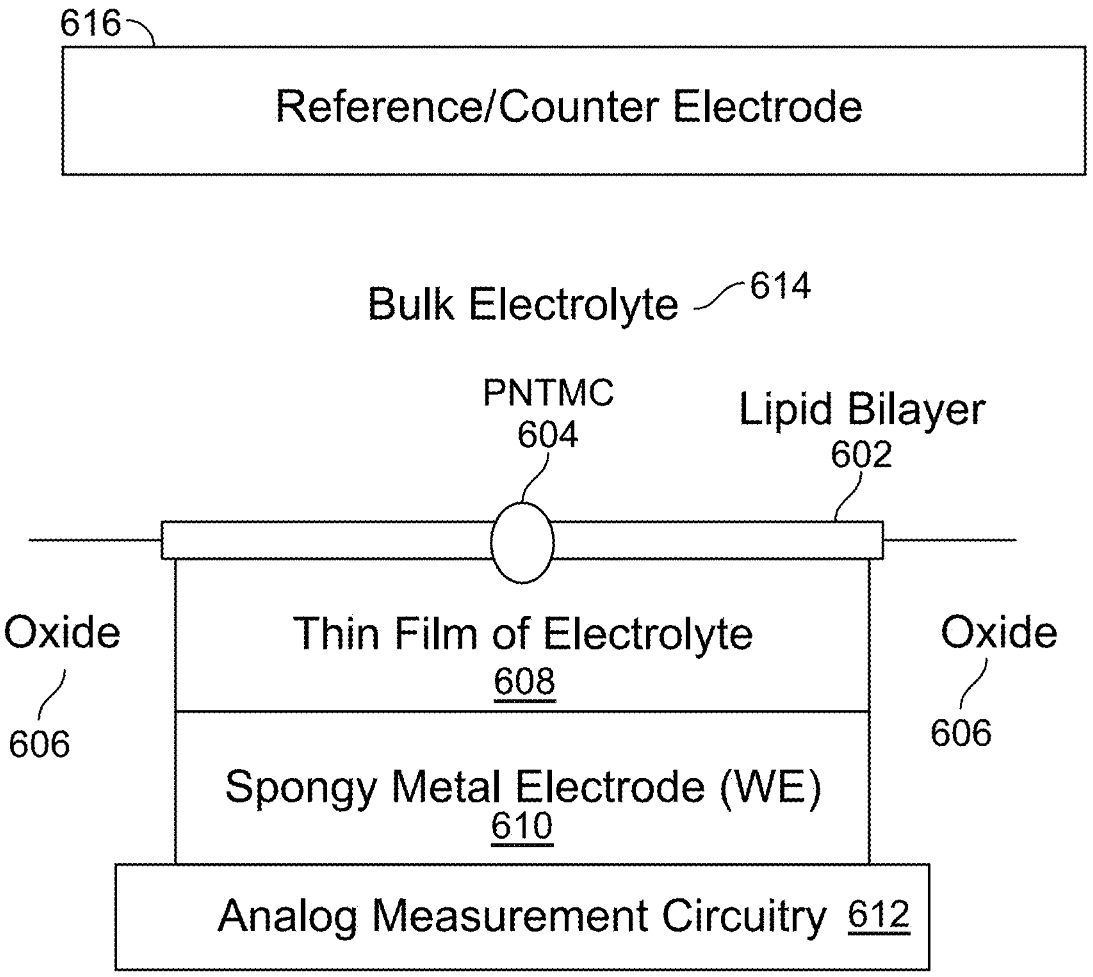
FIG. 6 illustrates an embodiment of a cell in a nanopore-based sequencing chip configured for non-faradaic and capacitively coupled measurements.

FIG. 6 illustrates an embodiment of a cell in a nanopore-based sequencing chip configured for non-faradaic and capacitively coupled measurements. A lipid bilayer 602 is formed over the surface of the cell. The electrolyte containing soluble protein nanopore transmembrane molecular complexes (PNTMC) and analyte of interest 614 is placed directly onto the surface of the cell. A single PNTMC 604 is inserted into lipid bilayer 602 by electroporation. The individual lipid bilayers in the array are not connected to each other either chemically or electrically. Thus, each cell in the array is an independent sequencing machine producing data unique to the single polymer molecule associated with the PNTMC. The cell includes an analog measurement circuit 612 for making non-faradaic and capacitively coupled measurements. The measurements are converted to digital information and transmitted out of the cell. In some embodiments, the transmission data rate is on the order of gigabits per second. In some embodiments, a field programmable gate array (FPGA) or an application-specific integrated circuit (ASIC) receives the transmitted data, processes the data, and forwards the data to a computer.

With continued reference to FIG. 6, analog measurement circuitry 612 is connected to a metal electrode 610 covered by a thin film of electrolyte 608. The thin film of electrolyte 608 is isolated from the bulk electrolyte 614 by the ion-impermeable lipid bilayer 602. PNTMC 604 crosses lipid bilayer 602 and provides the only path for ionic flow from the bulk liquid to metal electrode 610. Metal electrode 610 is also referred to as the working electrode (WE). For non-faradaic conduction, metal electrode 610 may be made of metals that are resistant to corrosion and oxidation, e.g., platinum, gold, and graphite. Metal electrode 610 may be a spongy electrode, as will be described in greater detail below. The cell also includes a counter/reference electrode (CE/RE) 616, which is an electrochemical potential sensor.

Figure 7:
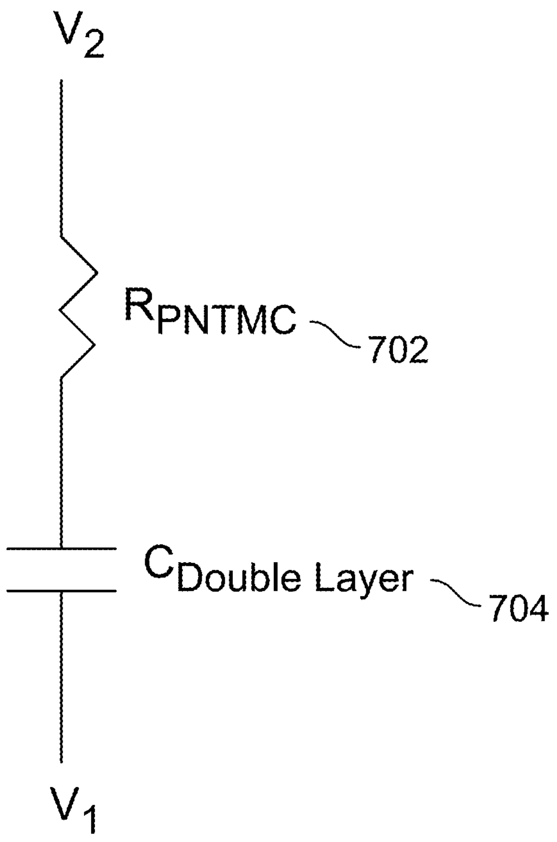
FIG. 7 illustrates an embodiment of a small signal circuit model for non-faradaic conduction.

FIG. 7 illustrates an embodiment of a small signal circuit model for non-faradaic conduction. The PNTMC is represented as a simple resistor 702 in the small signal circuit model. The double layer capacitance is represented as a capacitor 704 in the small signal circuit model. In some embodiments, $V_1$ in FIG. 7 is set to be an incremental voltage from ground, e.g., 500 mV, while $V_2$ is set to be $V_1$ plus an applied signal, e.g., an applied AC signal from 10 Hz to 1 kHz.

In some embodiments, the applied signal is an AC signal. At one polarity, the applied AC signal draws the polymerase to the nanopore and draws the tag through or to the proximity of the nanopore for detection. When the polarity of the applied AC signal is reversed, the tag is released from the nanopore, and the electrode is recharged/refreshed such that no electrochemical changes are made to the metal electrodes. As the AC signal repeatedly changes polarity, a portion of a tag associated with a tagged nucleotide is directed into a nanopore and directed out of the nanopore for a plurality of times. This repetitive loading and expulsion of a single tag allows the tag to be read multiple times. Multiple reads may enable correction for errors, such as errors associated with tags threading into and/or out of a nanopore.

In some embodiments, the frequency of the AC signal is chosen at least in part based on the time period during which a tagged nucleotide is associated with a polymerase. The frequency of the AC signal should allow a tagged nucleotide associated with the polymerase to be drawn and loaded into the nanopore for a sufficient length of time at least once such that the tag can be detected; otherwise, some of the tags that are associated with the polymerase cannot be detected by the system. In other words, the sampling should be at a rate faster than the rate at which the sequence of events is occurring, such that no events are missed.

Figure 8A:
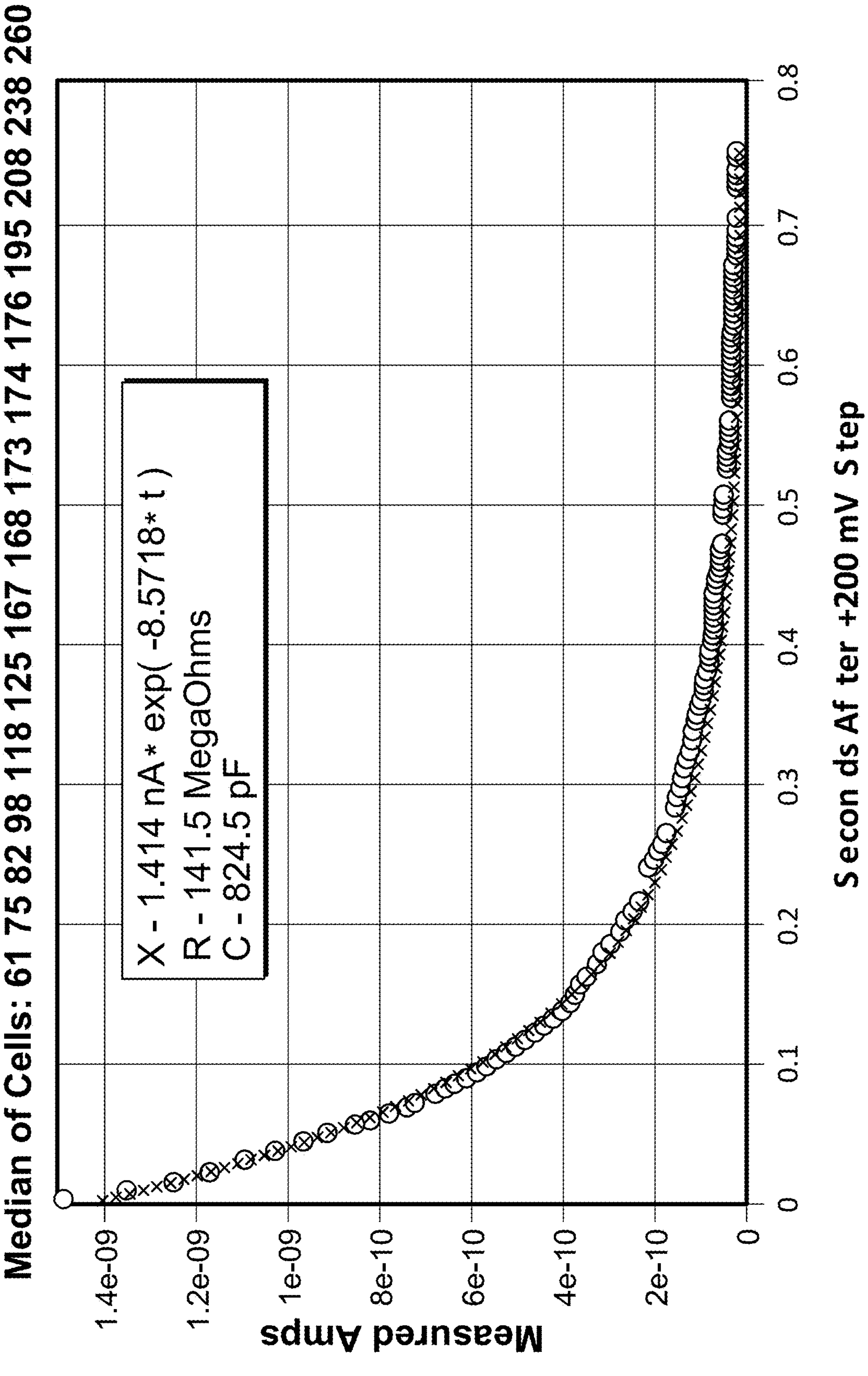
FIG. 8A and FIG. 8B illustrate an embodiment of the capacitive response of the double layer.
Figure 8B:
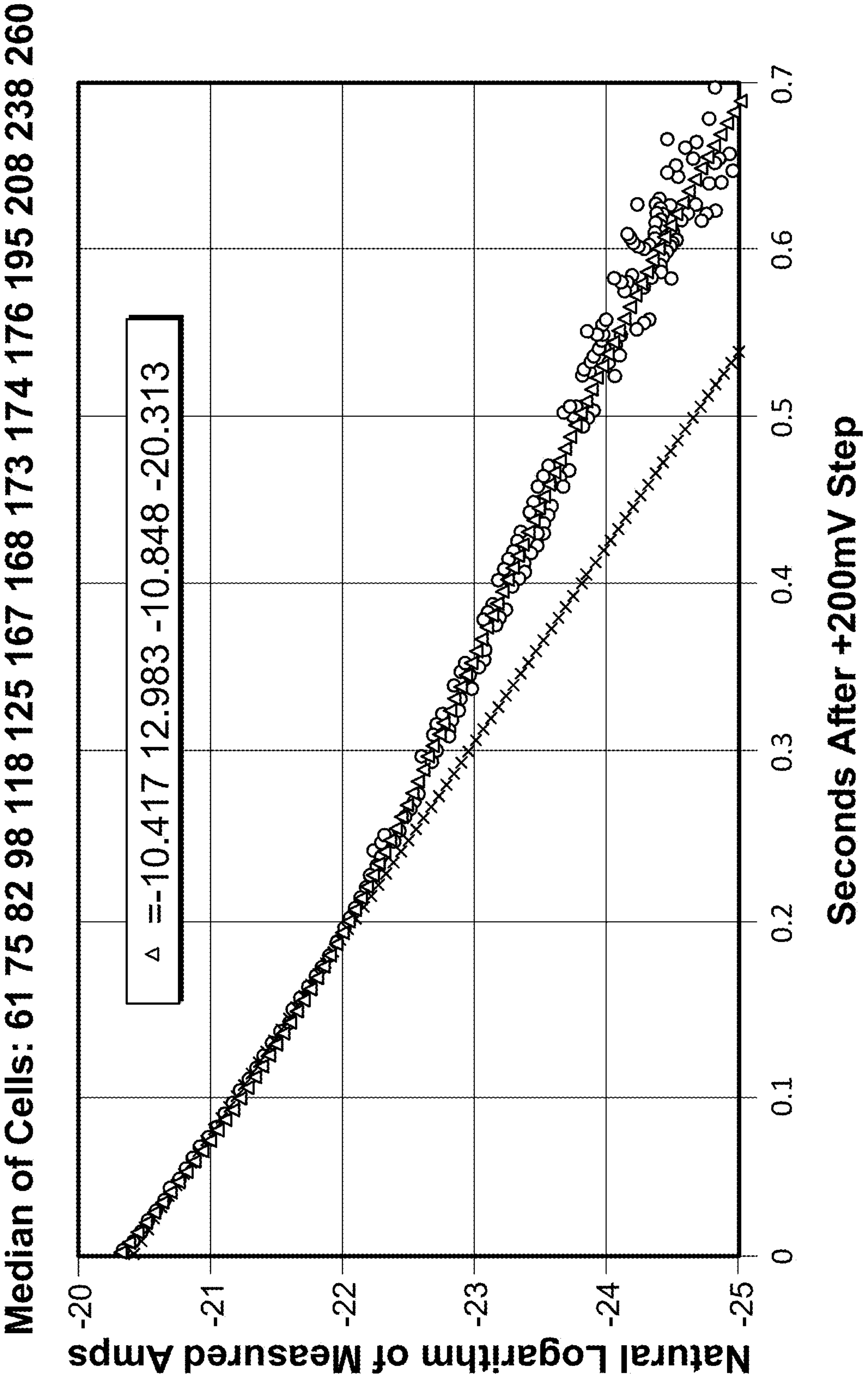

With continued reference to FIG. 6, before the lipid bilayer 602 has been formed, the bulk electrolyte 614 is in direct contact with the working electrode 610, thus creating a short circuit between the electrolyte and the working electrode. FIG. 8A and FIG. 8B illustrate an embodiment of the capacitive response of the double layer. The figures illustrate the properties of the double layer with a short circuit between the electrolyte and the working electrode. In this example, the electrolyte contains 0.5 M Potassium Acetate and 10 mM KCl. The counter electrode 616 includes AgCl. The working electrode 610 is a platinum electrode with electroplated platinum. Water viscosity prevents the easy flow of ions in response to the applied field; this is manifested as a series resistance in the double layer capacitive response. This resistance limits the peak current as shown in FIG. 8A. The series nature of the RC electrochemical connection can be seen in the decay of the response, which is characterized by the RC time constant. In FIG. 8B, the current is shown to fall to exp (−25)=13.8 pA, below the detection limit of the system. This demonstrates a lack of both shunt resistance (from an electrical point of view) and faradaic current (from an electrochemical point of view).

The working electrode 610 is configured to maximize its surface area for a given volume. As the surface area increases, the capacitance of the double layer increases, and a greater amount of ions can be displaced with the same applied potential before the capacitor becomes charged. Referring to FIG. 7, the impedance of $$C_{Double\ Layer} = \frac{1}{(j*2*\text{pi}*f*C)},$$

where f=frequency and $C=C_{Double\ Layer}$ By making f, C, or both f and C larger, the capacitor's impedance becomes very small relative to $R_{PNTMC}$, and the current to be measured becomes larger. As the impedance of the small signal model is dominated by $R_{PNTMC}$, the measured current can better differentiate the five states: the highest current state with an open nanopore channel and four lower current states corresponding to each of four different types of nucleotides bound into the active site of the PNTMC.

For example, the surface area of the working electrode may be increased by making the electrode "spongy." In some embodiments, the capacitance of the double layer to the bulk liquid can be enhanced by electroplating platinum metal onto a 5 micron diameter smooth platinum electrode in the presence of a detergent. The detergent creates nanoscale interstitial spaces in the platinum metal, making it "spongy." The platinum sponge soaks up electrolyte and creates a large effective surface area (e.g., 33 pF per square micron of electrode top-down area). Maximizing the double layer surface area creates a "DC block" capacitor, whereby the voltage on the double layer reaches steady state and barely changes during operation. The series PNTMC resistance ($R_{PNTMC}$ in FIG. 7) and the double layer capacitance ($C_{Double\ Layer}$ in FIG. 7) form a low frequency zero, which acts as a high pass filter. In one example, $R_{PNTMC}$~10 gigaohm, $C_{Double\ Layer}$~800 pF, resulting in a time constant of ~10 gigaohm*~800 pF=~8 second. Chopping the measurement at 100 Hz then rejects DC drift and attenuates low frequency information content in the measured tags by a factor of 1000.

Without any tags present, the PNTMC behaves similar to an alpha hemolysin protein nanopore. The hemolysin nanopore has a rectifying characteristic which changes its bias depending on the duty cycle of the square wave drive. Unlike the faradaic conduction case, the absolute voltage applied to the electrode is not the same as the voltage applied to the nanopore: the voltage on the double layer biases the potential applied to the nanopore, and this bias changes with the duty cycle.

Figure 9A:
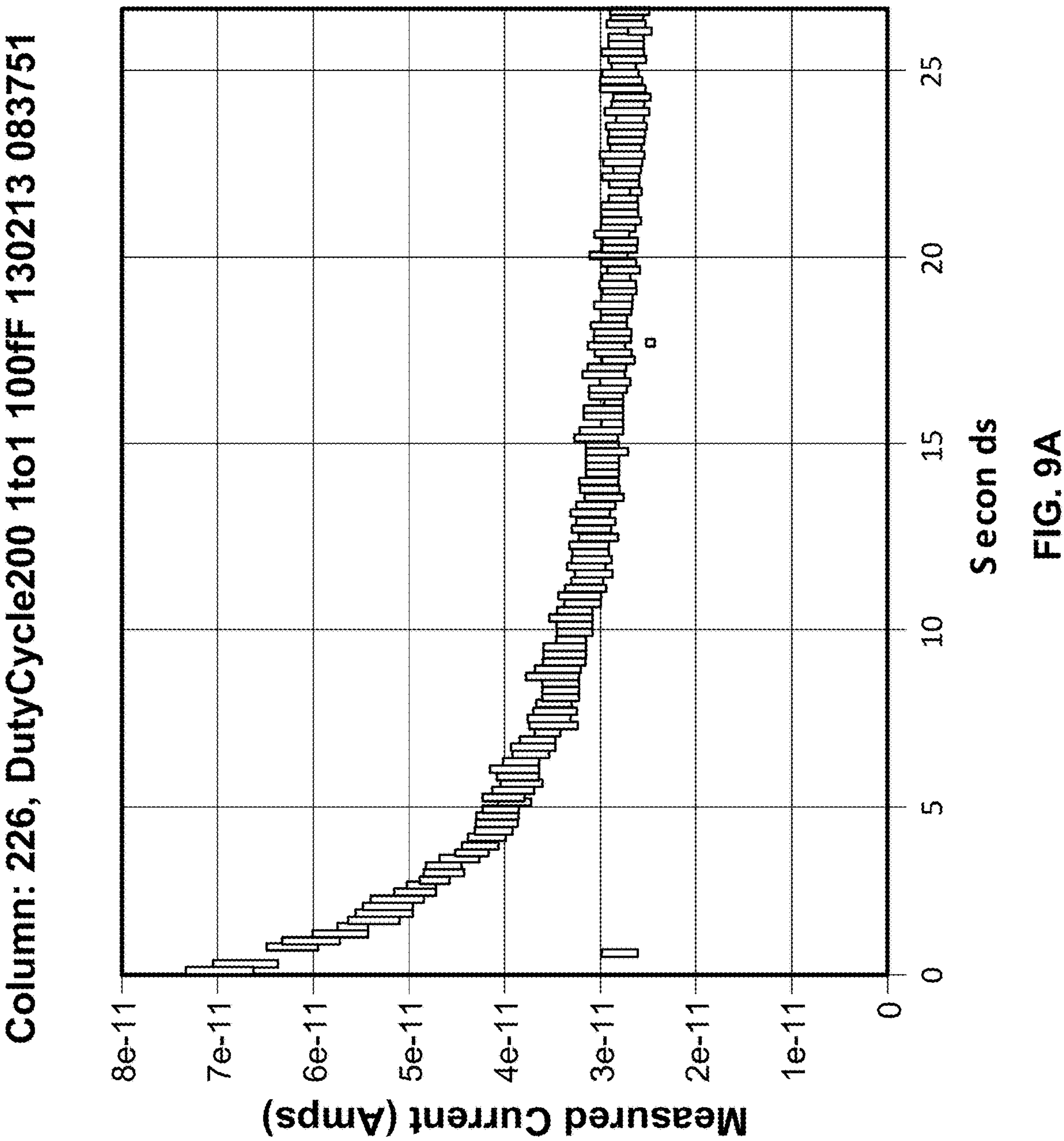
FIGS. 9A and 9B illustrate the nanopore current with non-faradaic AC modulation.
Figure 9B:
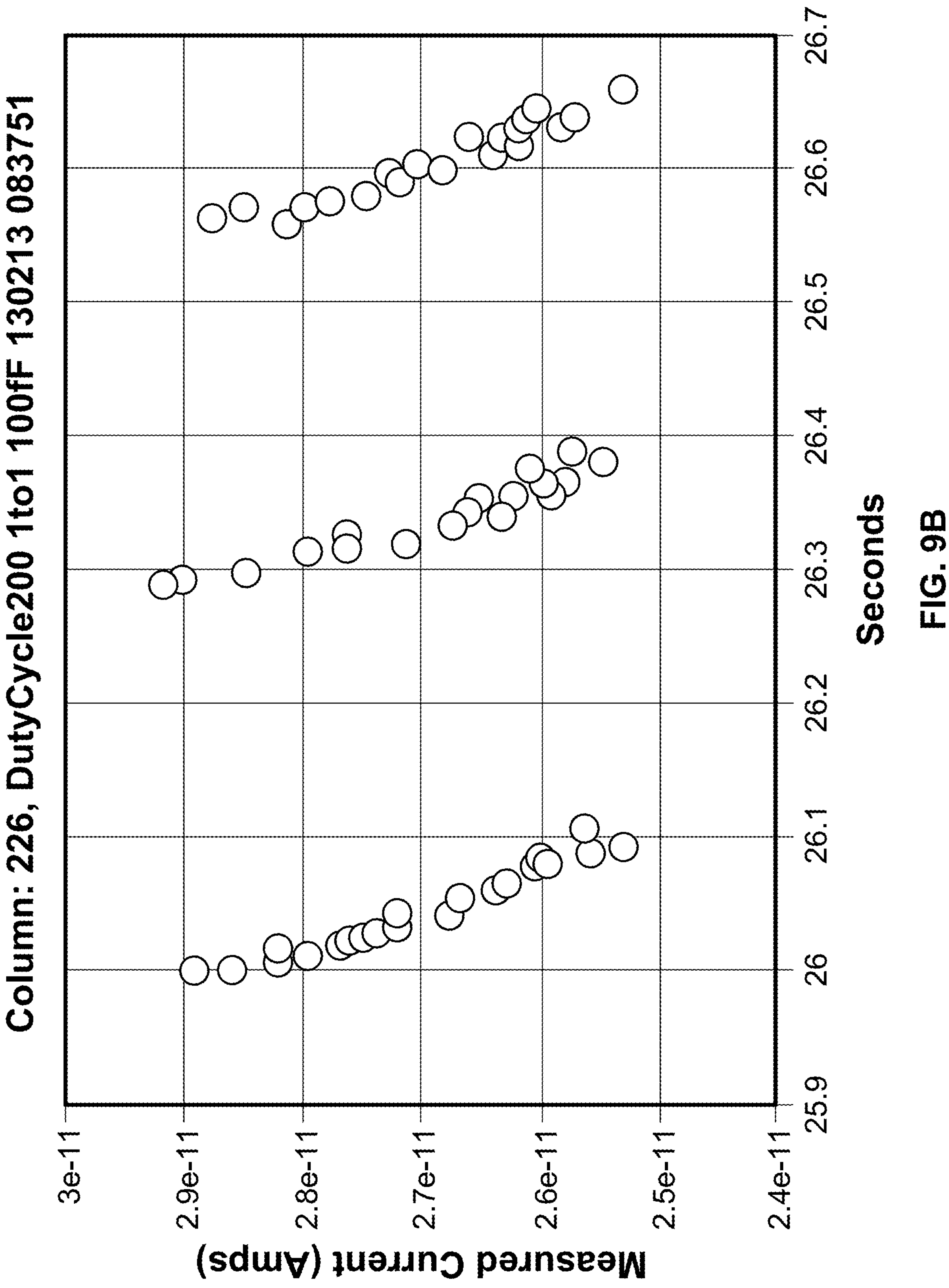

FIGS. 9A and 9B illustrate the nanopore current with non-faradaic AC modulation. In this example, the applied signal is a 200 mV peak to peak square wave with a 50% duty cycle at 5 Hz. The electrolyte contains 0.5 M Potassium Acetate and 10 mM KCl. The counter electrode 616 includes AgCl. The working electrode 610 is a platinum electrode with electroplated platinum.

FIG. 9A shows the startup transient when 200 mV with positive polarity is applied to the nanopore, indicating that the open-channel current with 200 mV directly applied is approximately 70 pA. FIG. 9A shows that the steady state is reached after ~20 seconds. In FIG. 9B, the decay rate of the voltage on the double layer capacitor can be observed. The decay rate is determined by the size of the double layer capacitance and the nanopore load resistance.

Figure 10:
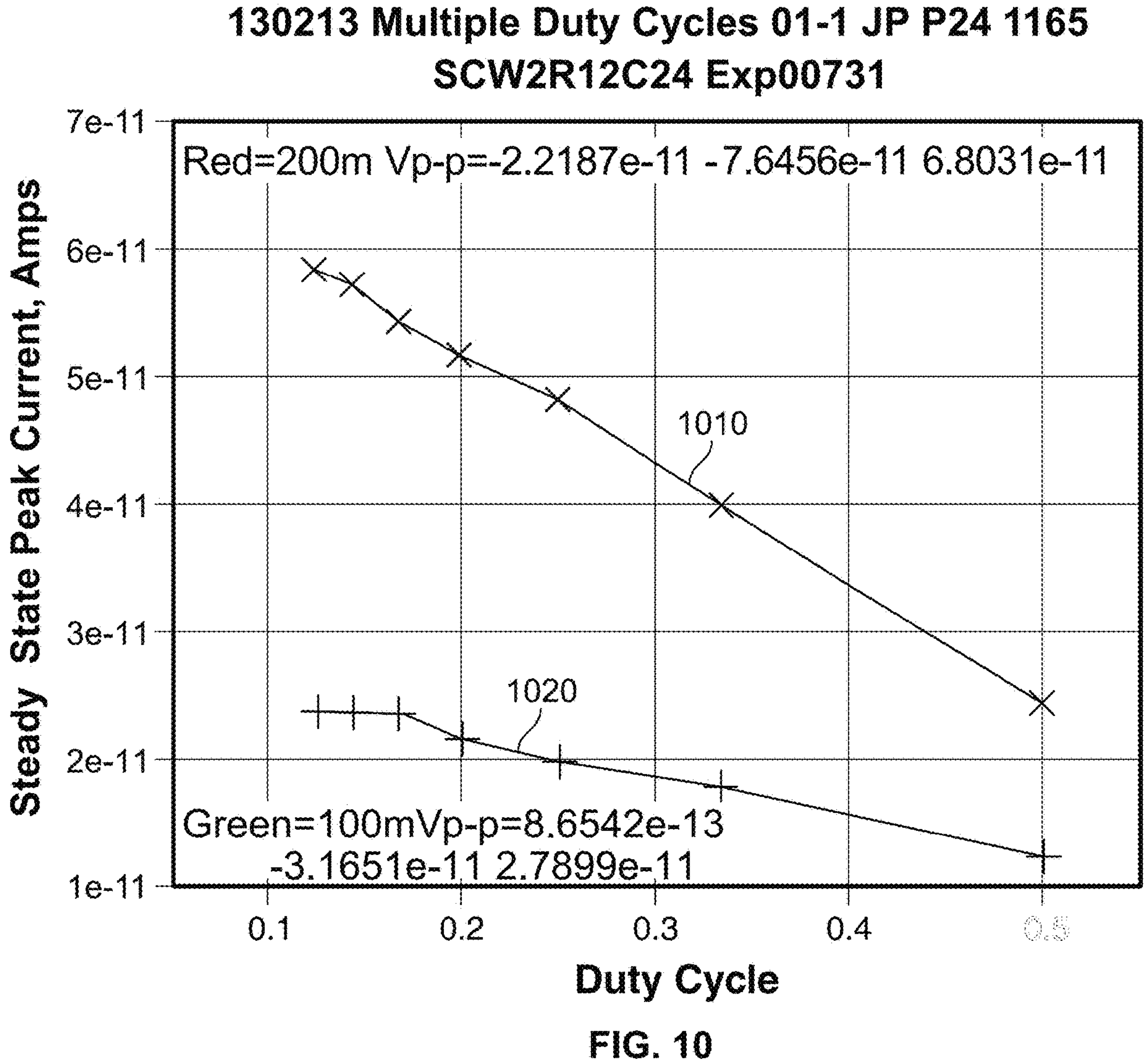
FIG. 10 illustrates that the peak positive current at steady state varies as a function of duty cycle and applied voltage.

FIG. 10 illustrates that the peak positive current at steady state varies as a function of duty cycle and applied voltage. Plot 1010 shows the steady state peak current in amperes (A) plotted against different duty cycles when the applied voltage is a 200 mV peak to peak square wave. Plot 1020 shows the steady state peak current (in A) plotted against different duty cycles when the applied voltage is a 100 mV peak to peak square wave. In this example, the electrolyte contains 0.5 M Potassium Acetate and 10 mM KCl. The counter electrode 616 includes AgCl. The working electrode 610 is a platinum electrode with electroplated platinum. Since the hemolysin nanopore has a rectifying characteristic (or is non-ohmic), a larger magnitude negative polarity voltage is required to pass the same magnitude of current than when a positive polarity voltage is applied. The peak positive current drops as the duty cycle is increased. The lower the duty cycle, the higher the positive voltage applied to the nanopore through the double layer capacitance.

Figure 12A:
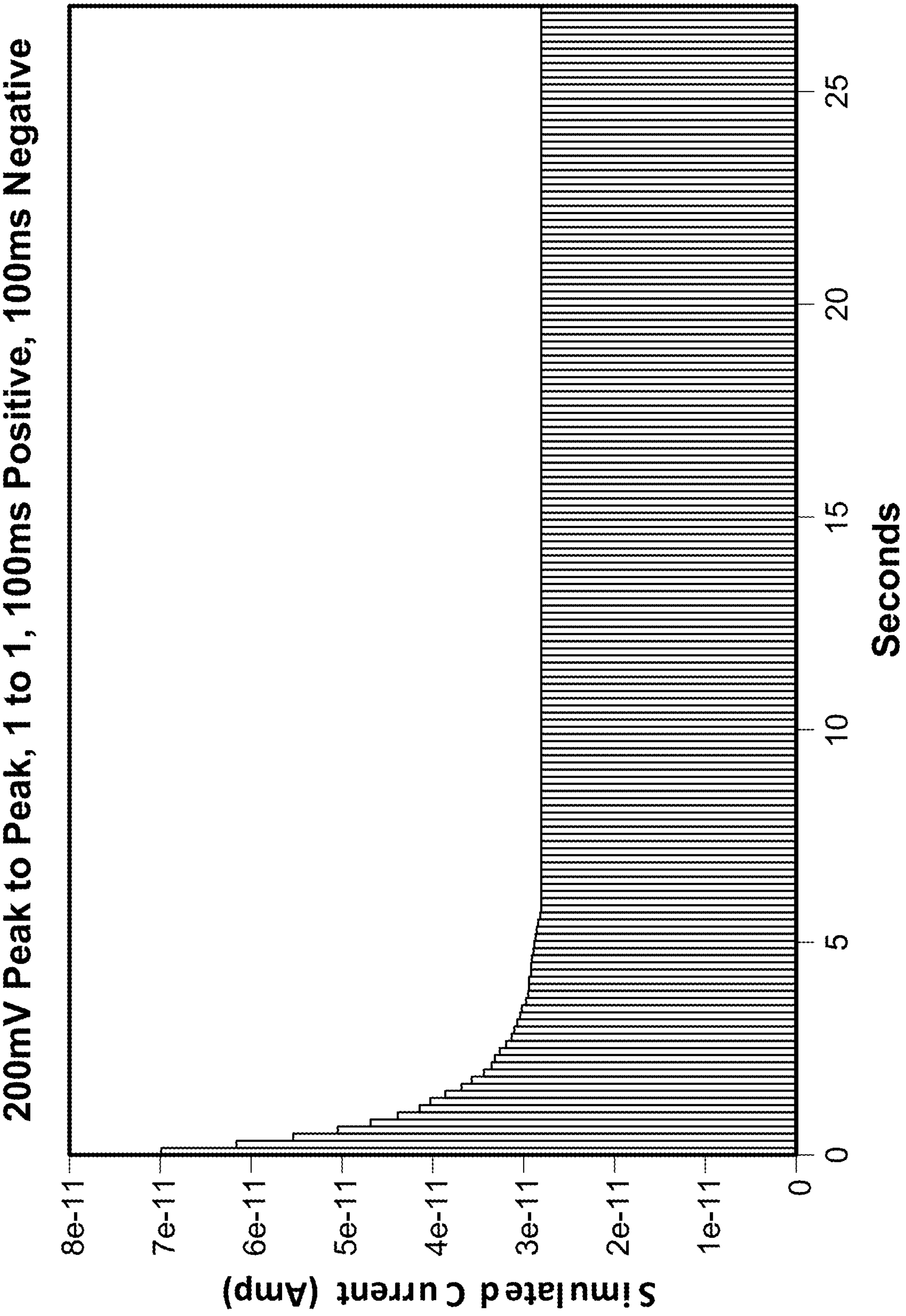
FIGS. 12A and 12B illustrate the simulation result when the applied signal has a 50% duty cycle.
Figure 12B:
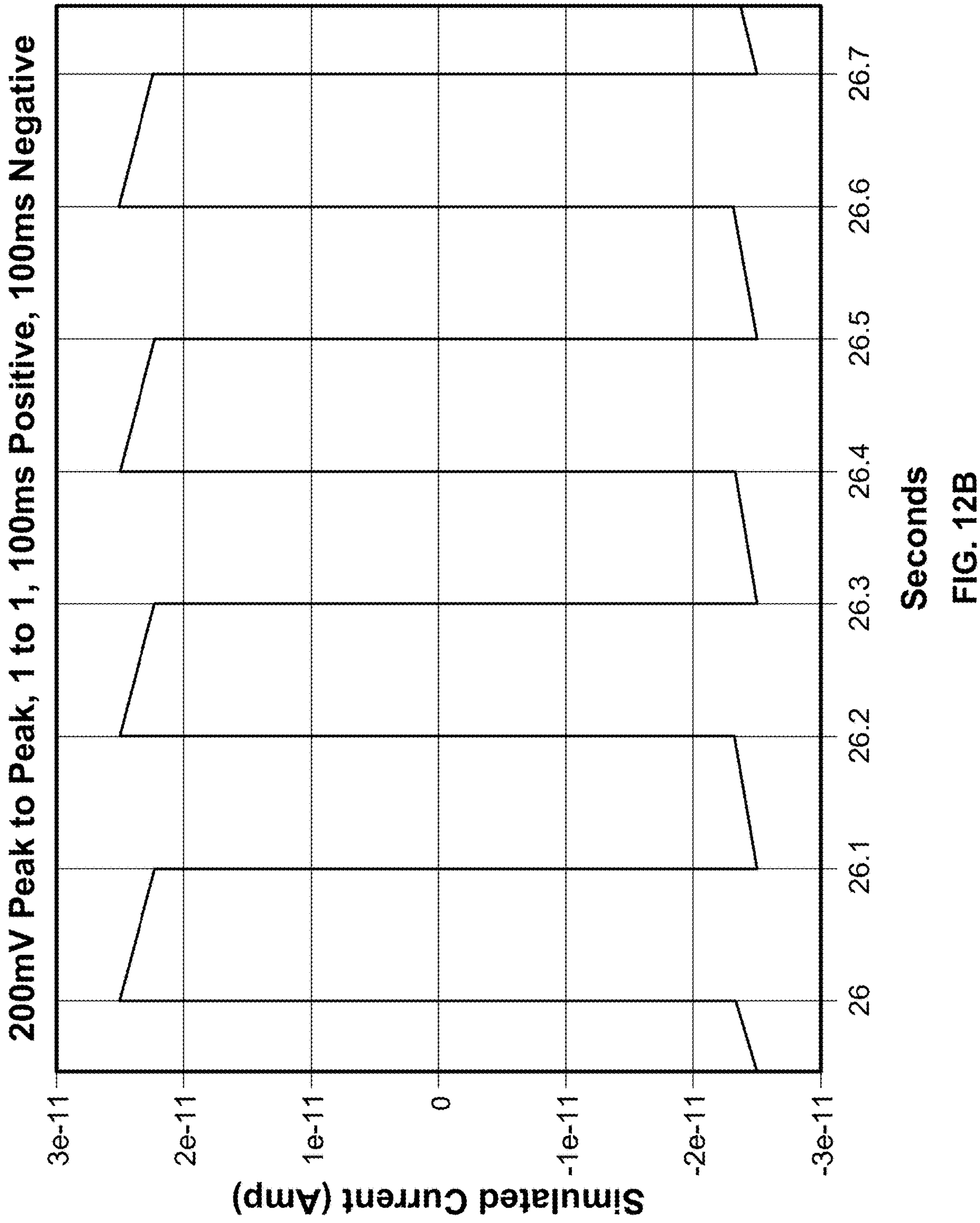

FIG. 11 illustrates an embodiment of a simulation model that was matched to the data of FIG. 10. The simulation is constructed to estimate the actual voltage on the nanopore, which is not the same as the voltage applied to the working electrode because of the double layer capacitor connected in series with the nanopore. This voltage cannot be directly measured in the non-faradaic cases. The non-linearity in potassium acetate was assumed to be directly proportional to the 1 M potassium chloride non-linearity. FIGS. 12A and 12B illustrate the simulation result when the applied signal has a 50% duty cycle. In FIG. 12B, the slope of the decay is steeper for the positive current than the negative current because of the rectifying characteristics of the hemolysin nanopore, which is modeled with the polynomial equations B1 and B2 in FIG. 11.

Figure 13A:
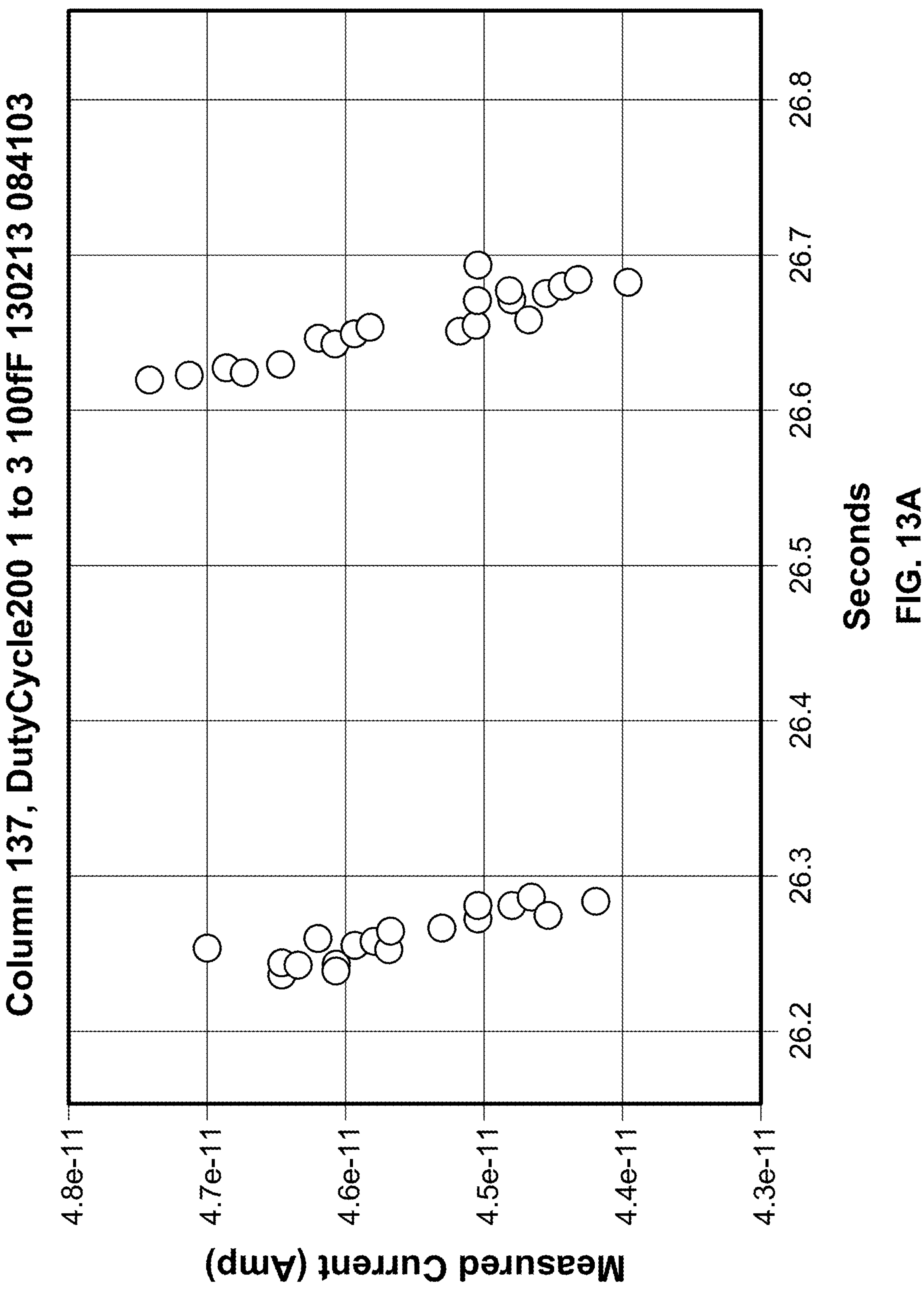
FIG. 13A illustrates the measurement current when the applied signal has a 25% duty cycle.
Figure 13B:
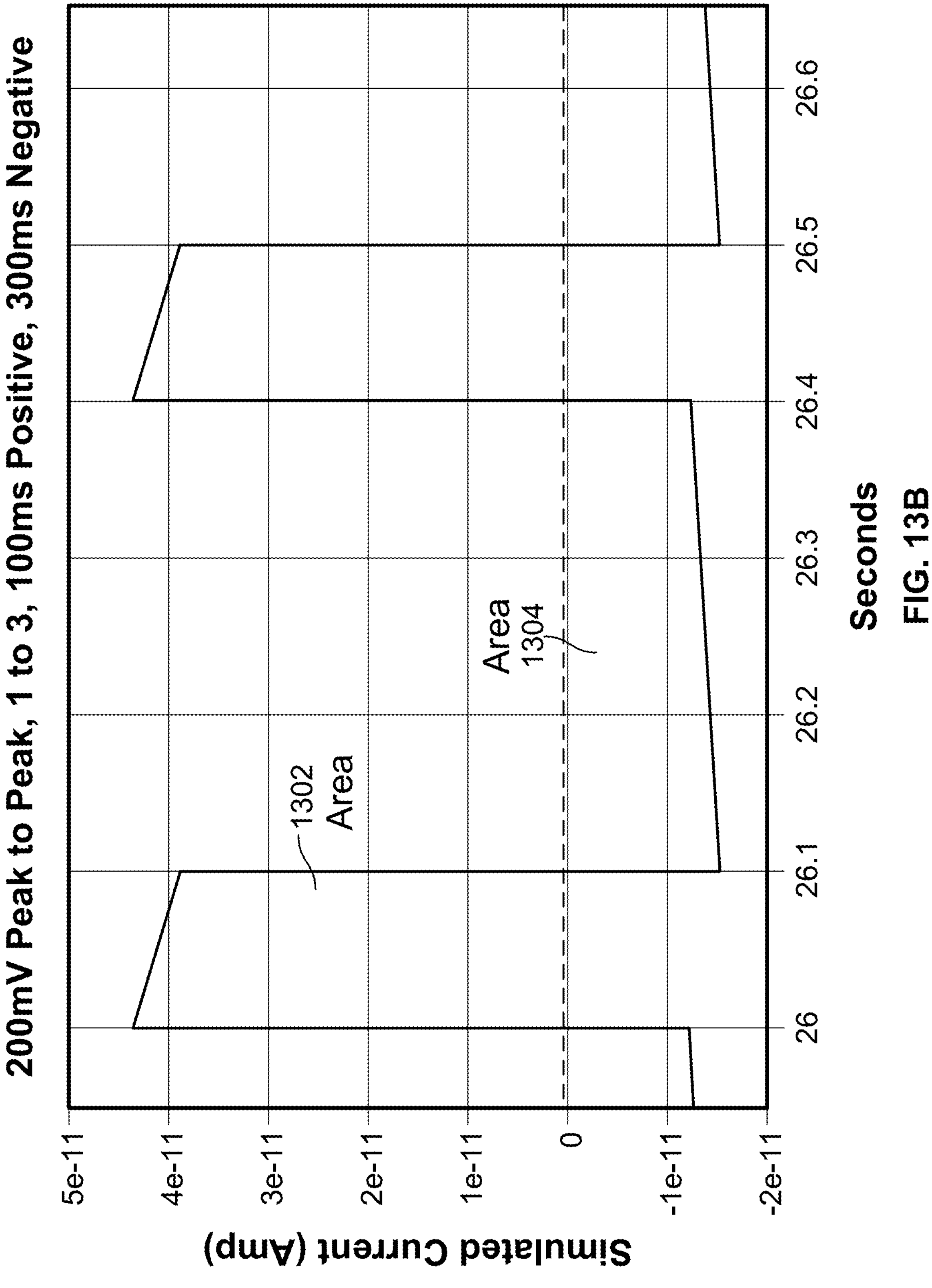
FIG. 13B illustrates the simulated current when the applied signal has a 25% duty cycle.

FIG. 13A illustrates the measurement current when the applied signal has a 25% duty cycle. FIG. 13B illustrates the simulated current when the applied signal has a 25% duty cycle. These figures illustrate that with a lower duty cycle of 25%, the magnitude of the positive current (43 pA) through the nanopore is much larger than the magnitude of the negative current (−13 pA) through the nanopore. In order to achieve no shunt resistance (no faradaic current) at steady state, the sum of the positive and negative charge through the double layer over one period of oscillation should be zero. As i=dQ/dt, where i=current and Q=charge, in a graph of current versus time, charge is the area under the curve. For example, if the area under the curve of the current versus time plot of positive polarity (area 1302 of FIG. 13B) is roughly the same as the area under the curve of the current versus time plot of negative polarity (area 1304 of FIG. 13B), then the sum of the positive and negative charge through the double layer over one period of oscillation is close to zero.

Figure 14A:
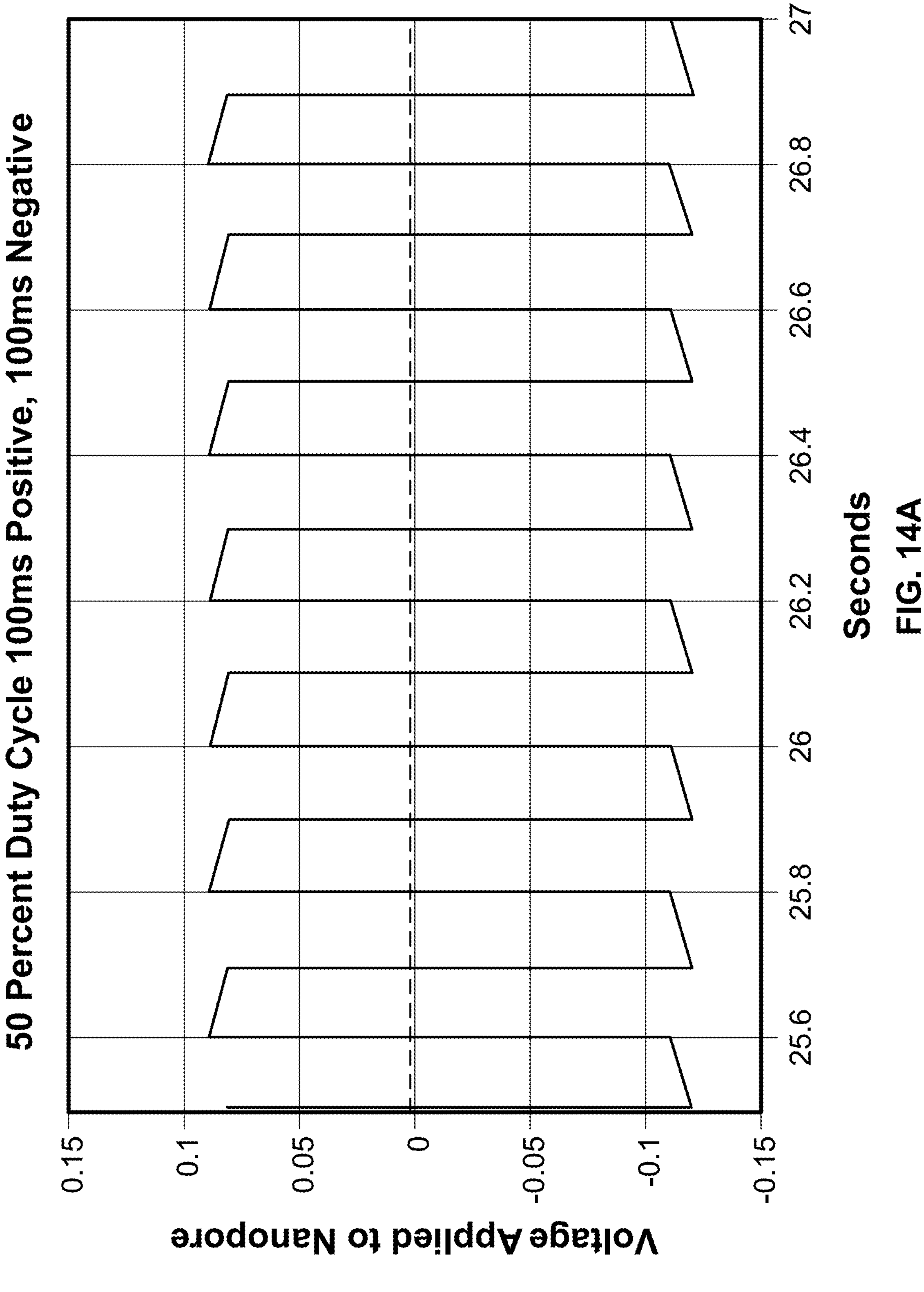
FIG. 14A illustrates the voltage applied to the nanopore versus time when the applied signal has a 50% duty cycle.
Figure 14B:
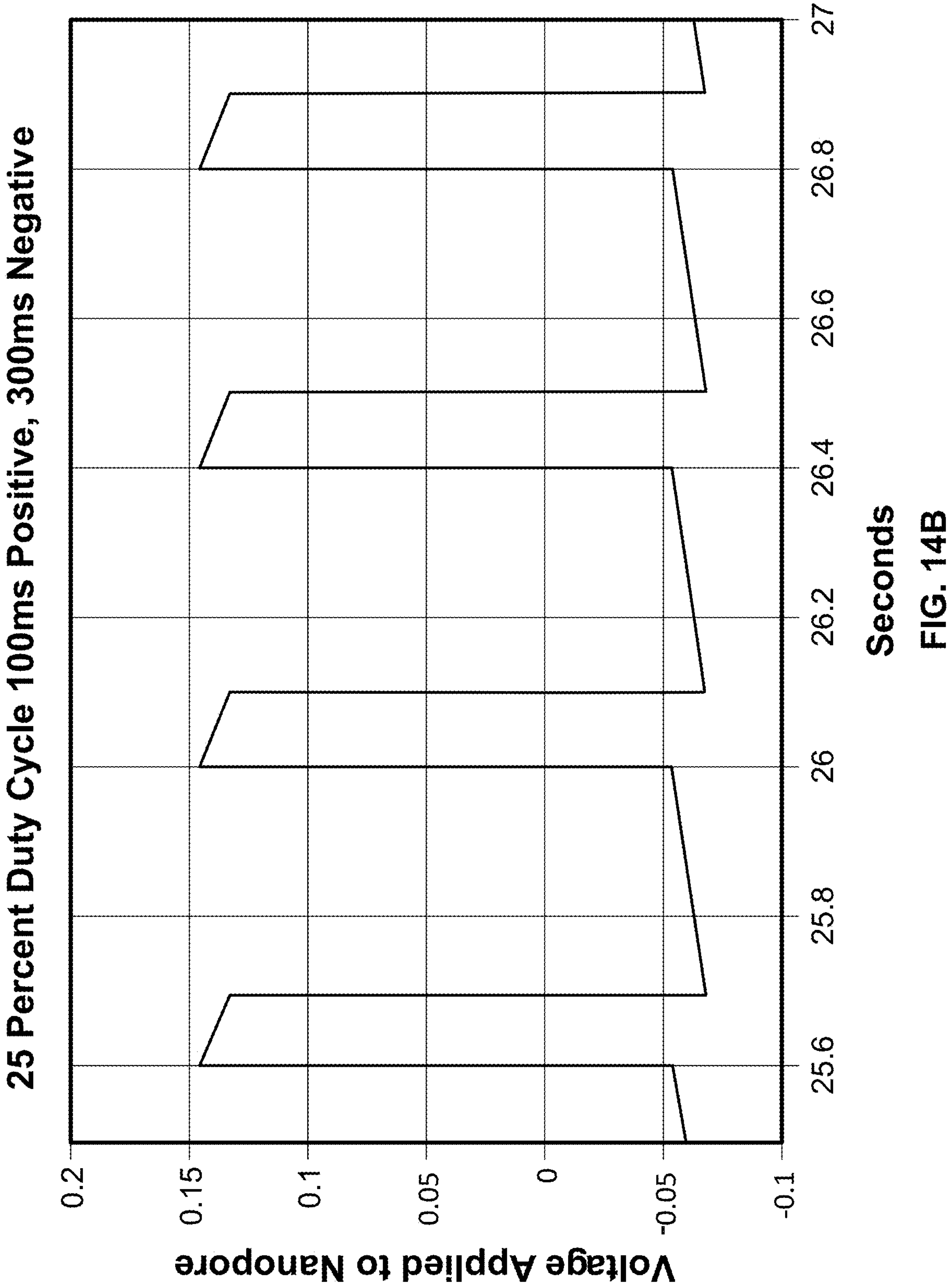
FIG. 14B illustrates the voltage applied to the nanopore versus time when the applied signal has a 25% duty cycle.

FIG. 14A illustrates the voltage applied to the nanopore versus time when the applied signal has a 50% duty cycle. FIG. 14B illustrates the voltage applied to the nanopore versus time when the applied signal has a 25% duty cycle. With a lower duty cycle in FIG. 14B, the voltage applied to the nanopore is higher, which draws the polymerase and the tag towards the nanopore with greater efficacy. With a longer duty cycle in FIG. 14A, more time is spent in reading and detecting the tag while a nucleotide specific tail is in place.

Figure 15:
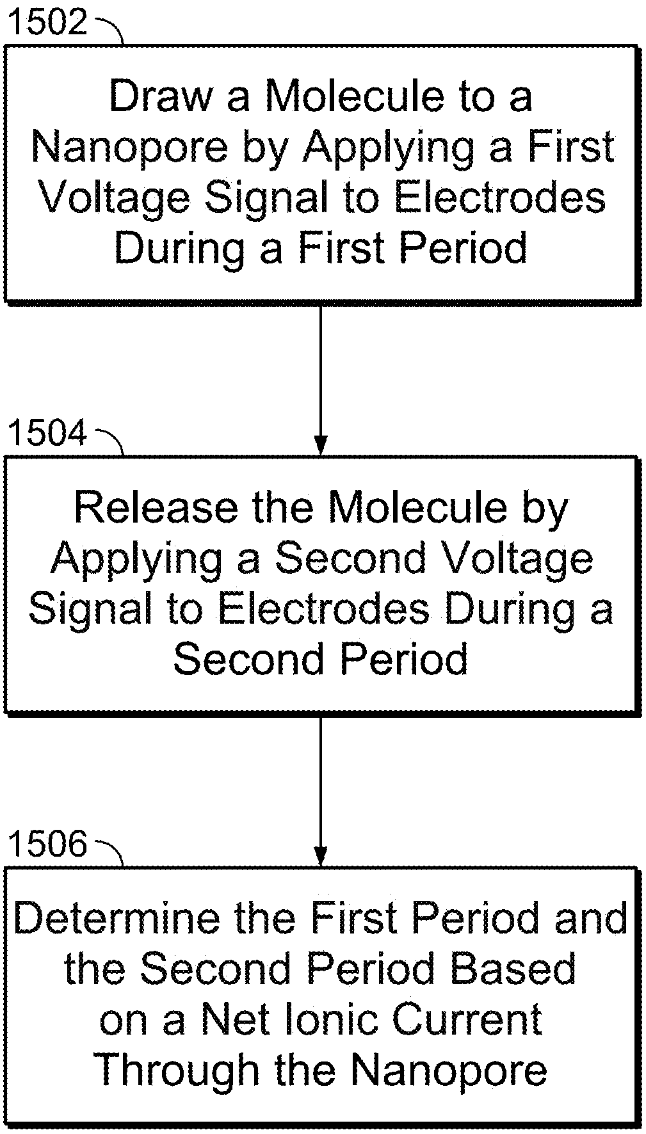
FIG. 15 illustrates an embodiment of a process for identifying a molecule.

FIG. 15 illustrates an embodiment of a process for identifying a molecule. At 1502, a molecule is drawn to a nanopore by applying a first voltage signal to a pair of electrodes (e.g., the working electrode and the counter/reference electrode) during a first period, wherein the first voltage signal causes a first ionic current through the nanopore that is indicative of a property of a portion of the molecule (e.g., a tagged nucleotide) proximate to the nanopore. For example, the four types of tagged nucleotides have different properties and when a particular type of tagged nucleotide is drawn into the nanopore, an ionic current indicative of the property flows through the nanopore.

At 1504, the molecule is released from the nanopore by applying a second voltage signal to the pair of electrodes during a second period, wherein the second voltage signal causes a second ionic current through the nanopore.

At 1506, the first period and the second period are determined based at least in part on a net ionic current through the nanopore comprising the first ionic current and the second ionic current. For example, the first period and the second period can be determined such that the net ionic current is reduced. In some embodiments, the net ionic current is reduced by setting the second voltage signal to off. When the second voltage signal is turned off, the second ionic current becomes zero and the depletion of the metal electrode is delayed as explained above. In some embodiments, the net ionic current is reduced by setting the second voltage signal to a signal with a polarity opposite from the first voltage signal. For example, alternating between the first voltage signal and the second voltage signal makes an AC signal. The second ionic current offsets the first ionic current, thus reducing the net ionic current through the nanopore. As shown in FIG. 10, the current varies as a function of duty cycle and applied voltage. Therefore, the duty cycle (i.e., the first period and the second period) can be adjusted such that the area under the curve of the first ionic current is substantially the same as the area under the curve of the second ionic current such that the sum of the positive and negative charge through the double layer over one period of oscillation (i.e., the first period and the second period) is close to zero.

Figure 16:
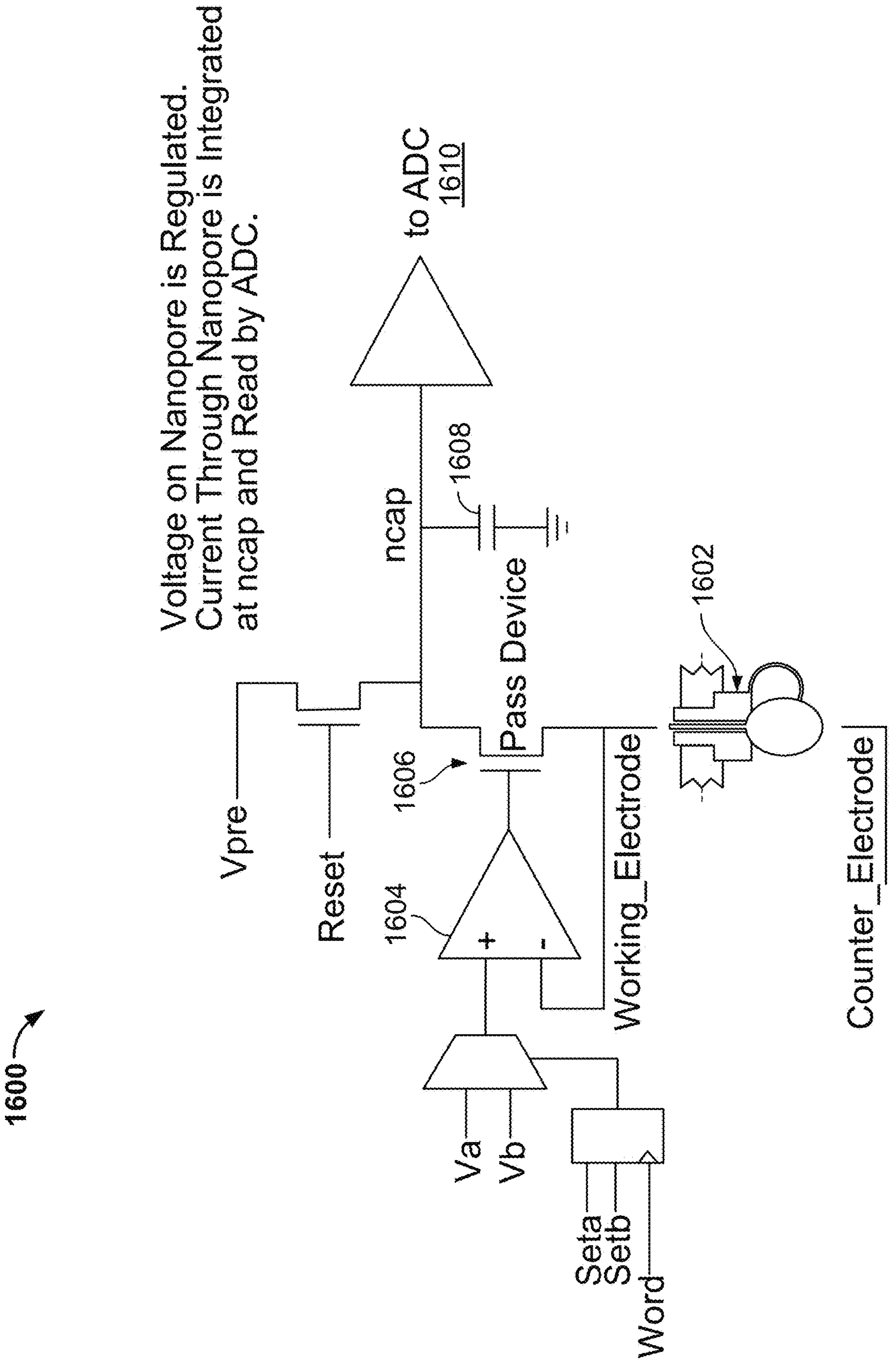
FIG. 16 illustrates an embodiment of a circuitry 1600 in a cell of a nanopore-based sequencing chip.

FIG. 16 illustrates an embodiment of a circuitry 1600 in a cell of a nanopore-based sequencing chip. As mentioned above, when the tag is held in nanopore 1602, a unique conductance signal (e.g., see signal 210 in FIG. 2) is generated due to the tag's distinct chemical structures, thereby identifying the added base electronically. The circuitry in FIG. 16 maintains a constant voltage across nanopore 1602 when the current flow is measured. In particular, the circuitry includes an operational amplifier 1604 and a pass device 1606 that maintain a constant voltage equal to $V_a$ or $V_b$ across nanopore 1602. The current flowing through nanopore 1602 is integrated at a capacitor $n_{cap}$ 1608 and measured by an Analog-to-Digital (ADC) converter 1610.

However, circuitry 1600 has a number of drawbacks. One of the drawbacks is that circuitry 1600 only measures unidirectional current flow. Another drawback is that operational amplifier 1604 in circuitry 1600 may introduce a number of performance issues. For example, the offset voltage and the temperature drift of operational amplifier 1604 may cause the actual voltage applied across nanopore 1602 to vary across different cells. The actual voltage applied across nanopore 1602 may drift by tens of millivolts above or below the desired value, thereby causing significant measurement inaccuracies. In addition, the operational amplifier noise may cause additional detection errors. Another drawback is that the portions of the circuitry for maintaining a constant voltage across the nanopore while current flow measurements are made are area-intensive. For example, operational amplifier 1604 occupies significantly more space in a cell than other components. As the nanopore-based sequencing chip is scaled to include more and more cells, the area occupied by the operational amplifiers may increase to an unattainable size. Unfortunately, shrinking the operational amplifier's size in a nanopore-based sequencing chip with a large-sized array may raise other performance issues. For example, it may exacerbate the offset and noise problems in the cells even further.

Figure 17:
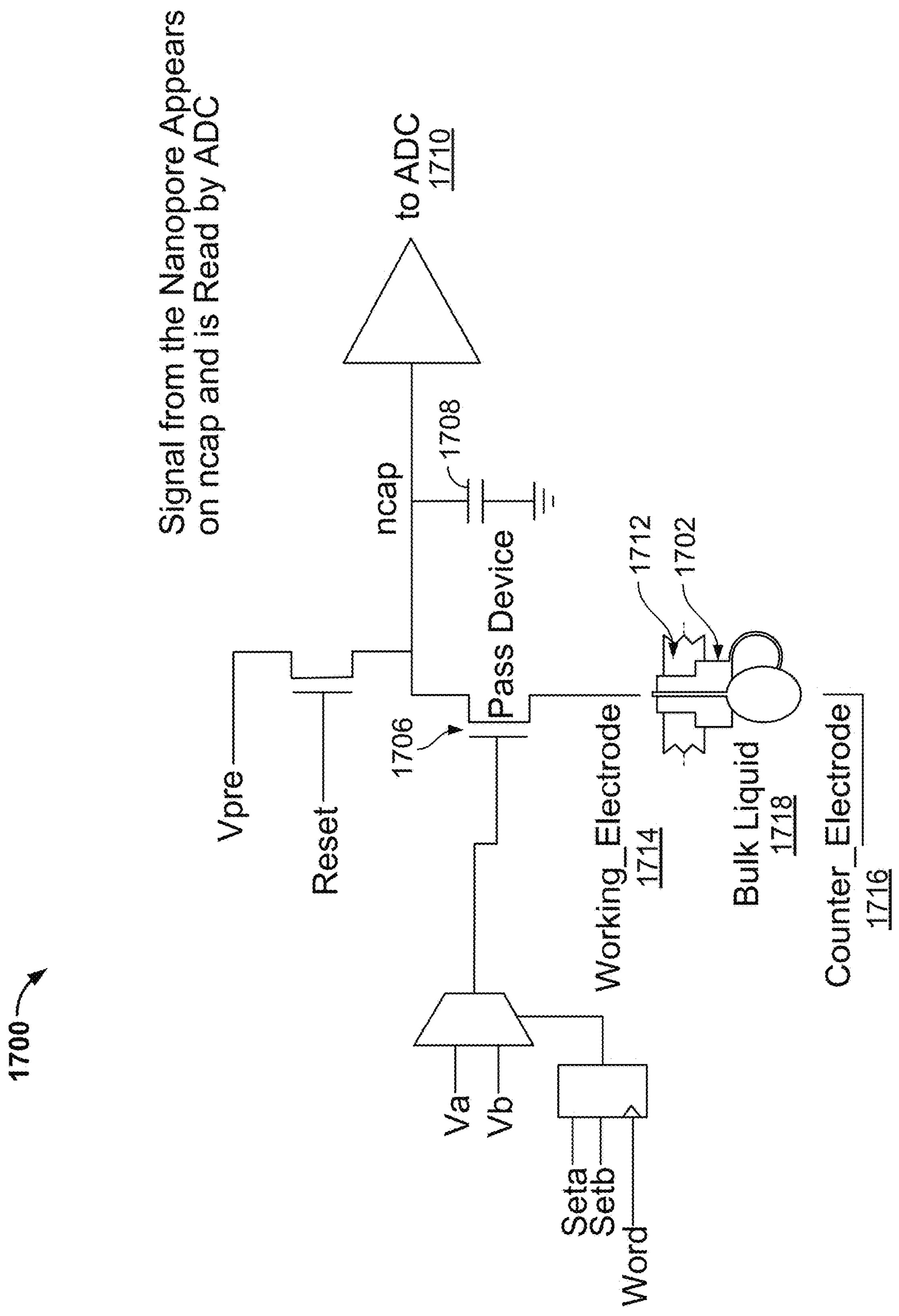
FIG. 17 illustrates an embodiment of a circuitry 1700 in a cell of a nanopore-based sequencing chip, wherein the voltage applied across the nanopore can be configured to vary over a time period during which the nanopore is in a particular detectable state.
Figure 18A:
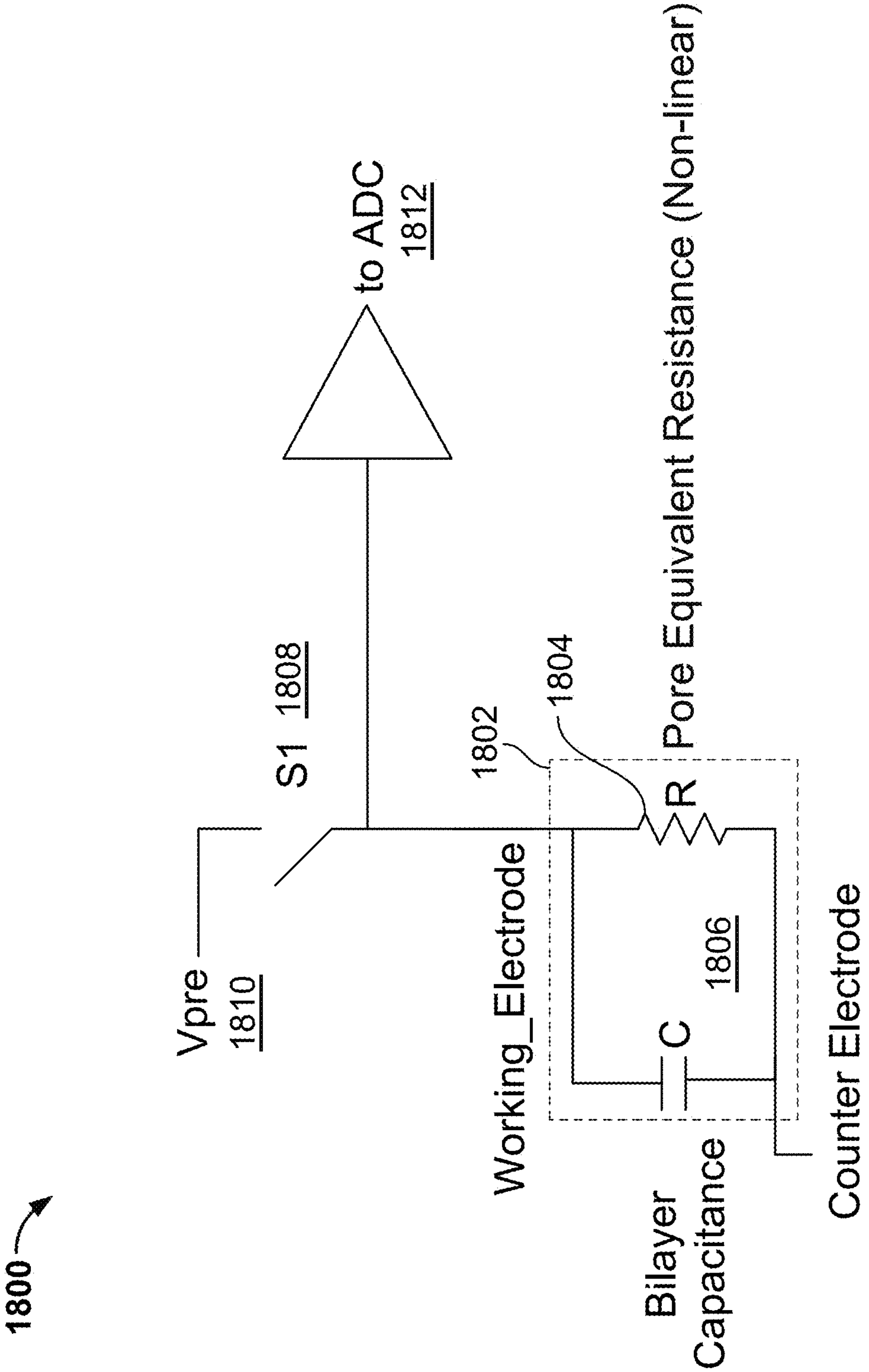
FIGS. 18A and 18B illustrate additional embodiments of a circuitry (1800 and 1801) in a cell of a nanopore-based sequencing chip, wherein the voltage applied across the nanopore can be configured to vary over a time period during which the nanopore is in a particular detectable state.
Figure 18B:
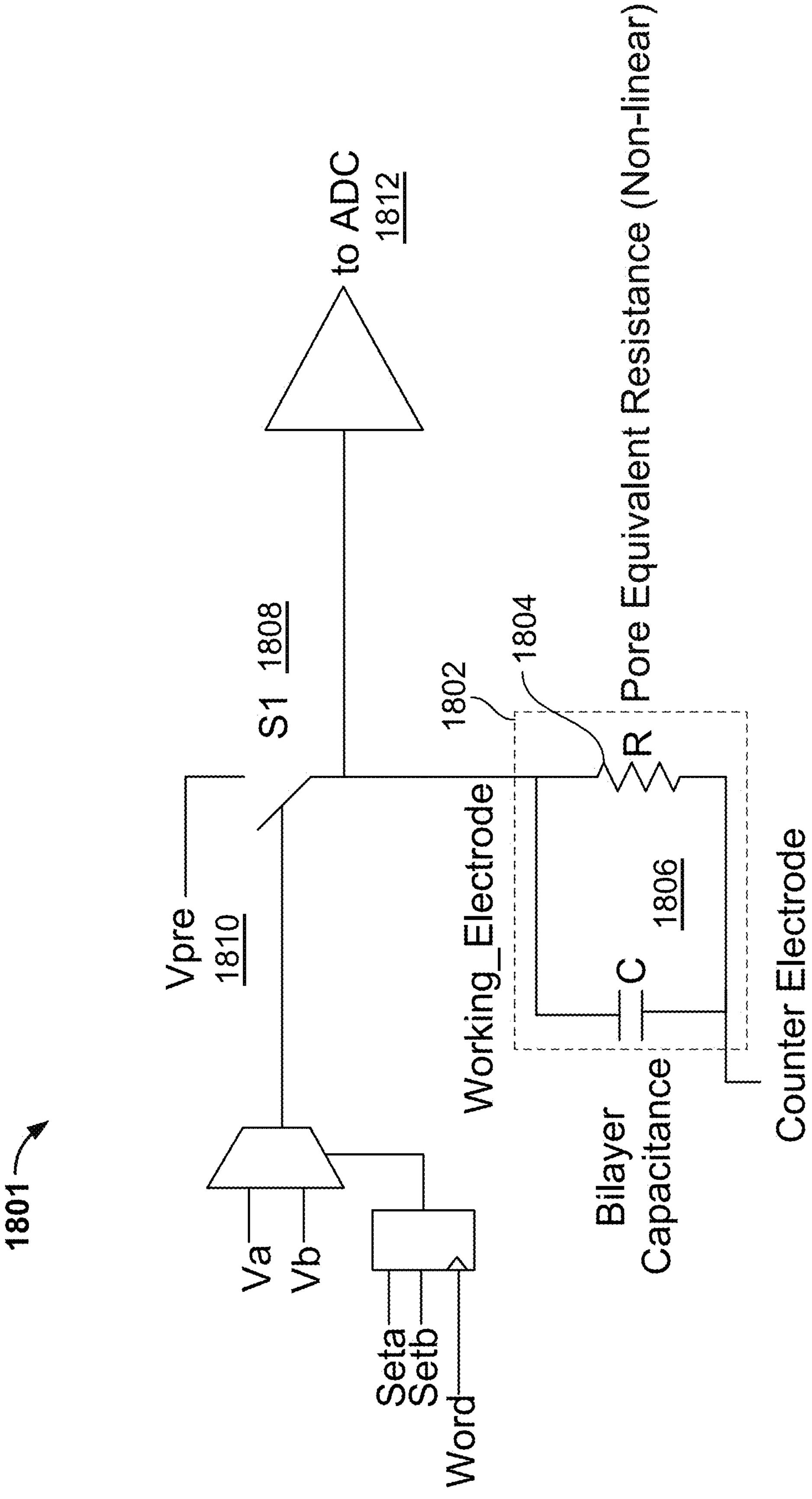

FIG. 17 illustrates an embodiment of a circuitry 1700 in a cell of a nanopore-based sequencing chip, wherein the voltage applied across the nanopore can be configured to vary over a time period during which the nanopore is in a particular detectable state. One of the possible states of the nanopore is an open-channel state when a tag-attached polyphosphate is absent from the barrel of the nanopore. Another four possible states of the nanopore correspond to the states when the four different types of tag-attached polyphosphate nucleotides (A, T, G, or C) are held in the barrel of the nanopore. Yet another possible state of the nanopore is when the membrane is ruptured. FIGS. 18A and 18B illustrate additional embodiments of a circuitry (1800 and 1801) in a cell of a nanopore-based sequencing chip, wherein the voltage applied across the nanopore can be configured to vary over a time period during which the nanopore is in a particular detectable state. In the above circuits, the operational amplifier is no longer required.

FIG. 17 shows a nanopore 1702 that is inserted into a membrane 1712, and nanopore 1702 and membrane 1712 are situated between a cell working electrode 1714 and a counter electrode 1716, such that a voltage is applied across nanopore 1702. In some embodiments, pass device 1706 that maintain a constant voltage equal to $V_a$ or $V_b$ across nanopore 1702. The current flowing through nanopore 1702 is integrated at a capacitor $n_{cap}$ 1708 and measured by an Analog-to-Digital (ADC) converter 1710. Nanopore 1702 is also in contact with a bulk liquid/electrolyte 1718. Note that nanopore 1702 and membrane 1712 are drawn upside down as compared to the nanopore and membrane in FIG. 1. Hereinafter, a cell is meant to include at least a membrane, a nanopore, a working cell electrode, and the associated circuitry. In some embodiments, the counter electrode is shared between a plurality of cells, and is therefore also referred to as a common electrode. The common electrode can be configured to apply a common potential to the bulk liquid in contact with the nanopores in the measurements cells. The common potential and the common electrode are common to all of the measurement cells. There is a working cell electrode within each measurement cell; in contrast to the common electrode, working cell electrode 1714 is configurable to apply a distinct potential that is independent from the working cell electrodes in other measurement cells.

In FIGS. 18A and 18B, instead of showing a nanopore inserted in a membrane and the liquid surrounding the nanopore, an electrical model 1802 representing the electrical properties of the nanopore and the membrane. Electrical model 1802 includes a capacitor 1806 that models a capacitance associated with the membrane ($C_{membrane}$) and a resistor 1804 that models a resistance associated with the nanopore in different states (e.g., the open-channel state or the states corresponding to having different types of tags/molecules inside the nanopore). The capacitance associated with the working electrode may be referred to as a double layer capacitance ($C_{dl}$). Note in FIGS. 18A and 18B that the respective circuitry may not require an extra capacitor (e.g., $n_{cap}$ 1608 in FIG. 16) that is fabricated on-chip, thereby facilitating the reduction in size of the nanopore-based sequencing chip.

Figure 19:
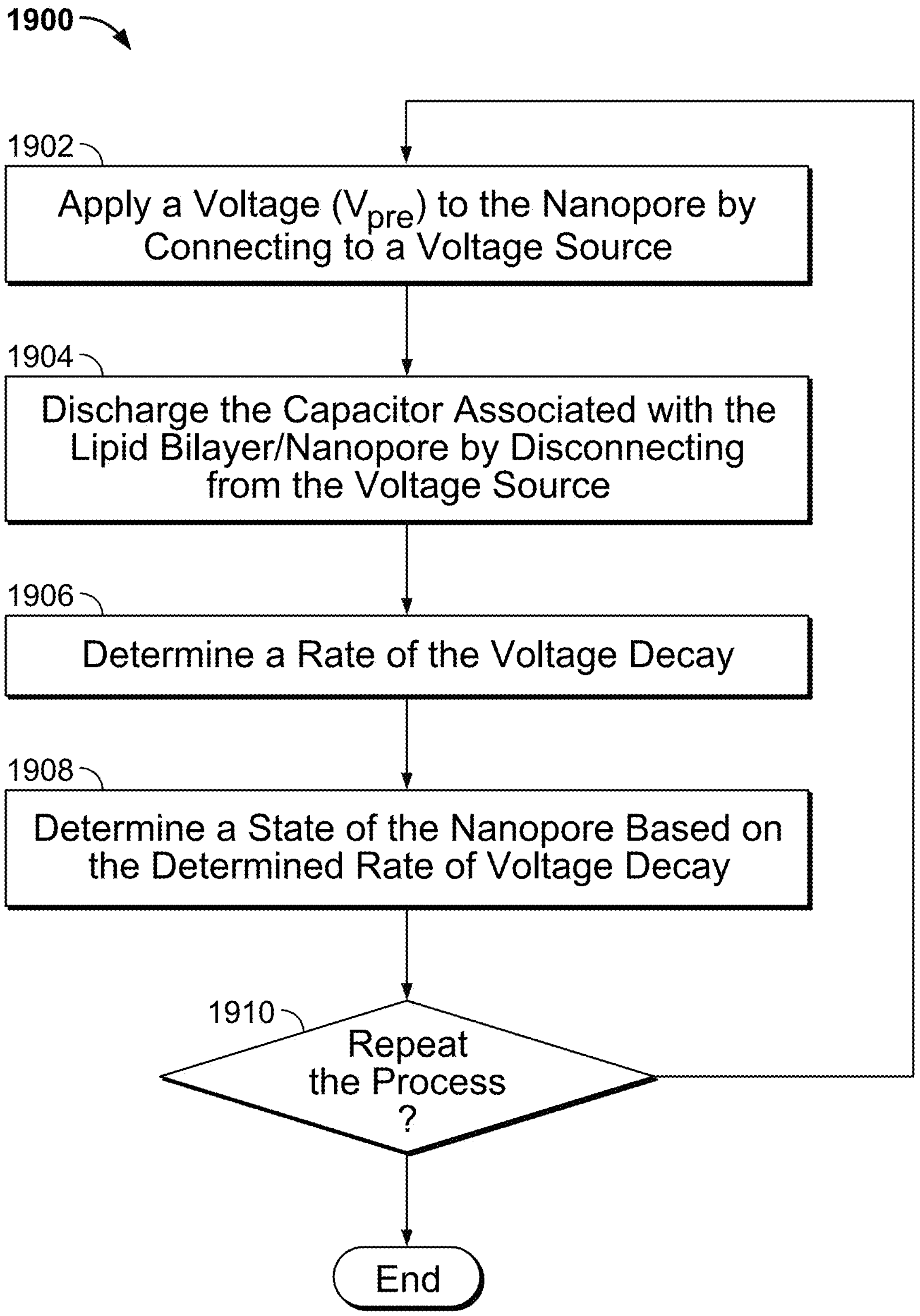
FIG. 19 illustrates an embodiment of a process 1900 for analyzing a molecule inside a nanopore, wherein the nanopore is inserted in a membrane.
Figure 20:
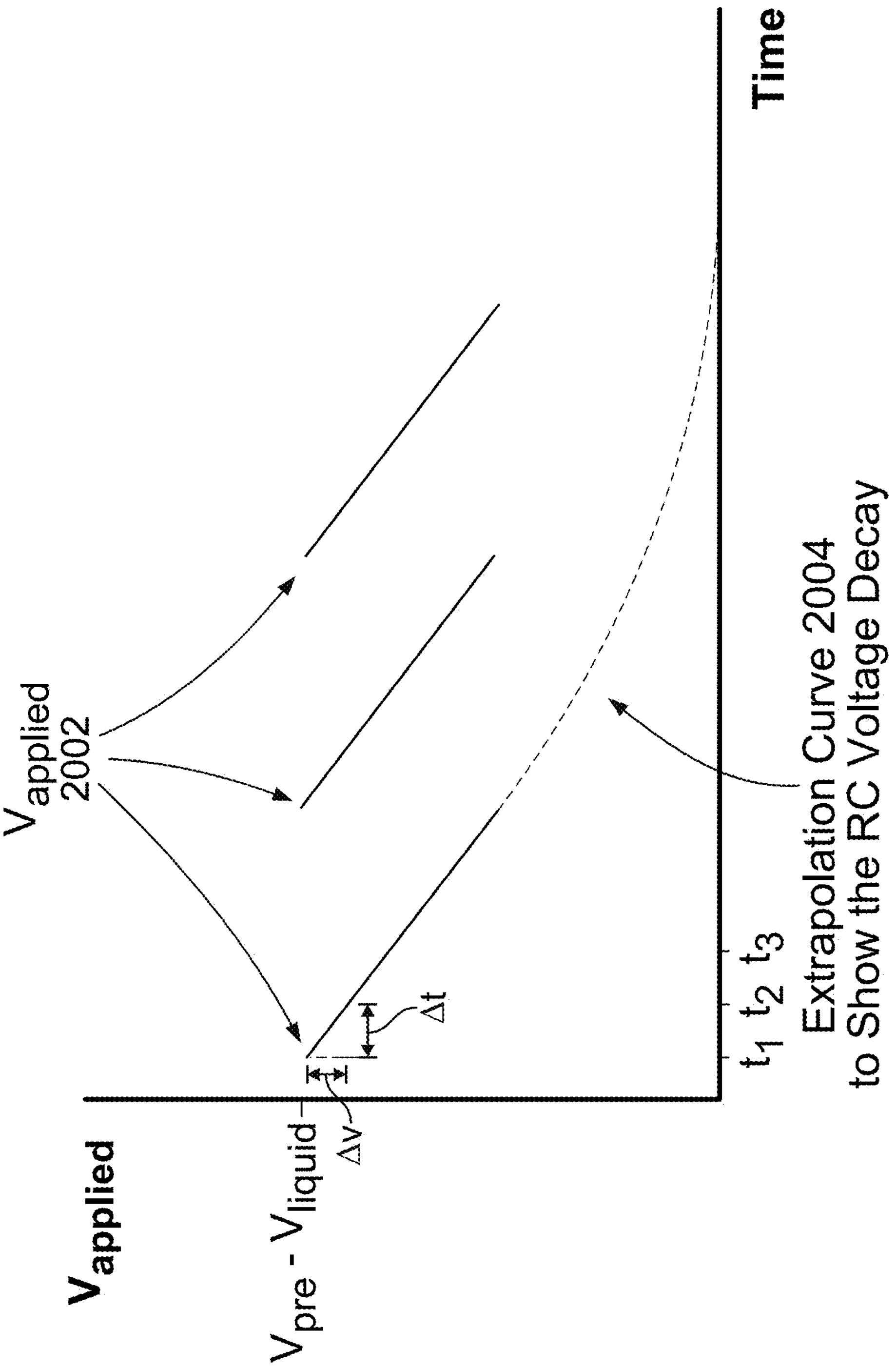
FIG. 20 illustrates an embodiment of a plot of the voltage applied across the nanopore versus time when process 1900 is performed and repeated three times.

FIG. 19 illustrates an embodiment of a process 1900 for analyzing a molecule inside a nanopore, wherein the nanopore is inserted in a membrane. Process 1900 may be performed using the circuitries shown in FIG. 17, 18A, or 18B. FIG. 20 illustrates an embodiment of a plot of the voltage applied across the nanopore versus time when process 1900 is performed and repeated three times. As will be described in greater detail below, the voltage applied across the nanopore is not held constant. In contrast, the voltage applied across the nanopore changes over time. The rate of the voltage decay (i.e., the steepness of the slope of the applied voltage across the nanopore versus time plot) depends on the cell resistance (e.g., the resistance of resistor 1804 in FIG. 18A). More particularly, as the resistance associated with the nanopore in different states (e.g., the open-channel state, the states corresponding to having different types of tags/molecules inside the nanopore, and the state when the membrane is ruptured) is different due to the molecules'/tags' distinct chemical structures, different corresponding rates of voltage decay may be observed and thus may be used to identify the different states of the nanopore.

With reference to FIG. 19 and FIG. 18A, at 1902 of process 1900, a voltage is applied across the nanopore by coupling the nanopore to a voltage source. For example, as shown in FIG. 18A, a voltage $V_{pre}$ 1810 is applied to the cell working electrode when a switch S1 1808 is closed. As shown in FIG. 20, the initial voltage applied across the nanopore is $V_{pre}-V_{liquid}$, where $V_{liquid}$ is the voltage of the bulk liquid in contact with the nanopore. As the voltage source is connected to the working electrode, the capacitor associated with the membrane is charged and energy is stored in an electric field across the membrane.

At 1904 of process 1900, the capacitor associated with the membrane (capacitor 1806) is discharged by decoupling the nanopore and the membrane from the voltage source, and the energy stored in the electric field across the membrane is thereby dissipated. For example, as shown in FIG. 18A, the voltage source is disconnected when switch S1 1808 is opened. After switch S1 1808 is opened, the voltage across the nanopore begins to decay exponentially, as shown in FIG. 20. The exponential decay has an RC time constant $\tau=RC$, where R is the resistance associated with the nanopore (resistor 1804) and C is the capacitance associated with the membrane (capacitor 1806) in parallel with R.

At 1906 of process 1900, a rate of the decay of the voltage applied across the nanopore is determined. The rate of the voltage decay is the steepness of the slope of the applied voltage across the nanopore versus time curve, as shown in FIG. 20. The rate of the voltage decay may be determined in different ways.

In some embodiments, the rate of the voltage decay is determined by measuring a voltage decay that occurs during a fixed time interval. For example, the voltage applied at the working electrode is first measured by ADC 1812 at time $t_1$, and then the voltage is again measured by ADC 1812 at time $t_2$. The voltage difference $\Delta V_{applied}$ is greater when the slope of the voltage across the nanopore versus time curve is steeper, and the voltage difference $\Delta V_{applied}$ is smaller when the slope of the voltage curve is less steep. Thus, $\Delta V_{applied}$ may be used as a metric for determining the rate of the decay of the voltage applied across the nanopore. In some embodiments, to increase the accuracy of the measurement of the rate of voltage decay, the voltage may be measured additional times at fixed intervals. For example, the voltage may be measured at $t_3$, $t_4$, and so on, and the multiple measurements of $\Delta V_{applied}$ during the multiple time intervals may be jointly used as a metric for determining the rate of the decay of the voltage applied across the nanopore. In some embodiments, to increase the accuracy of the measurement of the rate of voltage decay, correlated double sampling (CDS) may be used.

In some embodiments, the rate of the voltage decay is determined by measuring a time duration that is required for a selected amount of voltage decay. In some embodiments, the time required for the voltage to drop from a fixed voltage $V_1$ to a second fixed voltage $V_2$ may be measured. The time required is less when the slope of the voltage curve is steeper, and the time required is greater when the slope of the voltage curve is less steep. Thus, the measured time required may be used as a metric for determining the rate of the decay of the voltage applied across the nanopore.

At 1908 of process 1900, a state of the nanopore is determined based on the determined rate of voltage decay. One of the possible states of the nanopore is an open-channel state during which a tag-attached polyphosphate is absent from the barrel of the nanopore. Other possible states of the nanopore correspond to the states when different types of molecules are held in the barrel of the nanopore. For example, another four possible states of the nanopore correspond to the states when the four different types of tag-attached polyphosphate nucleotides (A, T, G, or C) are held in the barrel of the nanopore. Yet another possible state of the nanopore is when the membrane is ruptured. The state of the nanopore can be determined based on the determined rate of voltage decay, because the rate of the voltage decay depends on the cell resistance, i.e., the resistance of resistor 1804 in FIG. 18A. More particularly, as the resistances associated with the nanopore in different states are different due to the molecules/tags' distinct chemical structures, different corresponding rates of voltage decay may be observed and thus may be used to identify the different states of the nanopore.

Figure 21:
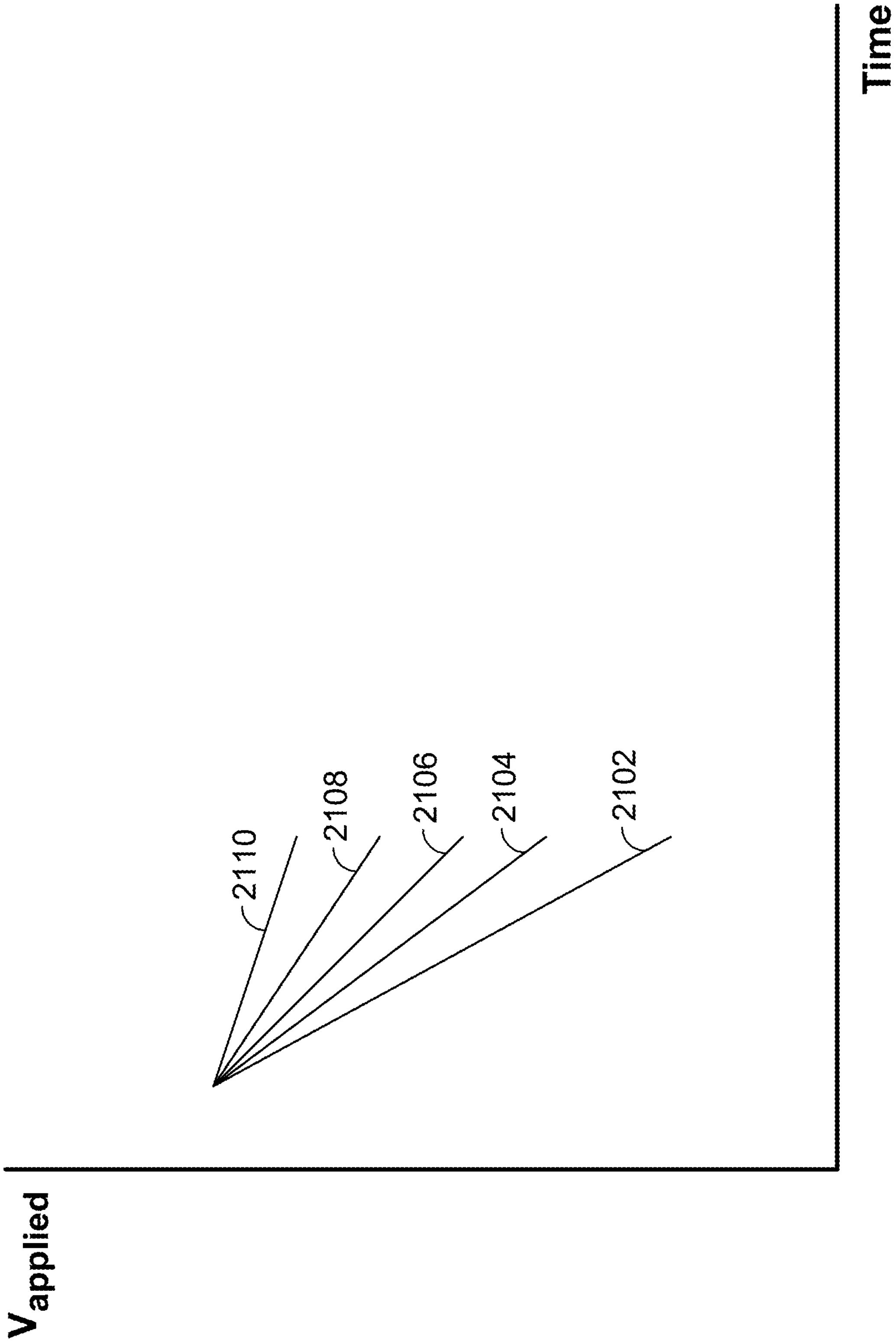
FIG. 21 illustrates an embodiment of the plots of the voltage applied across the nanopore versus time when the nanopore is in different states.

FIG. 21 illustrates an embodiment of the plots of the voltage applied across the nanopore versus time when the nanopore is in different states. Curve 2102 shows the rate of voltage decay during an open-channel state. In some embodiments, the resistance associated with the nanopore in an open-channel state is in the range of 100 Mohm to 20 Gohm. Curves 2104, 2106, 2108, and 2110 show the different rates of voltage decay corresponding to the four capture states when the four different types of tag-attached polyphosphate nucleotides (A, T, G, or C) are held in the barrel of the nanopore. In some embodiments, the resistance associated with the nanopore in a capture state is within the range of 200 Mohm to 40 Gohm. Note that the slope of each of the plots is distinguishable from each other.

At 1910 of process 1900, it is determined whether process 1900 is repeated. For example, the process may be repeated a plurality of times to detect each state of the nanopore. If the process is not repeated, then process 1900 terminates; otherwise, the process restarts at 1902 again. At 1902, a voltage is reasserted across the nanopore by connecting to the voltage source. For example, as shown in FIG. 18A, a voltage $V_{pre}$ 1810 is applied across the nanopore when switch S1 1808 is closed. As shown in FIG. 20, the applied voltage 2002 jumps back up to the level of $V_{pre}$. As process 1900 is repeated a plurality of times, a saw-tooth like voltage waveform is applied across the nanopore over time. FIG. 20 also illustrates an extrapolation curve 2004 showing the RC voltage decay over time had the voltage $V_{pre}$ 1810 not been reasserted.

As shown above, configuring the voltage applied across the nanopore to vary over a time period during which the nanopore is in a particular detectable state has many advantages. One of the advantages is that the elimination of the operational amplifier, the pass device, and the capacitor (e.g., $n_{cap}$ 1608 in FIG. 16) that are otherwise fabricated on-chip in the cell circuitry significantly reduces the footprint of a single cell in the nanopore-based sequencing chip, thereby facilitating the scaling of the nanopore-based sequencing chip to include more and more cells (e.g., having millions of cells in a nanopore-based sequencing chip). The capacitance in parallel with the nanopore includes two portions: the capacitance associated with the membrane and the capacitance associated with the integrated chip (IC). Due to the thin nature of the membrane, the capacitance associated with the membrane alone can suffice to create the required RC time constant without the need for additional on-chip capacitance, thereby allowing significant reduction in cell size and chip size.

Another advantage is that the circuitry of a cell does not suffer from offset inaccuracies because $V_{pre}$ is applied directly to the working electrode without any intervening circuitry. Another advantage is that since no switches are being opened or closed during the measurement intervals, the amount of charge injection is minimized.

Furthermore, the technique described above operates equally well using positive voltages or negative voltages. Bidirectional measurements have been shown to be helpful in characterizing a molecular complex. In addition, bidirectional measurements are required when the type of ionic flow that is driven through the nanopore is via non-faradaic conduction. Two types of ionic flow can be driven through the nanopore-faradaic conduction and non-faradaic conduction. In faradaic conduction, a chemical reaction occurs at the surface of the metal electrode. The faradaic current is the current generated by the reduction or oxidation of some chemical substances at an electrode. The advantage of non-faradaic conduction is that no chemical reaction happens at the surface of the metal electrode.

Figure 22:
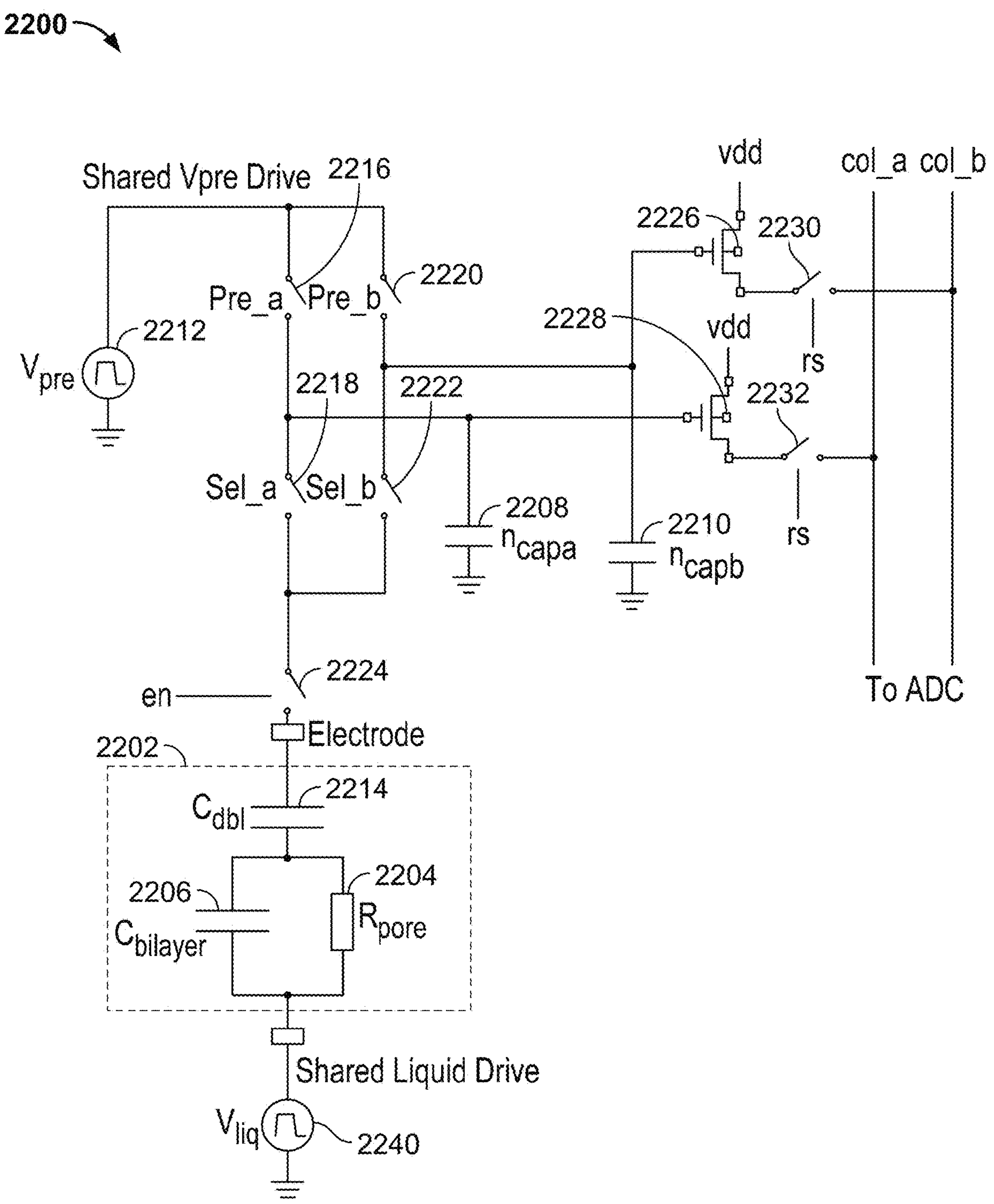
FIG. 22 is a circuit diagram illustrating an embodiment of a circuitry of a cell of a nanopore-based sequencing chip, wherein the sequencing chip includes an analog memory for storing measurement values.

FIG. 22 is a circuit diagram illustrating an embodiment of a circuitry of a cell of a nanopore-based sequencing chip, wherein the sequencing chip includes an analog memory for storing measurement values.

In one approach, a nanopore measurement of an analog circuit value (e.g., voltage, current, resistance, charge, capacitance, time, etc.) may be captured at regular intervals and converted to a digital representation for processing. Often two measurement values are subtracted from each other in order to determine whether a notable event has been detected for the nanopore. In large highly parallel systems with one million cells, outputting values to be subtracted digitally using a processor can be time-consuming and bandwidth limited. In some embodiments, rather than outputting every circuit measurement in a digital form to be stored and digitally processed, at least two measurements are captured for different measurement samples at different times using analog components and subtracted to only digitally output the difference value between the two measurements rather than digitally outputting the absolute values of both of the two measurements. For example, two circuit measurements are stored by two separate capacitors by charging/discharging the capacitors to levels that correspond to the measurements that are subtracted from each other by an analog-to-digital (i.e., ADC) converter to output a digital difference value. In some cases, not only will outputting the difference rather than the absolute values save communication, storage, and digital processing resources, the analog storage and differential measurement of the ADC may be generally less susceptible to injected noise (e.g., from the substrate).

The magnitude of the difference may be utilized to identify events of interest. For example, in the event the difference value is greater than a threshold, the magnitude of the difference value is utilized to identify that a nanopore has been threaded (e.g., open nanopore channel to a tag threaded nanopore) and in the event the difference value is less than the threshold, it is identified that the state of the nanopore remains unchanged (e.g., difference and associated values may be discarded if state difference has not been detected). In some embodiments, the difference value may indicate a change in value resulting from an open nanopore channel on the positive phase of an AC stimulus voltage source to remaining an open nanopore channel on the negative phase of the AC stimulus voltage source. In some embodiments, the difference value may indicate a change in value resulting from an open nanopore channel on the negative phase of an AC stimulus voltage source to a tag threaded nanopore on the positive phase of the AC stimulus voltage source.

Circuit 2200 includes an electrical model 2202 representing the electrical properties of the nanopore and the membrane and capacitor 2214 representing the electrical properties of the working electrode. Electrical model 2202 includes capacitor 2206 that models a capacitance associated with the lipid bilayer ($C_{bilayer}$) and resistor 2204 that models a resistance associated with the nanopore in different states (e.g., the open-channel state or the states corresponding to different types of tags/molecules threaded inside the nanopore). Capacitor 2214 that models a capacitance associated with the working electrode. The capacitance associated with the working electrode is also referred to as a double layer capacitance ($C_{dbl}$).

The rate of the voltage decay (e.g., the steepness of the slope of the applied voltage across the nanopore versus time) across 2202 depends on the resistance of the nanopore (i.e., $R_{pore}$ 2204). As the resistances associated with the nanopore in different states (e.g., the open-channel state, the states corresponding to having different types of tags/molecules inside the nanopore, and the state when the membrane is ruptured) are different due to the molecules'/tags' distinct chemical structures, different corresponding rates of voltage decay may be observed and thus may be used to identify the different states of the nanopore.

Capacitor 2208 and capacitor 2210 each allows the voltage across model capacitors 2206 and 2214 to be effectively captured and stored (e.g., each of capacitor 2208 and capacitor 2210 effectively "integrates" the current flowing through the nanopore) for samples measured at different points in time, in effect creating an analog memory. For example, one voltage sample measurement for one sample measurement is stored in capacitor 2208 and a subsequent sample measurement is stored in capacitor 2210. These stored values may be read out and subtracted to output a difference value rather than (or in addition to) absolute values of both capacitor 2208 and capacitor 2210. Capacitor 2208 and capacitor 2210 may store consecutive sample values or non-consecutive sample values.

A network of switches is utilized to control the preparation, capture, and storage of measurement samples at one or more analog memory capacitors. Switch 2224 may be utilized to connect and disconnect the nanopore and the electrodes from measurement circuitry. For example, switch 2224 is closed after a bilayer is formed and switch 2224 remains open when there is no bilayer (e.g., due to very low impedance when no bilayer is present). When initializing capacitor 2208 to capture a sample measurement, capacitor 2208 is initially precharged. Switch 2216, switch 2218, and switch 2224 are closed while switch 2220 and switch 2222 are open. At this point, capacitor 2208 is charged to the voltage level of voltage source 2212. Then to start the capture, switch 2216 is opened and the charge stored in capacitor 2208 is dissipated by effective model resistor 2204. The rate of voltage decay depends on the value of resistor 2204 (e.g., resistance of nanopore corresponding to the type of tag/molecule inside the nanopore) and the decay may be stopped for capture by also opening switch 2218. At this point, the stored voltage/charge of capacitor 2208 is only subject to minimal decay (e.g., subject to minor charge leakage which may be quantified and/or compensated) and this voltage/charge is effectively stored for later use while another measurement sample is determined and stored in capacitor 2210 using switches 2220 and 2222 while switches 2216 and 2218 remain open. In some embodiments, the measurements stored in capacitor 2208 and capacitor 2210 are consecutive measurement samples. For example, storage of charge/voltage corresponding to the state of the nanopore is toggled between capacitor 2208 and capacitor 2210 for each subsequent sample measurement. In some embodiments, the measurements stored in capacitor 2208 and capacitor 2210 are not consecutive measurement samples. For example, once a measurement is stored in one analog storage capacitor, the subsequent measurement samples are stored and replaced in the other analog storage capacitor until a difference between the charges/voltages stored in the capacitors is greater than a difference threshold value.

The voltage stored in capacitor 2208 may be read out using output circuitry by closing switch 2232 to allow transistor 2228 to output the voltage. The voltage stored in capacitor 2210 may be read out by closing switch 2230 to allow transistor 2226 to output the voltage. The outputted voltage values may be provided to comparison circuitry (e.g., a comparator, an analog-to-digital converter, etc.) that subtracts the outputted voltages. In some embodiments, only the difference value is outputted rather than the absolute/actual output voltage values corresponding to the two different measurement samples. In some embodiments, the difference value and the absolute/actual output voltage values corresponding to the two different measurement samples are outputted. In some embodiments, in the event the difference value is less than a threshold, the difference value is discarded and not outputted.

Circuit 2200 may only show a portion of a circuit of one cell of a plurality of cells of a biochip. In some embodiments, the cells of the biochip are organized in a grid of rows and columns (e.g., each column of cells may output a plurality of column values) and each row of cells is read out substantially simultaneously. The outputs shown in circuit 2200 may represent only two column outputs of a plurality of column values of a row of cells of the biochip being readout. Although the example shown in FIG. 22 shows a circuit designed to store only two voltage values of a nanopore, in other embodiments, the example of FIG. 22 may be extended to allow a circuit to store any number of voltage values of the nanopore by utilizing additional capacitors, switches and output circuitry. The switches shown in FIG. 22 may be any type of switch. Transistor 2226 and 2228 are merely examples and any other type of output circuitry may be utilized to read out electrical values of capacitor 2208 and/or 2210.

In the example shown, voltage source 2240 is an AC voltage source. For example the counter electrode is immersed in the electrolyte above the bilayer and an AC non-Faradaic mode is utilized to modulate a square wave voltage source as $V_{liq}$ 2240. The square wave voltage source may cause the potential of its counter electrode to be at a higher level as compared to the other electrode during the positive phase of the square wave (i.e., dark period of the AC voltage source signal cycle) and at a lower level compared to the other electrode at the negative phase of the square wave (i.e., bright period of the AC voltage source signal cycle). Given this potential difference, capacitor 2208 may be charged during the dark period and discharged during the bright period. Generally during the bright period, the molecule/tag is attracted to be threaded into the nanopore while during the dark period, the molecule/tag is generally repelled away from the nanopore (e.g., causing the nanopore to be in an open-channel state during the dark period). Thus in some embodiments, tag detection is only performed during the bright period when a tag is attracted to the nanopore.

By determining the voltage difference between two different measurement samples, the transition between dark periods and bright periods may be identified (e.g., identify when the difference is greater than a threshold value). Additionally it may take a variable amount of time during the bright period for a tag to be threaded in the nanopore. During the waiting period, while waiting for the nanopore to be threaded, obtained voltage samples may remain relatively constant, representing the open-channel state of the nanopore, and may not be of interest until the nanopore is threaded. By determining a difference between voltage sample measurements and detecting when the difference is within a certain threshold range, nanopore threading may be detected and the magnitude of the difference may indicate the type of molecule/thread of the threading. By utilizing analog memory to determine the difference, processing and storage efficiencies may be gained. In some cases, the threading during the bright period may take place quickly and an open-channel nanopore state may not be detected/sampled during a bright period before detecting the threaded state because the threaded state is achieved prior to the first sampling/measurement of the nanopore during the bight period. In order to detect this quick threading, a difference between a voltage measurement of an open-channel state during a dark period stored in one analog storage capacitor and a voltage measurement of the threaded nanopore state during a subsequent bright period stored in another analog storage capacitor is utilized (e.g., difference is within a specific range) to detect the threaded state and the magnitude of the difference may indicate the type of molecule/thread of the threading.

In an alternative embodiment, Faradaic mode is utilized with a DC voltage source instead of the AC voltage source.

Figure 23:
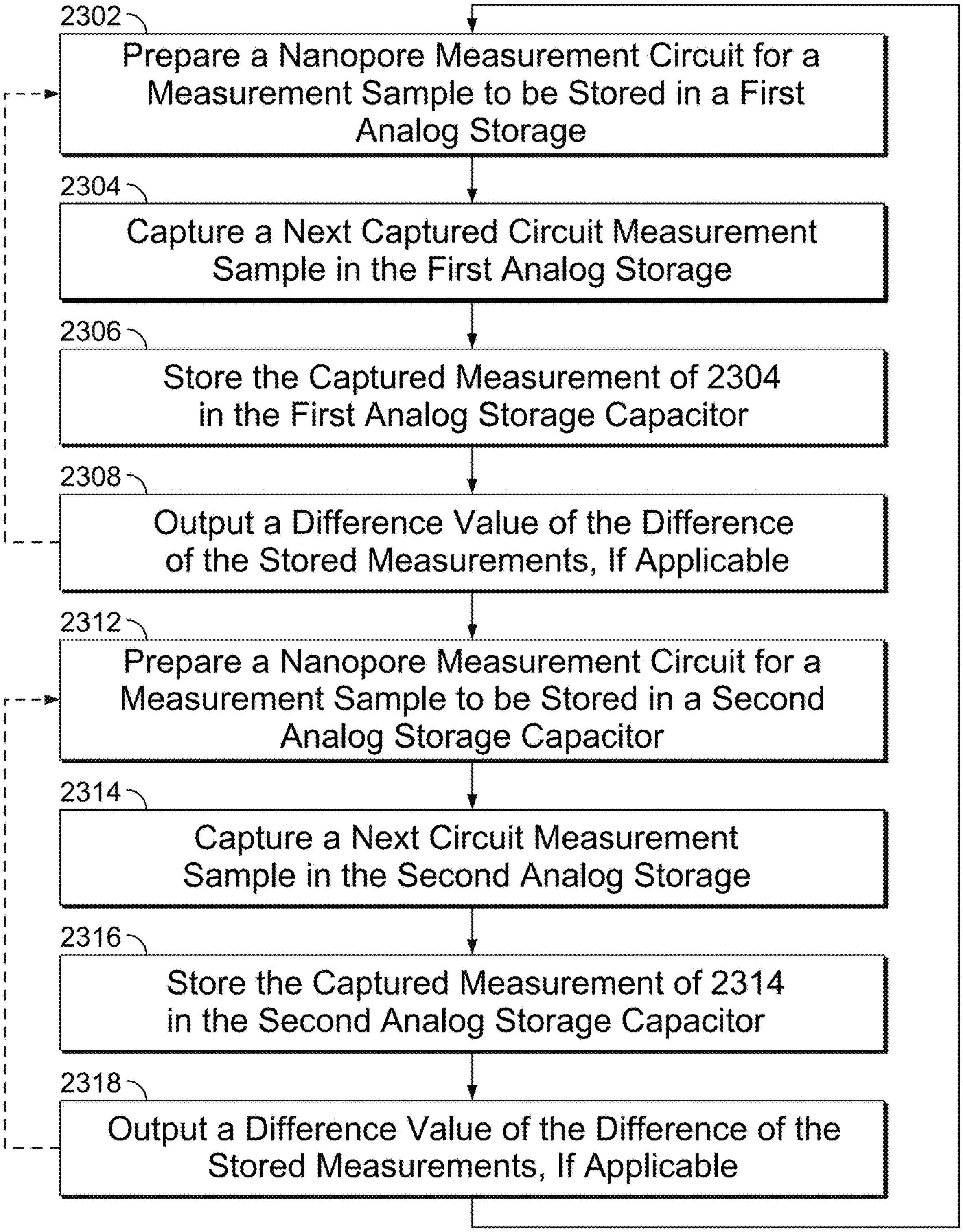
FIG. 23 is a flowchart illustrating an embodiment of a process for measuring a nanopore.

FIG. 23 is a flowchart illustrating an embodiment of a process for measuring a nanopore. The process of FIG. 23 may be implemented on circuit 2200 of FIG. 22. Although the example of FIG. 23 is described using the circuit of FIG. 22, in various embodiments, circuits other than the circuit of FIG. 22 may implement the process of FIG. 23.

As the resistance associated with the nanopore varies according to its different states (e.g., the open-channel state, the states corresponding to having different types of tags/molecules inside the nanopore, the state when the membrane is ruptured, etc.) due to the different molecules/tags inside the nanopore, different corresponding rates of voltage decay may be observed across the nanopore and utilized to identify the different states of the nanopore.

At 2302, a nanopore measurement circuit is prepared for a measurement sample to be stored in a first analog storage. For example, circuit 2200 of FIG. 22 is configured to store a nanopore voltage measurement in analog memory capacitor 2208. In some embodiments, preparing the nanopore measurement circuit includes configuring one or more switches to charge (or discharge) the first analog storage capacitor. For example, switch 2216 is closed (e.g., switch 2220 is left open to not affect capacitor 2210) to charge (or discharge) capacitor 2208 to $V_{pre}$. In some embodiments, voltage is applied across the nanopore by coupling the nanopore to a voltage source. For example, a voltage $V_{pre}$ 2212 is applied to the nanopore by closing switch 2218 as well (e.g., while switch 2216 is also closed) to charge the effective capacitance of model capacitors 2214 and 2206. As the voltage source is connected to the working electrode, the capacitor associated with the membrane is charged and energy is stored in an electric field across the membrane. This initial voltage applied across the nanopore may be $V_{pre}-V_{liquid}$, where $V_{liquid}$ is the voltage of the bulk liquid in contact with the nanopore, where $V_{liquid}$ may be an AC voltage (e.g., square wave voltage source centered around $V_{pre}$). In some embodiments, there exists a switch that connects the nanopore to the nanopore measurement circuit and this switch remains closed in 2302. For example, switch 2224 remains closed after a bilayer is formed and switch 2224 remains open when there is no bilayer (e.g., due to very low impedance when no bilayer is present).

At 2304, a next captured circuit measurement sample is captured in the first analog storage. For example, the first analog storage capacitor is further charged or discharged to capture the next measurement sample of the nanopore. For example, the nanopore is decoupled from a voltage source and the energy stored in the first analog storage capacitor is discharged by the resistance of the nanopore during a bright period of an AC voltage reference of a counter electrode. In another example, the nanopore is decoupled from a voltage source and the energy stored in the first analog storage capacitor is charged by the resistance of the nanopore during a dark period of the AC voltage reference of the counter electrode. The rate of decay or charge of the voltage of the nanopore is associated with the resistance and/or current of the nanopore that is indicative of the state of the molecule/tag that may be inserted in or removed from the nanopore. The resulting charge/energy/voltage of the first analog storage capacitor after a set period of time may identify this state of the nanopore given the known rate of decay/charge associated with each state. The energy/charge/voltage stored in the first analog storage capacitor may serve as the proxy for a measurement of the resistance and/or current of the nanopore. In some embodiments, switch 2216 of FIG. 22 is opened to decouple power source 2212 from capacitor 2208 and the resistance of the nanopore affects the rate of discharging or charging (e.g., due to the phase of the AC voltage reference) of capacitor 2208.

At 2306, the captured measurement of 2304 is stored in the first analog storage capacitor. For example, by allowing the first analog storage capacitor to be dissipated for a set amount of the time, a larger nanopore resistance will dissipate a larger amount of energy/charge/voltage as compared to a smaller resistance in the same amount of time. In another example, the first analog storage capacitor is charged during the lower voltage phases of the AC voltage reference beyond the initial charge in 2302 at a rate based on the resistance of the nanopore. The energy/charge/voltage stored in the first analog storage capacitor may serve as the proxy for a measurement of the resistance/current of the nanopore to identify the state of the nanopore. In some embodiments, in order to preserve and stop the measurement and store the measurement, a switch is opened at a set time. For example, switch 2218 is opened to decouple the nanopore from capacitor 2208 to store the measurement sample in the first analog storage capacitor.

At 2308, a difference value of the difference of the stored measurements is outputted, if applicable. For example, in addition to the measurement voltage stored in the first storage capacitor, a previously stored measurement voltage stored in a second analog storage capacitor (e.g., stored in 2316) is provided to be subtracted. In the event this is the first execution instance of step 2308, step 2308 may be not performed because a measurement has not been stored in the second analog storage capacitor. In some embodiments, providing the difference value includes closing one or more switches to provide measurements of analog storages storing measurement samples to be subtracted. For example, switch 2230 and/or switch 2232 is closed to provide the voltages of capacitor 2208 and/or capacitor 2210 of FIG. 22. In some embodiments, the cells of the biochip are organized in a grid of rows and columns (e.g., each column of cells may output a plurality of column values) and each row of cells is read out substantially simultaneously. The outputs may represent only a portion of a plurality of column values of a row of cells of the biochip being readout. In some embodiments, the stored measurement(s) are compensated for leakage of the analog storage capacitor storing the charge/energy/voltage of the measurement. For example, charge of the analog storage capacitor may naturally dissipate at a low rate due to a limitation of the capacitor size and this leakage is corrected by determining the leakage rate of the capacitor and adding to the voltage output of the capacitor a compensation value that corresponds to the amount of likely leakage based on the determined leakage rate and an amount of time the measurement has been stored by the capacitor. In some embodiments, after the stored measurement(s) have been provided, output switch(es) are opened. For example, switches 2230 and 2232 are opened.

In some embodiments, the provided measurements of the analog storage capacitors are utilized to determine a difference between the measurements. For example, the voltage output of the first analog storage capacitor is subtracted from the voltage output of the second analog storage capacitor. In some embodiments, the provided measurement(s) from the analog storage capacitors are subtracted from each other using one or more of the following: an analog-to-digital converter, a comparator, and any other circuit components. By determining the difference using the output analog values instead of using a digital microprocessor to subtract values that have been converted and stored digitally, efficiency in digital memory storage and digital computation resources may be gained. The difference may be utilized to detect the timing and the degree of change in a status of a nanopore. For example, while the nanopore is periodically sampled, the transition between states of the nanopore may be of importance. To detect these transitions between different states of the nanopore, a difference measurement that is greater than a threshold value may indicate that a change has occurred (e.g., nanopore transition from an open-channel to a state where a tag has been inserted in the nanopore) and the difference value of the change may indicate the exact new state of the nanopore given known difference values expected for different nanopore state transition changes. In some embodiments, the outputted difference value is outputted as a part of an output of a biochip. The outputted difference may indicate no change (e.g., change below threshold) in value between two measurements, a change in nanopore state resulting from a switch from an open nanopore channel to a tag threaded nanopore, a change in phase of an AC reference voltage, or a change in nanopore state resulting from a switch from an open nanopore channel on the negative phase of an AC reference voltage source to a tag threaded nanopore on the positive phase of the AC reference voltage source.

In some embodiments, in the event the difference is below a threshold, the difference value is not outputted. For example, a biochip may be bandwidth limited on the amount of data it is able to output and in order to conserve the amount of data to be outputted from the biochip, an actual difference value is not outputted if the difference value is below a threshold because a change in state of a nanopore has not been detected. In some embodiments, in the event the difference is below a threshold, instead of outputting the actual value of the difference, an indication that the difference value is below a threshold is provided (e.g., indication that state of the nanopore has not changed during a bright period). In some embodiments, in addition to outputting the difference value, the values of the stored measurements of the analog storage capacitors are outputted as well (e.g., digital values of the provided measurements of capacitor 2208 and capacitor 2210 that were utilized to determine the difference value).

In some embodiments, in the event the difference value is below a threshold, the process returns to 2302. For example, rather than continuing the process of FIG. 23 to toggle between storing the sample measurements in different analog storage capacitors, the same analog storage capacitor is utilized to store the next measurement sample. This may reduce switching time between analog storage capacitors and/or allow comparison between two non-consecutive measurement samples if the other analog storage capacitor is storing a previous measurement sample. Nonconsecutive measurement sample comparisons may be allowable because the measurement value remains relatively constant between measurement samples if the state of the nanopore remains constant and the phase of the AC reference voltage source has not changed. In some embodiments, in the event the difference value is below a threshold, the process only returns to 2302 if a second analog storage capacitor is storing a measurement value (e.g., stored in 2316) and a change in phase of the AC reference voltage source has not been detected in 2308.

At 2312, the nanopore measurement circuit is prepared for a measurement sample to be stored in a second analog storage. For example, circuit 2200 of FIG. 22 is configured to store a nanopore voltage measurement in analog memory capacitor 2210. In some embodiments, preparing the nanopore measurement circuit includes configuring one or more switches to charge (or discharge) the second analog storage capacitor. For example, switch 2220 is closed (e.g., switch 2216 is left open to not affect capacitor 2208) to charge (or discharge) capacitor 2210 to $V_{pre}$. In some embodiments, voltage is applied across the nanopore by coupling the nanopore to a voltage source. For example, a voltage $V_{pre}$ 2212 is applied to the nanopore by closing switch 2222 as well (e.g., while switch 2220 is also closed) to charge the effective capacitance of model capacitors 2214 and 2206. As the voltage source is connected to the working electrode, the capacitor associated with the membrane is charged and energy is stored in an electric field across the membrane. This initial voltage applied across the nanopore may be $V_{pre}-V_{liquid}$, where $V_{liquid}$ is the voltage of the bulk liquid in contact with the nanopore, where $V_{liquid}$ may be an AC voltage (e.g., square wave voltage source centered around $V_{pre}$). In some embodiments, there exists a switch that connects the nanopore to the nanopore measurement circuit and this switch remains closed in 2302. For example, switch 2224 remains closed after a bilayer is formed and switch 2224 remains open when there is no bilayer (e.g., due to very low impedance when no bilayer is present).

At 2314, a next circuit measurement sample is captured in the second analog storage. For example, the second analog storage capacitor is further charged or discharged to capture the next measurement sample of the nanopore. For example, the nanopore is decoupled from a voltage source and the energy stored in the second analog storage capacitor is discharged by the resistance of the nanopore during a bright period of an AC voltage reference of a counter electrode. In another example, the nanopore is decoupled from a voltage source and the energy stored in the second analog storage capacitor is charged by the resistance of the nanopore during a dark period of the AC voltage reference of the counter electrode. The rate of decay or charge of the voltage of the nanopore is associated with the resistance and/or current of the nanopore that is indicative of the state of the molecule/tag that may be inserted in or removed from the nanopore. The resulting charge/energy/voltage of the second analog storage capacitor after a set period of time may identify this state of the nanopore given the known rate of decay/charge associated with each state. The energy/charge/voltage stored in the second analog storage capacitor may serve as the proxy for a measurement of the resistance and/or current of the nanopore. In some embodiments, switch 2220 of FIG. 22 is opened to decouple power source 2212 from capacitor 2210 and the resistance of the nanopore affects the rate of discharging or charging (e.g., due to the phase of the AC voltage reference) of capacitor 2208. In some embodiments, in order to capture the measurement sample, a switch is opened at a set time. For example, switch 2222 is opened to decouple the nanopore from capacitor 2210. In some embodiments, the stored voltage of the second analog storage capacitor is the voltage difference across effective capacitors 2214 and 2206. In various embodiments, the set amount of time when the switch is opened to stop the dissipation of the second analog storage capacitor in 2314 is the same as the set amount of time when the switch is opened to stop the dissipation of the first analog storage capacitor in 2306.

At 2316, the captured measurement of 2314 is stored in the second analog storage capacitor. For example, by allowing the second analog storage capacitor to be dissipated for a set amount of the time, a larger nanopore resistance will dissipate a smaller amount of energy/charge/voltage as compared to a smaller resistance in the same amount of time. In another example, the second analog storage capacitor is charged during the lower voltage phases of the AC voltage reference beyond the initial charge in 2312 at a rate based on the resistance of the nanopore. The energy/charge/voltage stored in the second analog storage capacitor may serve as the proxy for a measurement of the resistance/current of the nanopore to identify the state of the nanopore. In some embodiments, in order to preserve and stop the measurement and store the measurement, a switch is opened at a set time. For example, switch 2222 is opened to decouple the nanopore from capacitor 2210 to store the measurement sample in the second analog storage capacitor.

At 2318, a difference value of the difference of the stored measurements is outputted, if applicable. For example, in addition to the measurement voltage stored in the second storage capacitor, a previously stored measurement voltage stored in the first analog storage capacitor (e.g., stored in 2306) are provided to be subtracted. In some embodiments, providing the difference includes closing one or more switches to provide measurements of analog storages storing measurement samples to be subtracted. For example, switch 2230 and/or switch 2232 is closed to provide the voltages of capacitor 2208 and/or capacitor 2210 of FIG. 22. In some embodiments, the cells of the biochip are organized in a grid of rows and columns (e.g., each column of cells may output a plurality of column values) and each row of cells is read out substantially simultaneously. The outputs may represent only a portion of a plurality of column values of a row of cells of the biochip being readout. In some embodiments, the stored measurement(s) are compensated for leakage of the analog storage capacitor storing the charge/energy/voltage of the measurement. For example, charge of the analog storage capacitor may naturally dissipate at a low rate due to a limitation of the capacitor and this leakage is corrected by determining the leakage rate of the capacitor and adding to the voltage output of the capacitor a compensation value that corresponds to the amount of likely leakage based on the determined leakage rate and an amount of time the measurement has been stored by the capacitor. In some embodiments, after the stored measurement(s) have been provided, output switch(es) are opened. For example, switches 2230 and 2232 are opened.

In some embodiments, the provided measurements of the analog storage capacitors are utilized to determine a difference between the measurements. For example, the voltage output of the second analog storage capacitor is subtracted from the voltage output of the first analog storage capacitor. In some embodiments, the provided measurement(s) from the analog storage capacitors are subtracted from each other using one or more of the following: an analog-to-digital converter, a comparator, and any other circuit components. By determining the difference using the output analog values instead of using a digital microprocessor to subtract values that have been converted and stored digitally, efficiency in digital memory storage and digital computation resources may be gained. The difference may be utilized to detect the timing and the degree of change in a status of a nanopore. For example, while the nanopore is periodically sampled, the transition between states of the nanopore may be of importance. To detect these transitions between different states of the nanopore, a difference measurement that is greater than a threshold value may indicate that a change has occurred (e.g., nanopore transition from an open-channel to a state where a tag has been inserted in the nanopore) and the difference value of the change may indicate the exact new state of the nanopore given known difference values expected for different nanopore state transition changes. In some embodiments, the outputted difference value is outputted as a part of an output of a biochip. The outputted difference may indicate no change (e.g., change below threshold) in value between two measurements, a change in nanopore state resulting from a switch from an open nanopore channel to a tag threaded nanopore, a change in phase of an AC reference voltage, or a change in nanopore state resulting from a switch from an open nanopore channel on the negative phase of an AC reference voltage source to a tag threaded nanopore on the positive phase of the AC reference voltage source.

In some embodiments, in the event the difference is below a threshold, the difference value is not outputted. For example, a biochip may be bandwidth limited on the amount of data it is able to output and in order to conserve the amount of data to be outputted from the biochip, an actual difference value is not outputted if the difference value is below a threshold because a change in state of a nanopore has not been detected. In some embodiments, in the event the difference is below a threshold, instead of outputting the actual value of the difference, an indication that the difference value is below a threshold is provided (e.g., indication that state of the nanopore has not changed during a bright period). In some embodiments, in addition to outputting the difference value, the values of the stored measurements of the analog storage capacitors are outputted as well (e.g., digital values of the provided measurements of capacitor 2208 and capacitor 2210 that were utilized to determine the difference value).

In some embodiments, in the event the difference value is below a threshold in 2318, the process returns to 2312. For example, rather than continuing the process of FIG. 23 to toggle between storing the sample measurements in different analog storage capacitors, the same analog storage capacitor is utilized to store the next measurement sample. This may reduce switching time between analog storage capacitors and/or allow comparison between two non-consecutive measurement samples if the other analog storage capacitor is storing a previous measurement sample. Nonconsecutive measurement sample comparisons may be allowable because the measurement value remains relatively constant between measurement samples if the state of the nanopore remains constant and the phase of the AC reference voltage source has not changed. In some embodiments, in the event the difference value is below a threshold, the process only returns to 2312 if a change in phase of the AC reference voltage source has not been detected in 2318.

The process of FIG. 23 is repeated until a stopping criteria is reached. For example, the process of FIG. 23 is stopped after a predetermined amount of time and/or an amount of measurement samples has been outputted. In some embodiments, the process of FIG. 23 is stopped when nanopore measurement is to be stopped. The steps of FIG. 23 may occur at a consistent periodic rate. For example, it is desired to capture measurements of the nanopore at a consistent periodic rate and the steps of FIG. 23 are set at a rate to achieve the desired consistent sampling rate. For example, the timing between step 2306 and/or step 2316 is at a consistent time interval.

Figure 24:
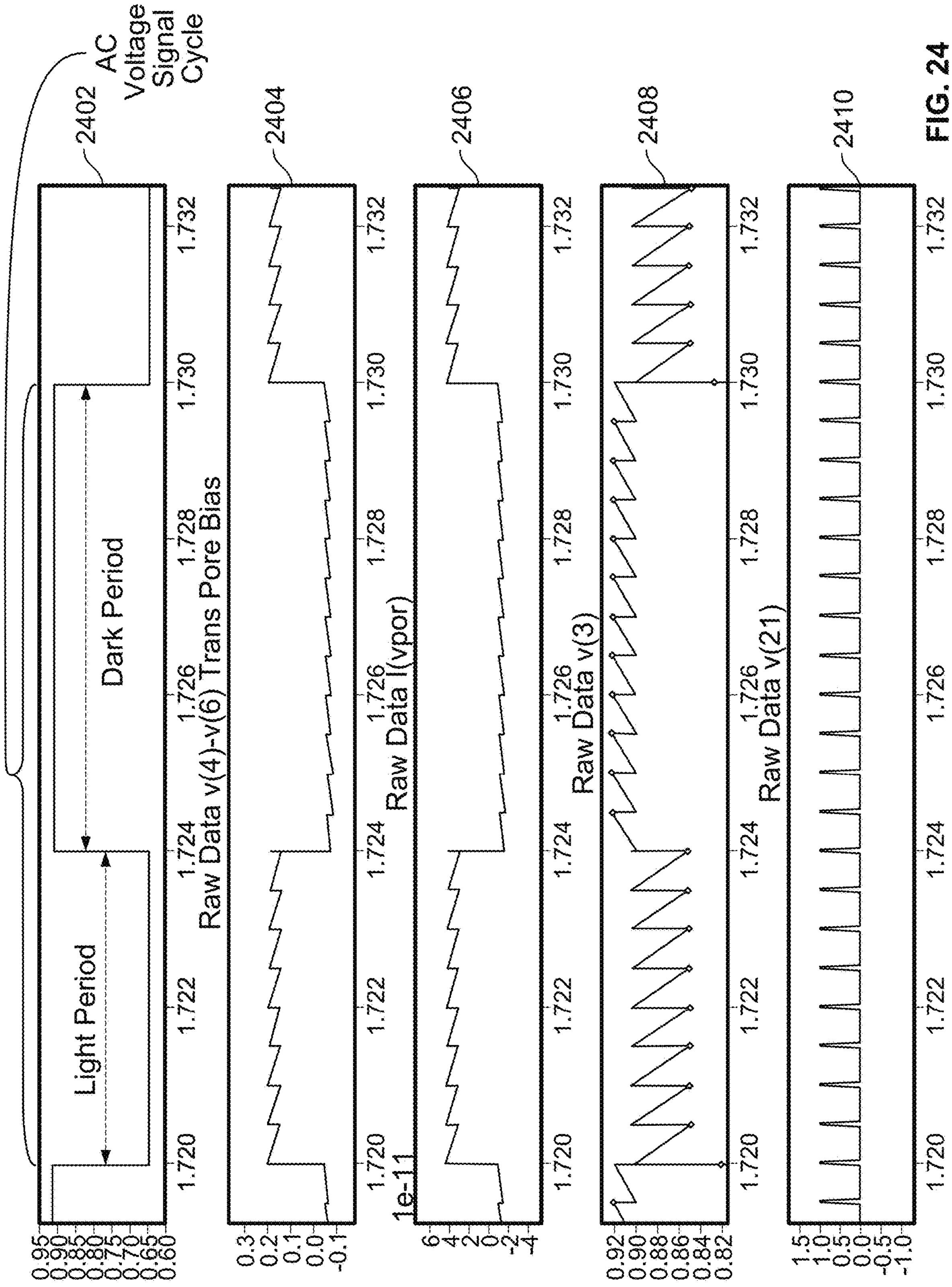
FIG. 24 is a diagram illustrating a graph of circuit measurements when an AC voltage source is utilized as a reference voltage of a counter electrode of a nanopore.

FIG. 24 is a diagram illustrating a graph of circuit measurements when an AC voltage source is utilized as a reference voltage of a counter electrode of a nanopore. For example, a square AC voltage source is utilized as voltage source 2240 of FIG. 22. The graphs of FIG. 24 show graphs prior to introducing tags and consequently the graphs do not show insertion of any tags in the nanopore. The nanopore is effectively in a consistent open-channel state. Graph 2402 shows a graph of an AC voltage source. A square wave voltage source with the labeled bright periods and dark periods is shown. Only a portion of the signals have been shown. Graph 2404 shows the corresponding voltage across the nanopore. For example, the voltage across effective capacitor 2206 and resistor 2204 of FIG. 22 is shown. The "saw tooth" shape of the voltage results from the discharging (during bright periods) and charging (during dark periods) of the capacitance associated with the bilayer of the nanopore for measurement samples during the bright and dark periods. Each "saw tooth" corresponds to each measurement sample that is taken. Graph 2406 shows the corresponding current across the nanopore. For example, current across effective resistor 2204 of FIG. 22 is graphed. Graph 2408 shows the corresponding voltage across an analog storage capacitor. Each "saw tooth" corresponds to each sample measurement that is taken. For example, during the bright period for each measurement sample, the analog storage capacitor is pre-charged to 0.90V and this voltage/charge is dissipated by the resistance of the nanopore until the next pre-charge of the capacitor for the next measurement sample. In this example, during the dark period for each measurement sample, the analog storage capacitor is first pre-charged/dissipated (reset) to 0.90V and this voltage/charge is increased at a rate associated with the resistance of the nanopore until the next pre-charge/reset of the capacitor for the next measurement sample. Graph 2410 shows the corresponding voltage of the pre-charge/dissipation signal.

Figure 25:
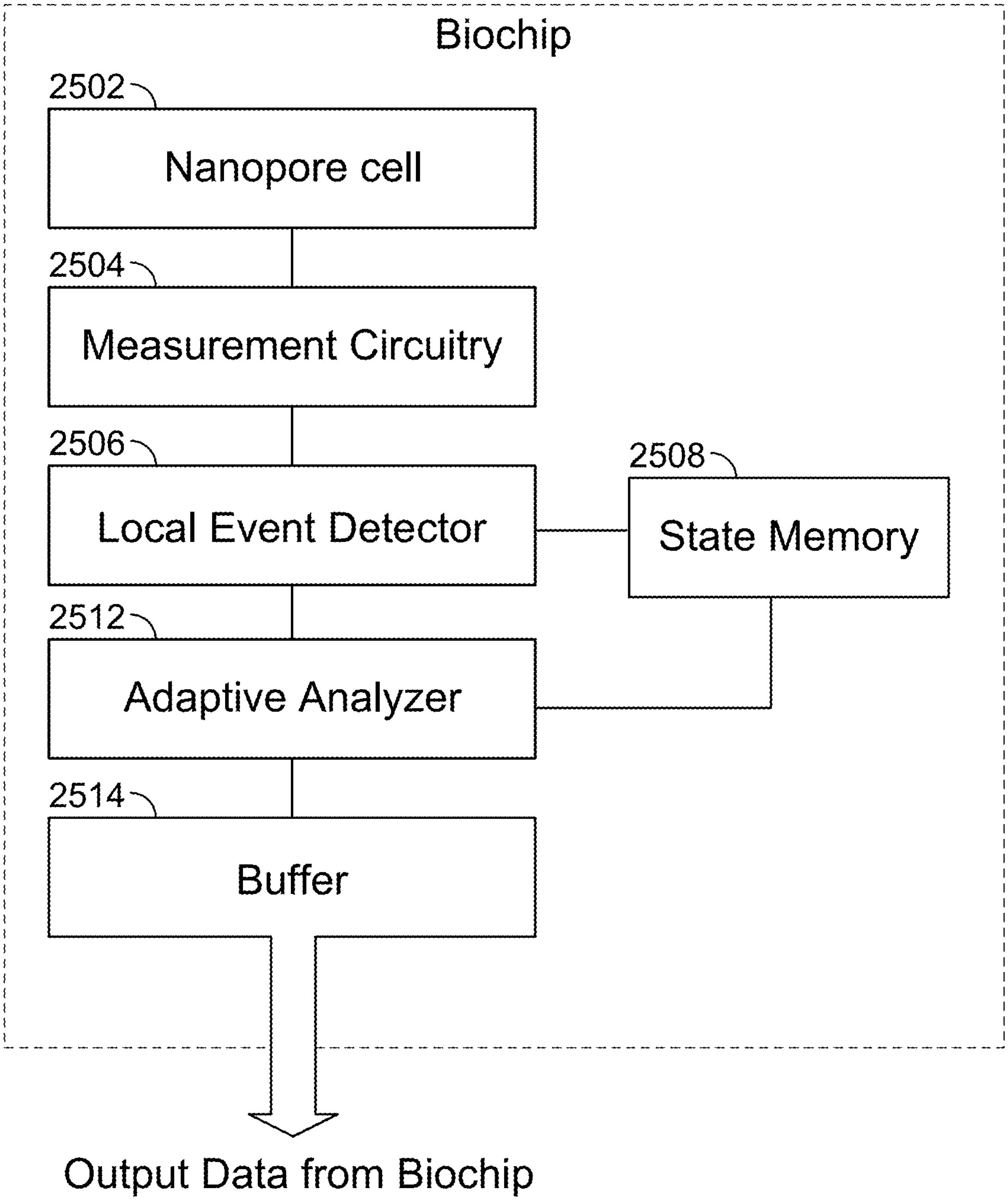
FIG. 25 is a block diagram illustrating an embodiment of a system for detecting a state of a nanopore and adaptively processing nanopore state data to optimize data to be outputted.

FIG. 25 is a block diagram illustrating an embodiment of a system for detecting a state of a nanopore and adaptively processing nanopore state data to optimize data to be outputted. As shown in FIG. 25, the components shown in FIG. 25 are included in a biochip. The biochip may include any number of components shown in FIG. 25. For example, the biochip includes a plurality of nanopore cells, measurement circuitry, and local event detectors connected to adaptive analyzer 2512. The biochip may be a DNA sequencing biochip. For example, data outputted from the biochip from buffer 2514 may be further processed to detect a sequence of nucleotides included in a DNA. Any of the components shown in FIG. 25 may be implemented using any number of one or more of the following: a circuit, a circuit component, an electrical component, a circuit module, a processor, a comparator, a computing module, a memory, a storage, a microarray, and a biochip component.

In some embodiments, the system shown in FIG. 25 is utilized to reduce and manage data to be outputted from a biochip of nanopore cells. For example, the amount of data that can be outputted by a DNA sequencing biochip may be limited by the maximum output data rate of the biochip. With a large number of cells on the biochip, the amount of data that can be potentially outputted by the biochip may exceed the maximum output data rate of the biochip. In some embodiments, the type and amount of data to be outputted is managed in a dynamic manner that dynamically reduces the amount of data to be outputted when required. For example, given processing cost of compressing and decompressing data, the information to be outputted may be only compressed if needed because the amount of current data to be outputted by the biochip exceeds a threshold. In another example, when an event is detected on a cell of the biochip, related information to be outputted may be discarded and not outputted if the information can be outputted later without loss of information. In another example, when an event is detected on a cell of the biochip, related information to be outputted may be discarded and not outputted, even if the information cannot be outputted later without loss of information.

Nanopore cell 2502 is connected to measurement circuitry 2504. Nanopore cell 2502 may be nanopore cell 100 of FIG. 1, cell 200 of FIG. 2, and/or include any nanopore described in the specification. In some embodiments, nanopore cell 2502 may be electronically modeled as 1602 of FIG. 16, 1702 of FIG. 17, 1802 of FIGS. 18A and 18B and/or 2202 of FIG. 22.

Measurement circuitry 2504 detects electrical measurements of nanopore cell 2502. The electrical measurements may be utilized to detect the state of the nanopore of nanopore cell 2502. For example, a change in voltage measured by measurement circuitry 2504 indicates whether and which tag has been threaded in the nanopore. Examples of measurement circuitry 2504 include 1600 of FIG. 16, 1700 of FIG. 17, 1800 of FIG. 18A, 1801 of FIG. 18B, or 2200 of FIG. 22.

Local event detector 2506 receives detected electrical measurements from measurement circuitry 2504. In some embodiments, local event detector 2506 detects whether electrical measurements from measurement circuitry 2504 indicate a nanopore state change. For example, electrical measurement values are utilized to determine the type of tag inserted in a nanopore and only may be of importance when a tag enters the nanopore. If it is known that the state of the nanopore has not changed, the actual measurement value may not be of importance.

In some embodiments, rather than outputting from a biochip electrical measurement values for every periodic electrical measurement sample, measurement values are only outputted when required (e.g., when a state change of the nanopore to a threaded state has been detected). In the event it is detected that a state change is not indicted by a particular measurement sample, an indication that the state has not changed may be reported rather than reporting the actual measurement sample value. In some embodiments, by determining a difference in the electrical measurement values from a previous measurement sample (e.g., stored measurement sample value corresponding to an open-channel state of nanopore) to a new measurement sample, the magnitude of the difference may indicate whether a state change has occurred (e.g., difference is greater than threshold, within a certain range, etc.) and which tag has been inserted in the nanopore. In some embodiments, a baseline expected electrical measurement of an open-channel nanopore is determined/known and utilized to compare with a newly received electrical measurement sample to determine whether the new electrical measurement sample indicates that a tag has been inserted or removed from the nanopore.

In some embodiments, state memory 2508 stores one or more previously received electrical measurement samples from measurement circuitry 2504. For example, a previously received electrical measurement sample value retrieved from state memory 2508 is utilized by local event detector 2506 in determining whether a newly received electrical measurement sample value indicates a change in state. In some embodiments, state memory 2508 stores one or more reference measurement values corresponding to one or more nanopore states (e.g., measurement values corresponding to an open-channel state of a nanopore).

In some embodiments, state memory 2508 stores an identifier of whether an insertion of a tag in a nanopore has been reported by local event detector 2506 for a current bright period of a reference AC voltage source signal period. For example, once an electrical measurement sample value corresponding to an insertion of a tag in a nanopore has been detected and reported once for the same event during the same bright period of a reference AC voltage source signal cycle, subsequent electrical measurement samples obtained while the tag is still inserted in the nanopore may not need to be reported again because the state change has been already reported along with the associated electrical measurement value that indicates the type of tag inserted in the nanopore. Thus, in the event the stored identifier indicates that the tag inserted state has been already reported by local event detector 2506 for the current bright period of the current reference AC voltage source signal cycle, a subsequently received electrical measurement value that also corresponds to the same tag inserted state does not need to be reported. This stored identifier may be reset for every new cycle of the reference AC voltage source signal.

Adaptive analyzer 2512 receives data to be outputted (e.g., from a biochip for further processing/detection) from local event detector 2506. In some embodiments, adaptive analyzer 2512 receives data from a plurality of local event detectors. For example, each local event detector of each nanopore cell detects and reports a state change of each respective nanopore cell and adaptive analyzer 2512 gathers the reported data from all local event detectors of a biochip to analyze the data to be outputted in an attempt to reduce the size of the data to be outputted, if needed. In some embodiments, adaptive analyzer 2512 is periodically provided data as electrical measurements of nanopore cells are obtained periodically.

For example, a bit vector indicating whether a state change has been detected for each nanopore of the biochip is generated for output (e.g., each bit of the vector corresponds to a different nanopore cell and indicates whether a tag has been inserted in the respective nanopore) for each periodic measurement instance. Along with the bit vector, for any nanopore that has been detected to have changed into a tag inserted state, a corresponding electrical measurement sample value (e.g., value corresponding to a certain type of tag) is selected for output. Adaptive analyzer 2512 places data to be outputted (e.g., from a biochip) in buffer 2514.

Buffer 2514 stores data to be outputted from the biochip. Data may be continually outputted from the biochip from buffer 2514 at a data output rate. However, the amount of data generated to be outputted may vary over time (e.g., depending on when a tag is inserted in a nanopore) and may, at times, exceed the data output rate. Buffer 2514 stores data waiting to be outputted. Depending on the amount of data in buffer 2514, adaptive analyzer 2512 adaptively attempts to reduce the size of new data to be placed in buffer 2514 for output. For example, if buffer 2514 is relatively empty, adaptive analyzer 2512 does not compress data before placing data in buffer 2514 to save computing resources required to compress data whereas if buffer 2514 is at a threshold fill level, adaptive analyzer 2512 compresses data before placing data to be outputted in buffer 2514. In some embodiments, buffer 2514 adaptively selects a compression technique (e.g., compression algorithms) and/or compression setting (e.g., compression table symbols) based on characteristics (e.g., entropy) of the data to be compressed.

In some embodiments, in the event adaptive analyzer 2512 is unable to reduce/compress (e.g., using lossless compression) the data to a desired size, adaptive analyzer 2512 selectively modifies data to be outputted if no loss in functionality/information will ultimately result. For example, reporting of an insertion of a tag in a nanopore may be delayed without negative consequences (e.g., tag is inserted in nanopore for multiple measurement cycles) and data reporting insertion of the tag and its associated measurement data is dropped to allow it be reported for a next electrical measurement sample cycle. This may be achieved by resetting (by adaptive analyzer 2512) the indicator stored in state memory 2508 that indicates whether a tag inserted state measurement value has been reported for a current bright period of a current reference AC voltage source signal cycle-allowing the next measurement sample value of the nanopore to be reported during the same bright period because a previous measurement sample value indicating the tag inserted state was previously reported and dropped by adaptive analyzer 2512. In some embodiments, adaptive analyzer 2512 drops a portion of data to be reported (e.g., randomly selected portion, using lossy compression, etc.) in order to meet a desired size/bandwidth of data to be outputted.

In an alternative embodiment, one or more components shown in FIG. 25 may be included in one or more other chips that is separate from the biochip. For example, the biochip includes nanopore cell 2502 and a separate companion chip in communication with the biochip includes one or more of the other components shown in FIG. 25.

Figure 26:
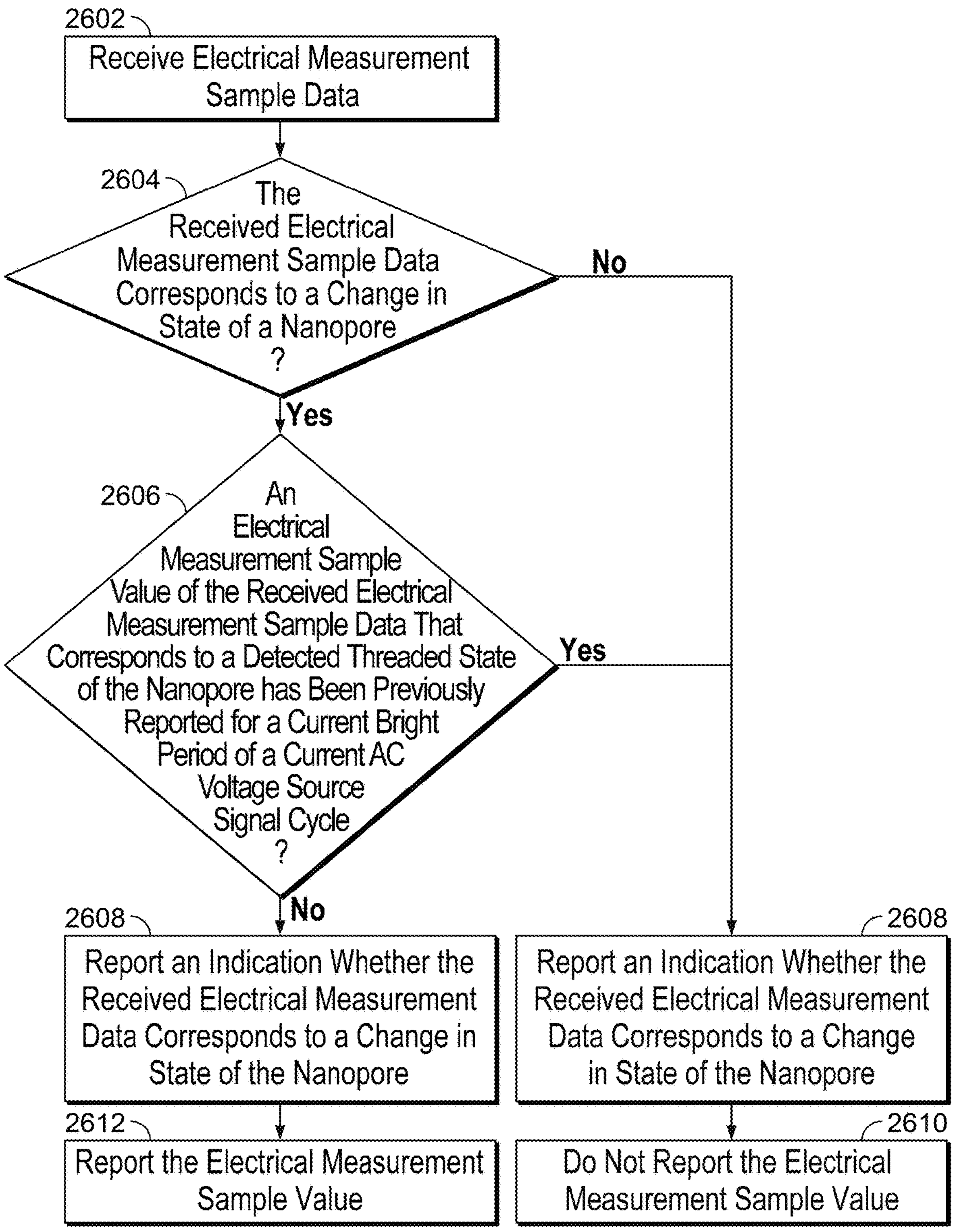
FIG. 26 is a flowchart illustrating an embodiment of a process for reporting nanopore state data.

FIG. 26 is a flowchart illustrating an embodiment of a process for reporting nanopore state data. The process of FIG. 26 may be implemented on local event detector 2506 of FIG. 25. For example, the process of FIG. 26 is implemented on each of a plurality of local event detectors of nanopore cells of a biochip.

At 2602, electrical measurement sample data of a nanopore is received. For example, a voltage measurement value corresponding to a resistance of the nanopore is received. In some embodiments, the electrical measurement sample data includes an electrical measurement sample value (e.g., numerical value) received from measurement circuitry 2504 of FIG. 25. The received electrical measurement data may correspond to one measurement sample of periodic measurement samples received. In some embodiments, the electrical measurement sample data is a value of an amount of charge/voltage stored in an analog storage capacitor (e.g., analog storage capacitor of FIG. 22). In some embodiments, the electrical measurement sample data is a difference value provided in 2308 or 2318 of FIG. 23. Examples of the electrical measurement sample include one or more of the following: a voltage value, a current value, a resistance value, an amount of charge value, a capacitance value or a time value.

At 2604, it is determined whether the received electrical measurement data corresponds to a change in state of the nanopore (e.g., change in state to a threaded state, a change from a previously detected state, etc.). For example, the received electrical measurement sample data is analyzed to determine whether the received electrical measurement data corresponds to a change in state of the nanopore. In some embodiments, determining whether the received electrical measurement data corresponds to the change in nanopore state includes comparing the received electrical measurement data to a previously received electrical measurement data. For example, a difference between a previously received electrical measurement value and an electrical measurement value received in 2604 is calculated and utilized to determine whether the difference value indicates a nanopore state change (e.g., difference is within a predefined range, greater than a minimum threshold (e.g., not due to minor variation/noise), less than a maximum threshold (e.g., not due to change between bright period and dark period), etc.). In some embodiments, the received electrical measurement data is the difference between a previous electrical measurement data sample and a subsequently captured electrical measurement data sample. In some embodiments, determining whether the received electrical measurement data corresponds to the change in nanopore state includes comparing the received electrical measurement data to a reference electrical measurement data. For example, a reference electrical measurement data (e.g., predefined or a previously received measurement data sample) that corresponds to an open-channel nanopore state is compared with the received electrical measurement data to determine whether the electrical measurement data corresponds to a change in nanopore state to a tag threaded state.

In some embodiments, determining whether the received electrical measurement data corresponds to the change in nanopore state includes determining whether the received electrical measurement data corresponds to a threaded state. For example, the threaded state during a bright period of a reference AC voltage source signal cycle is of interest and is desired to be detected to sequence a DNA. In some embodiments, only a nanopore state change during a bright period of a reference AC voltage source signal cycle is configured to be detected. For example, during a dark period, a state change identifier and/or an electrical measurement sample value is not outputted by a local event detector. In some embodiments, in the event the received electrical measurement data corresponds to a dark period of the current cycle of the reference AC voltage source signal, nanopore state change detection is not performed. For example, during the dark period it is automatically determined that a nanopore state change has not been detected.

In some embodiments, determining whether the received electrical measurement data corresponds to a change in state of the nanopore includes determining whether the new nanopore state has been maintained. For example, once a tag is inserted in the nanopore during a bright period of an AC voltage source signal cycle, the tag is expected to stay inside the nanopore until the dark period of the AC voltage source signal cycle under certain sampling conditions (e.g., when the electrical modulation of bright/dark AC voltage source signal is fast compared to the speed of the biological event). In this example, in the event the state of the nanopore changes from an open-channel state to a threaded state then back to the open-channel state during a single bright period prior to the end of the bright period, a statistically not representative event has likely occurred (e.g., detection of the threaded state may be due to signal noise or a tag was not properly threaded). Thus when a change in nanopore state from a threaded state to an open-channel state is detected prior to the end of the current bright period, the threaded state change may or may not be reported based on the sampling condition. For example, the earlier detected nanopore state change to the threaded state for the current bright period may be dropped/prevented from being further processed and/or outputted from the biochip under certain sampling conditions.

If at 2604 it is determined that the received electrical measurement data does not correspond to a change in nanopore state, the process proceeds to 2608. If at 2604 it is determined that the received electrical measurement data corresponds to a change in nanopore state, at 2606, it is determined whether an electrical measurement sample value of the received electrical measurement sample data that corresponds to a detected threaded state of the nanopore has been previously reported for a current bright period of a current AC voltage source signal cycle. For example, the electrical measurement sample value that corresponds to the same threaded state is to be only reported once rather than every time a measurement sample of the tag threaded nanopore is obtained to avoid duplicate information from being reported (e.g., measurement value is to be reported only once per single tag threaded event). In some embodiments, the stored report status identifier (e.g., stored in state memory 2508 of FIG. 25) tracks whether an electrical measurement value that corresponds to a threaded state has been already reported (e.g., reported to adaptive analyzer 2512) for a current bright period of a current cycle of a reference AC voltage source signal of a nanopore cell. In some embodiments, at 2608, the stored report status identifier is obtained to determine whether the report status identifier indicates that an electrical measurement sample value that corresponds to a detected threaded state of the nanopore has been already reported. If the report status identifier indicates that a previous electrical measurement sample value has been already reported, a subsequent electrical measurement sample value corresponding to the same threaded nanopore state may not need to be reported. This stored report status identifier may be reset for every new cycle of the reference AC voltage source signal. In some embodiments, the stored report status identifier is reset to allow a second reporting of an electrical measurement value for the same threaded nanopore state in the event a previous reported electrical measurement value was discarded from being outputted to delay reporting the electrical measurement value of the threaded nanopore state.

At 2608, an indication of whether the received electrical measurement data corresponds to a change in state of the nanopore is reported. For example, for the received measurement sample data, a binary bit that indicates whether the received measurement data indicates a threaded nanopore state during a bright period of a cycle of a reference AC voltage source signal is reported (e.g., provided to adaptive analyzer 2512). In this example, a value of "1" is reported if the received electrical measurement data corresponds to a nanopore threaded state and a value of "0" is reported otherwise. In some embodiments, no data is reported if the received electrical measurement data does not correspond to a change in nanopore state. In some embodiments, no data is reported during a dark period of a cycle of a reference AC voltage source signal. In some embodiments, the indication indicates whether the received electrical measurement data corresponds to a change in state from a threaded state to an open-channel state. In some embodiments, the recipient of the indication combines together each binary bit indication from each nanopore cell of a biochip to generate a bit array (e.g., bitmap, bitset, bit string, bit vector, etc.) representation of the nanopore states of the cells. In some embodiments, the indication indicates whether a received electrical measurement sample value will be reported (e.g., indication corresponds to determination of 2606). For example, a received electrical measurement sample value is only reported when it is detected that the received electrical measurement sample value indicates a threaded nanopore state during a bright period and a previous measurement value for this threaded nanopore state has not been already reported (e.g., as indicated by the stored report status indicator).

If at 2606 it is determined that a previous electrical measurement sample value has been previously reported, at 2610, the electrical measurement sample value of the received electrical measurement data is not reported (e.g., not provided to adaptive analyzer 2512). If at 2606 it is determined that a previous electrical measurement sample value has not been previously reported, at 2612, the electrical measurement sample value of the received electrical measurement is reported (e.g., provided to adaptive analyzer 2512).

The process of FIG. 26 is repeated for each received measurement sample. In some embodiments, the process of FIG. 26 is only performed while a bilayer and a nanopore are present in a cell of the biochip.

Figure 27:
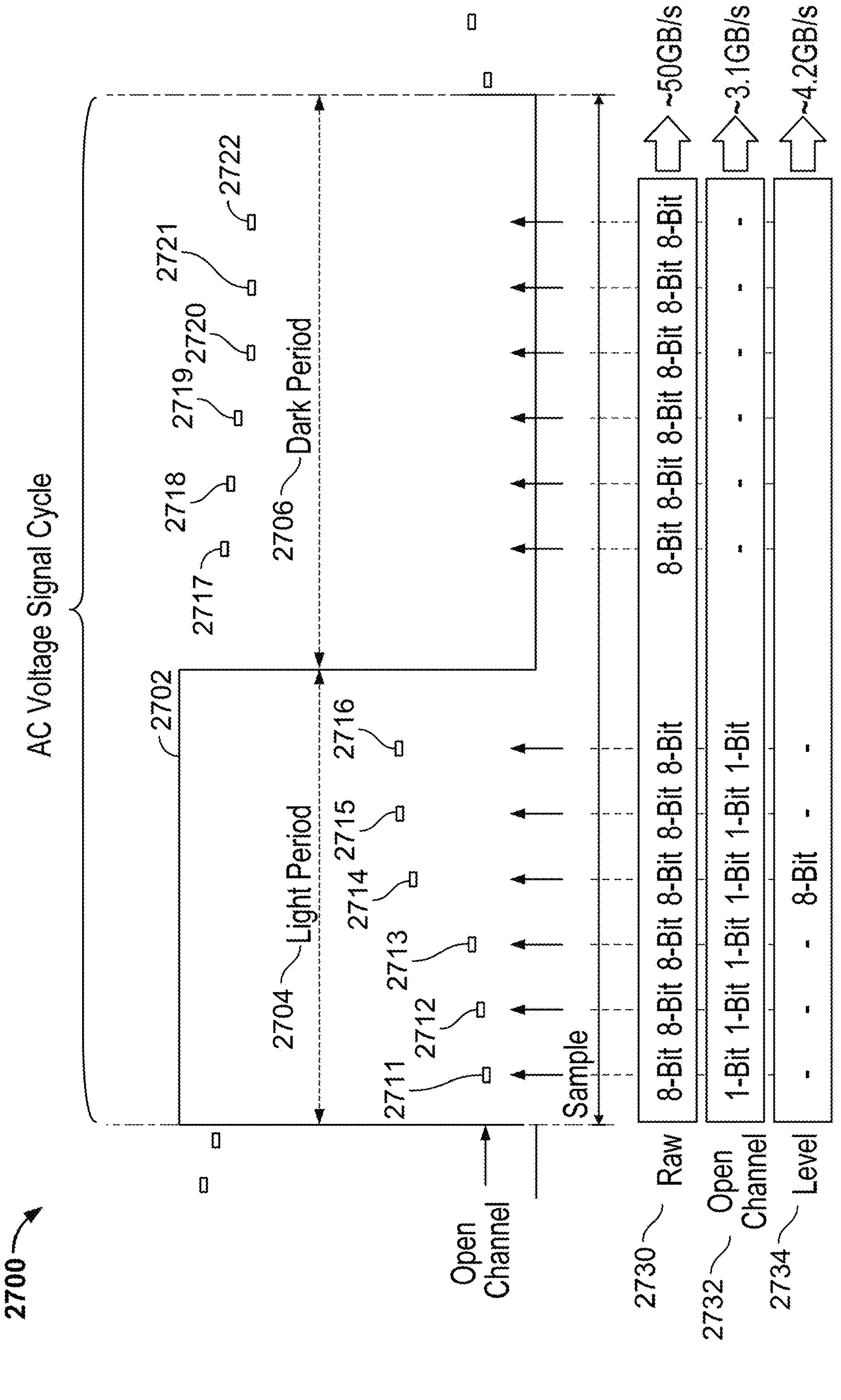
FIG. 27 is a diagram illustrating an example of periodic electrical measurement samples received during a cycle of a reference AC voltage source signal.

FIG. 27 is a diagram illustrating an example of periodic electrical measurement samples received during a cycle of a reference AC voltage source signal. Graph 2700 shows a graphical representation of a square wave AC voltage source signal 2702 (e.g., signal of voltage source 2240 of FIG. 22). The shown cycle of signal 2702 includes bright period 2704 (e.g., when polarity encourages a tag to be threaded in a nanopore) and dark period 2706 (e.g., when polarity encourages a tag to exit the nanopore). Electrical measurement samples 2711-2722 each correspond to an electrical measurement sample that is sequentially received as each electrical measurement sample is detected at a periodic interval (e.g., received in 2602). In some embodiments, the electrical measurement samples correspond to nanopore measurement voltage output of 1600 of FIG. 16, 1700 of FIG. 17, 1800 of FIG. 18A, 1801 of FIG. 18B, or 2200 of FIG. 22.

Measurement samples 2711-2713 correspond to an open-channel nanopore state. When a tag becomes threaded in the nanopore, the measurement value changes and is shown as an elevated voltage in measurement samples 2714-2716. The detection of measurement samples 2714-2716 as the threaded state of the nanopore may be of interest when attempting to detect the type of tag threaded in the nanopore. Because the measurement sample values while the tag is threaded are similar (e.g., values of measurement samples 2714-2716 are similar), only reporting of one of these values may be necessary to detect the type of the tag. For example, if the value of measurement sample 2714 is reported, values of samples 2715 and 2716 do not need to be reported. However, if measurement sample 2714 is determined to be not outputted to reduce the amount of data to be outputted at a particular point in time, the values of samples 2715 or 2716 may be reported later without loss in the ability to detect the tag threaded state and the type of tag threaded in the nanopore during the current bright period. Because a tag is repelled from the nanopore during the dark period (e.g., while samples 2717-2722 are measured), measurement samples of the dark period are often not of interest and may not need to be reported.

In the example shown, traditionally by reporting every raw electrical measurement sample value (e.g., 8-bit value representing measurement value reported for each sample), a large amount of output data bandwidth (e.g., 50 GB/s) would be required for a biochip (example output 2730). However, the amount of data to be outputted may be drastically reduced by only reporting the electrical measurement value when meaningful and necessary. Rather than reporting the raw electrical measurement sample value for each sample, a binary indication is provided for each measurement sample (example output 2732). The binary indication indicates whether the measurement sample corresponds to a nanopore state change (e.g., indicates whether open-channel state or threaded state during a bright period). During the dark period, the binary indication may not need to be provided. In addition to example output 2732, when necessary, the actual measurement sample value is reported (example output 2734). For example, the first time the nanopore state change to a threaded state is detected, the corresponding measurement sample value is reported to allow identification of the tag that corresponds to the measurement sample value. As compared to the traditional raw reporting (example output 2730), the reporting of binary indications (example output 2732) and selective measurement value reporting (example output 2734) significantly reduces the output data bandwidth requirement (e.g., reduction from 50 GB/s to 7.3 GB/s (i.e., combination of 3.1 GB/s+4.2 GB/s)).

Figure 28:
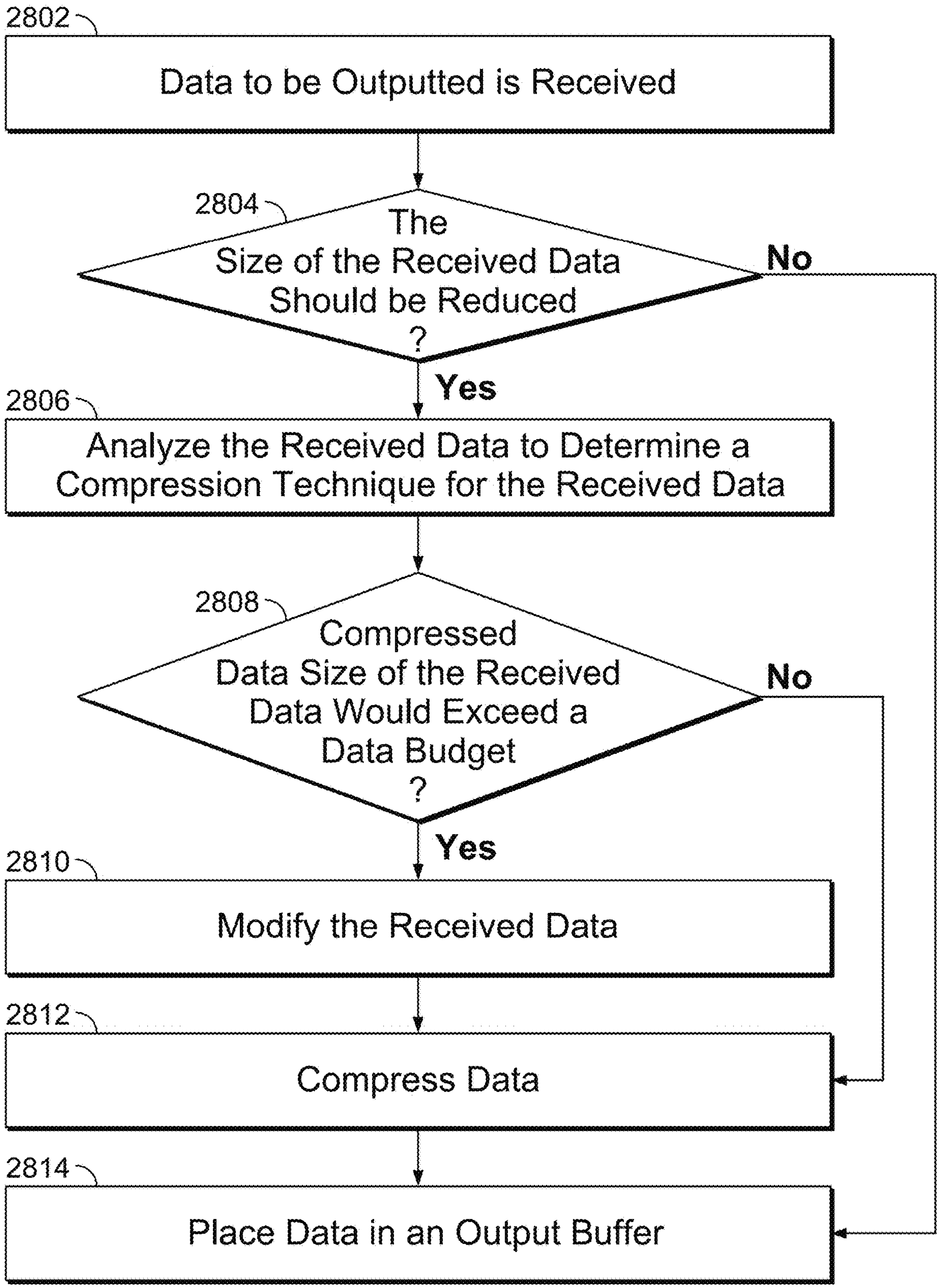
FIG. 28 is a flowchart illustrating an embodiment of a process for adaptively analyzing data to be outputted.

FIG. 28 is a flowchart illustrating an embodiment of a process for adaptively analyzing data to be outputted. The process of FIG. 28 may be implemented on adaptive analyzer 2512 of FIG. 25. In some embodiments, the process of FIG. 28 is repeated for each set of data received to be outputted.

At 2802, data to be outputted is received. The received data may include data indicating whether a nanopore state changed is received for each nanopore cell of a group of nanopore cells. For example, there exists a plurality of nanopore cells on a biochip and for each nanopore cell and for each instance when electrical measurement samples of the nanopore cells are taken, a one bit identifier indicating the nanopore state of the nanopore cell is received. In some embodiments, rather than utilizing the one bit identifier, a multiple bit identifier indicating the nanopore state of the nanopore cell is received. In some embodiments, at a periodic interval, electrical measurement samples of all nanopores are all obtained together as a group and the plurality of one bit identifiers corresponding to each group of electrical measurements are concatenated together to form a bit array (e.g., bitmap, bitset, bit string, bit vector, etc.) indicating the states of the nanopore cells. Each element position of the bit array may correspond to the same nanopore cell for each subsequent bitmap that is generated for the corresponding subsequent sets of measurement samples. In some embodiments, the received data includes the data reported at 2608 and/or 2612 of FIG. 26. For example, data reported using the process of FIG. 26 is provided by local event detector 2506 of FIG. 25 for each nanopore cell of a biochip.

In some embodiments, the received data includes an electrical measurement sample value corresponding to a detected change in the state of a nanopore. For example, in the event a threaded state has been detected for a nanopore and its corresponding electrical measurement value has not been already reported (e.g., as indicated by a state report indicator stored in state memory 2508 of FIG. 25), the received data includes the corresponding electrical measurement sample value that can be utilized to determine the type of tag inserted in the nanopore. In some embodiments, the one bit identifier corresponding to a nanopore indicates whether a corresponding electrical measurement sample value of the nanopore will be included in the received data. In some embodiments, the received data includes the measurement sample value reported in 2612 of FIG. 26.

At 2804, it is determined whether the size of the received data should be reduced. For example, the output data rate of a biochip is limited and it is determined whether the amount of additional data to be outputted by the biochip should be reduced because a data budget has been exceeded. One example of reducing the size of the received data includes compressing the data. However, by not compressing the data when not needed, the amount of computing resources required to compress and decompress data may be saved. In some embodiments, determining whether the size of the received data should be reduced includes determining the amount of data remaining in a buffer to be outputted. For example, buffer 2514 of FIG. 25 stores data awaiting to be outputted by a biochip and as output bandwidth is available, data from the buffer is outputted from the biochip and removed from the buffer. In some embodiments, determining whether the size of the received data should be reduced includes determining whether the amount of data remaining in the output buffer has reached a threshold level/amount. In the event the threshold level has been reached, it is determined that the size of the received data to be outputted should be reduced and otherwise it is determined that the size of the received data does not need to be reduced. In some embodiments, determining whether the size of the received data should be reduced includes determining whether adding the received data to the output buffer would result in increasing the amount of data in the buffer beyond a threshold level/amount. In some embodiments, determining whether the size of the received data should be reduced includes determining whether the size of the received data is beyond a threshold and in the event the size is beyond the threshold, the received data is to be reduced. In some embodiments, determining whether the size of the received data should be reduced includes determining whether the received data should be compressed.

If at 2804 it is determined that the received data is to be reduced, at 2806, the received data is analyzed to determine a compression technique for the received data. For example, a compression technique is selected among a plurality of techniques based on a profile and/or contents of the received data. In some embodiments, the compression technique is non-lossy. For example, at least a portion of the received data is not required to be modified or lost when compressing the received data. In some embodiments, step 2804 is not performed. For example, step 2806 is always performed when the process of FIG. 28 is performed.

At 2808, it is determined whether a compressed data size of the received data would exceed a data budget. For example, a size of the received data that would result after applying the selected compression technique is determined. Determining whether the data budget would be exceeded may include determining whether adding compressed received data to an output buffer would result in increasing the amount of data in the buffer beyond a threshold level/amount. For example, in the event adding the compressed data would result in overfilling the buffer, it is determined that the data budget would be exceeded. In some embodiments, determining whether the data budget would be exceeded includes determining whether the size of the compressed received data is larger than a threshold. For example, the size of the compressed received data is compared to a maximum data size or amount of capacity remaining in an output buffer.

If at 2808, it is determined that the compressed data size would exceed the data budget, at 2810, the received data is modified. In some embodiments, modifying the received data includes filtering the received data. In some embodiments, modifying the received data includes modifying contents of the compressed data to delay reporting of an electrical measurement sample value corresponding to a threaded state of a nanopore. For example, in the event an electrical measurement sample value of a threaded nanopore state is able to be reported for any of a plurality of electrical measurement samples obtained during the threaded state of a nanopore, an electrical measurement sample value of one of the electrical measurement samples may be dropped and not reported because an electrical measurement sample value of a subsequent electrical measurement sample may be reported instead. In some embodiments, modifying the received data includes removing an electrical measurement sample value from the received data and indicating a subsequent electrical measurement sample value corresponding to a threaded nanopore state should be reported for output. For example, a status report identifier (e.g., status report identifier stored in state memory 2508) that identifies whether an electrical measurement sample value of a threaded state of a nanopore has been already reported for a current bright period of a current reference AC voltage source signal cycle is reset to enable reporting of a subsequent measurement sample value indicating the threaded state.

In some embodiments, modifying the received data includes selecting a lossy compression technique to be utilized. For example, in the event the data budget has been/will be exceeded yet a measurement sample value is unable to be removed/delayed from being outputted, the received data is to be compressed using a lossy compression technique to further reduce its size. In some embodiments, a portion of the received data is dropped (e.g., to introduce random noise, to reduce data precision, etc.). For example, in the event other modification technique(s) are unable to reduce the data to not exceed the data budget, a random portion of the received data is selected to be not outputted. In some embodiments, the determination in 2808 is optional.

For example, step 2810 is always performed when the process of FIG. 28 is performed.

At 2812, the received data, whether modified (e.g., at 2810) or not modified (e.g., determined to not exceed data budget in 2808), is compressed. For example, the data is compressed using the selected compression technique (e.g., non-lossy or lossy).

At 2814, the resulting received data, whether compressed (e.g., at 2812) or not compressed (e.g., determined not to be reduced in 2804), is placed in an output buffer to be outputted. For example, data is inserted in buffer 2514 of FIG. 25 for output from a biochip. In an alternative embodiment, the resulting received data, whether uncompressed or compressed, is outputted from a biochip without being placed in an output buffer.

Figure 29:
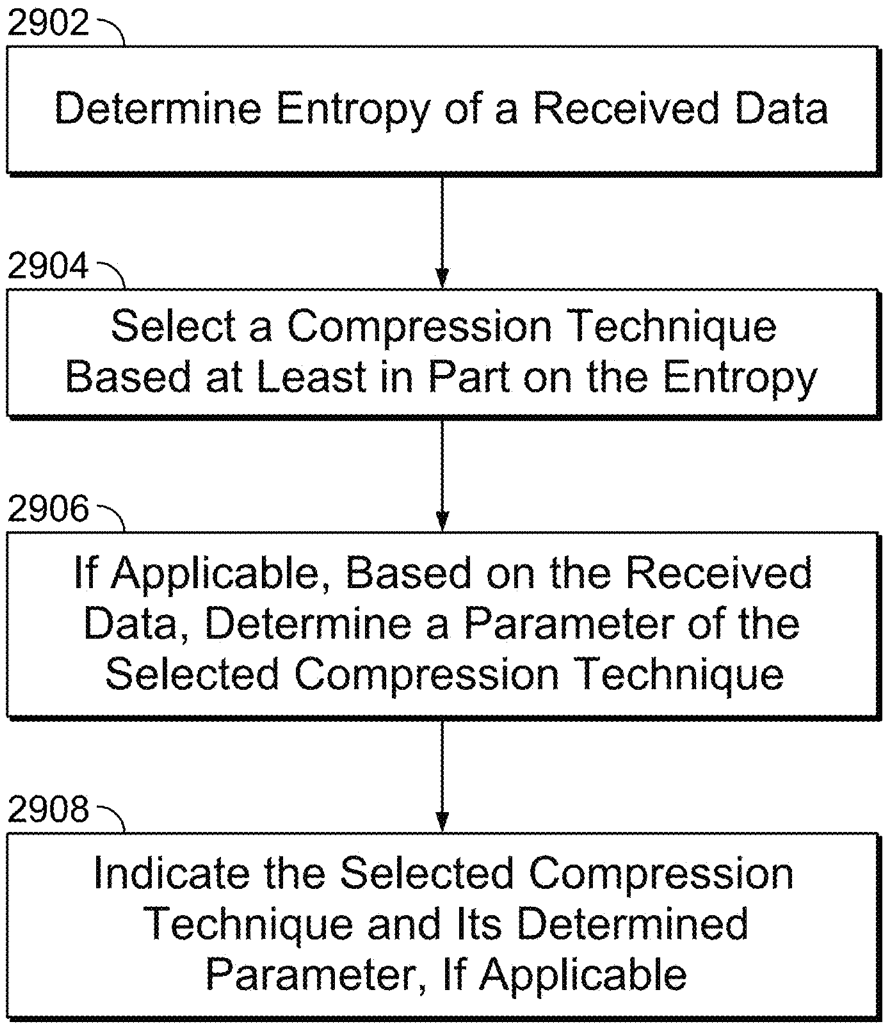
FIG. 29 is a flowchart illustrating an embodiment of a process for determining a compression technique.

FIG. 29 is a flowchart illustrating an embodiment of a process for determining a compression technique. The process of FIG. 29 may be implemented on adaptive analyzer 2512 of FIG. 25. In some embodiments, the process of FIG. 29 is included in 2806 of FIG. 28.

At 2902, entropy of a received data is determined. For example, data received in 2802 of FIG. 28 is analyzed to determine a best data compression technique among eligible techniques for the received data. In some embodiments, determining the entropy includes determining a Shannon entropy of the received data to be compressed. Determining the entropy may include determining the randomness of the data included in the received data. The entropy may indicate the compressibility of the received data and/or the type of compression technique best suited to compress the received data (e.g., technique that will most reduce the size of the data). The entropy may indicate the expected compressibility of the received data using a lossless compression technique. In some embodiments, the determining the entropy includes determining a statistical measure of lengths of same consecutive binary values (e.g., average length of consecutive zeros) in the received data.

At 2904, a compression technique is selected based at least in part on the entropy. The best type of compression technique to be utilized to compress the received data may depend on a profile and/or content of the data. For example, data with low entropy may be best compressed using a run-length encoding compression technique while data with high entropy may be best compressed using Lempel-Ziv-based compression techniques (e.g., using symbol dictionary). In some embodiments, the compression technique is selected among a plurality of possible compression techniques to most minimize the size of the compressed data. Examples of the compression technique may include any compression algorithms or data encoding/coding techniques.

At 2906, a parameter of the selected compression technique is determined based on the received data, if applicable. For example, the parameter of the compression technique is determined based on the determined entropy and/or contents of the received data. In some embodiments, one or more symbols to be included in a compression dictionary are selected based on analysis of content included the received data.

At 2908, the selected compression technique and its determined parameter (if applicable) are indicated. For example, the selected compression technique is indicated for use to compress the received data.

Figure 30:
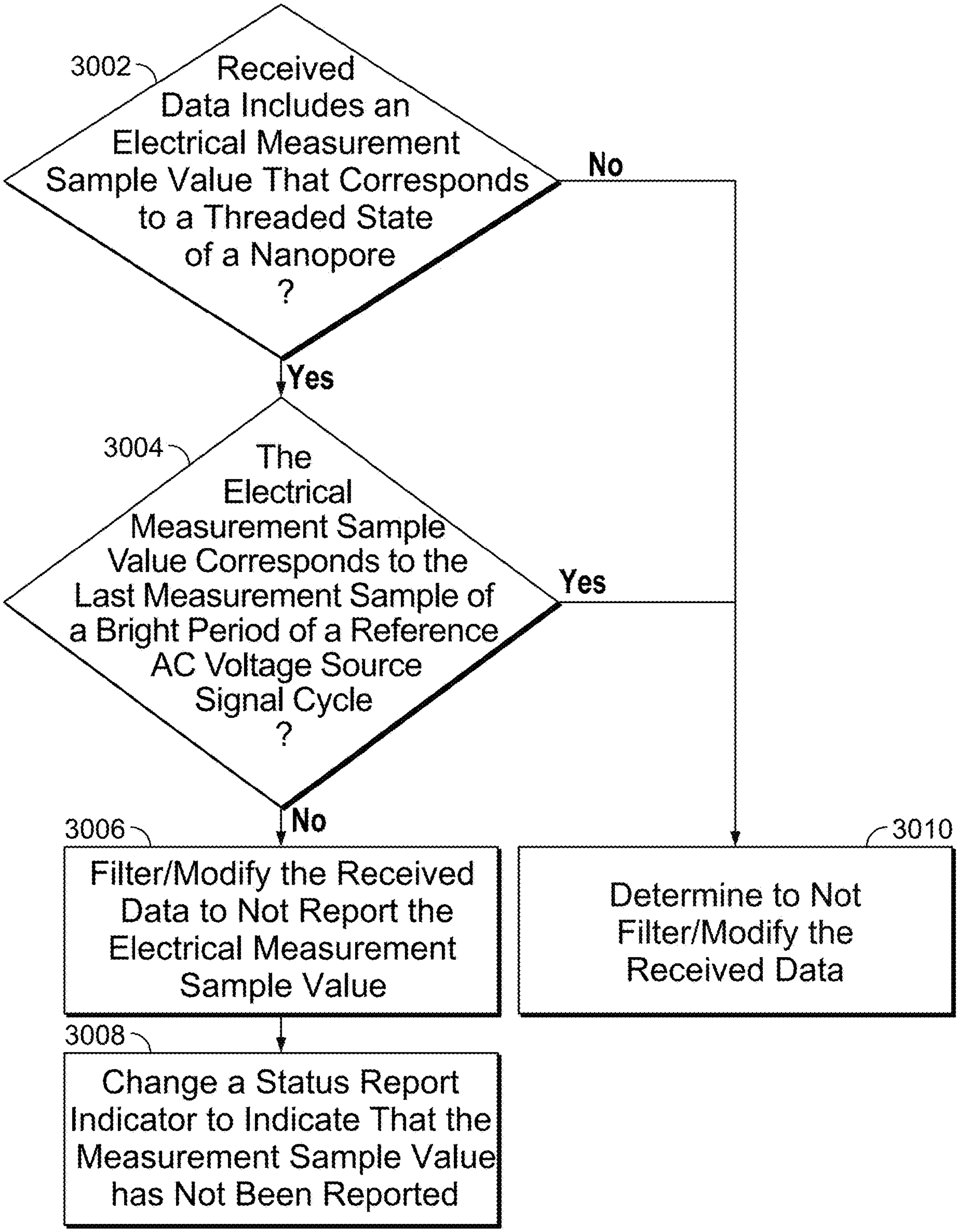
FIG. 30 is a flowchart illustrating an embodiment of a process for modifying/filtering data to be outputted.

FIG. 30 is a flowchart illustrating an embodiment of a process for modifying/filtering data to be outputted. The process of FIG. 30 may be implemented on adaptive analyzer 2512 of FIG. 25. In some embodiments, the process of FIG. 30 is included in 2810 of FIG. 28. For example, the process of FIG. 30 is executed to modify data to be outputted to reduce its size in the event a data budget would be exceeded.

At 3002, it is determined whether a received data includes an electrical measurement sample value that corresponds to a threaded state of a nanopore.

If at 3002 it is determined that the received data includes an electrical measurement sample value that corresponds to the threaded state of the nanopore, at 3004 it is determined whether the electrical measurement sample value corresponds to the last measurement sample of a bright period of a reference AC voltage source signal cycle. For example, it is determined whether reporting of a measurement sample value is able to be delayed until a next measurement sample of the nanopore because a threaded state of the nanopore will be detected/measured again.

If at 3004 it is determined that the electrical measurement sample value does not correspond to the last measurement sample, at 3006, the received data is filtered/modified to not report the electrical measurement sample value. For example, an indicator (e.g., one bit indicator) of the state of the nanopore included in the received data is modified to not indicate a state change and/or a threaded state, and/or the electrical measurement value is removed from the received data. In some embodiments, the modified received data is the version of data to be outputted from a biochip rather than outputting the original received data.

At 3008, a status report indicator (e.g., indicating whether a measurement sample value of the threaded state has been already reported for the current bright period of the current AC voltage source cycle) is changed to indicate that the measurement sample value has not been reported. This may allow a next measurement sample of the nanopore to trigger reporting of its electrical measurement value. In some embodiments, a status report indicator stored in state memory 2508 of FIG. 25 is modified.

If at 3002 it is determined that the received data does not include an electrical measurement sample value that corresponds to the threaded state of the nanopore or if at 3004 it is determined that the electrical measurement sample value does correspond to the last measurement sample, at 3010, it is determined to not filter/modify the received data. For example, at 2810 of FIG. 28, the received data is not modified if it is unable to be modified to delay reporting of an electrical measurement sample value corresponding to a threaded nanopore state.

Figure 31:
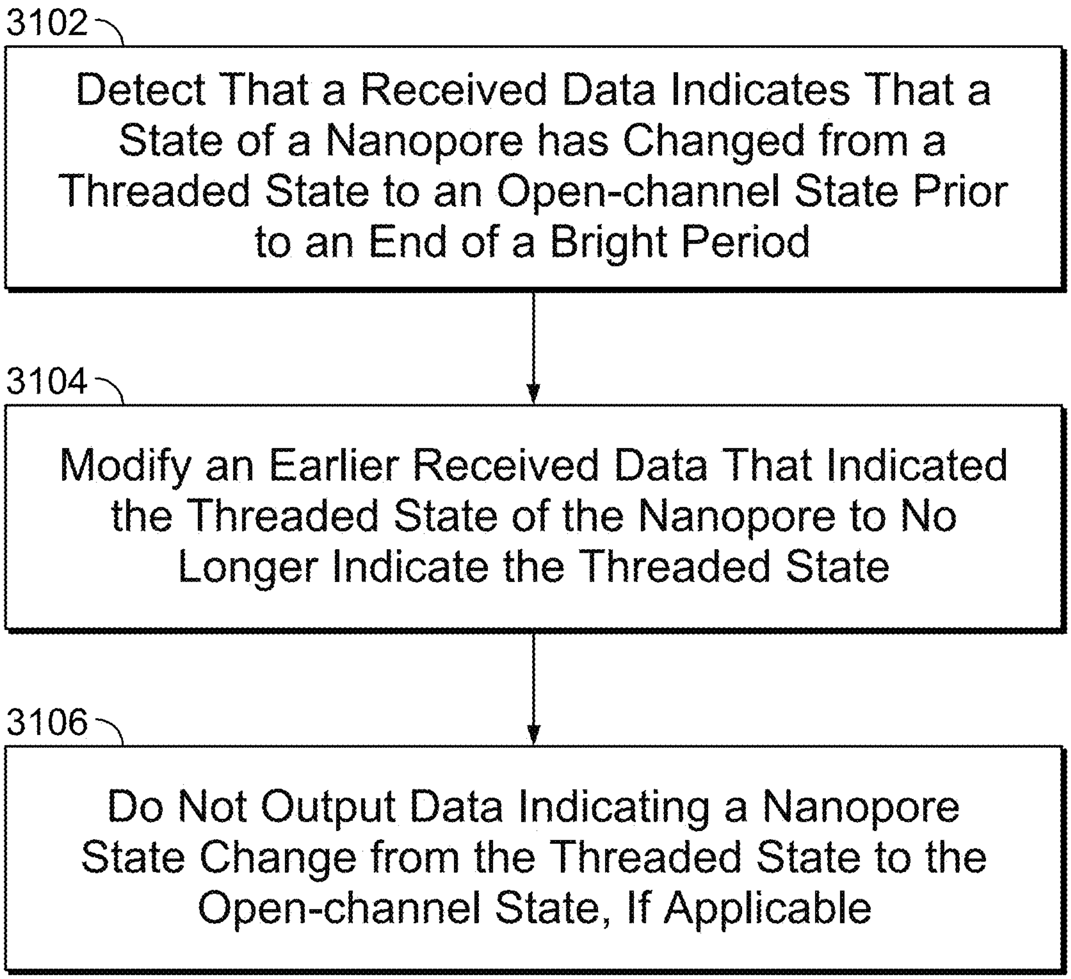
FIG. 31 is a flowchart illustrating an embodiment of a process for handling a threaded nanopore multi-state detection.

FIG. 31 is a flowchart illustrating an embodiment of a process for handling a threaded nanopore multi-state detection. The process of FIG. 31 may be implemented on adaptive analyzer 2512 of FIG. 25. In some embodiments, the process of FIG. 31 is performed after 2802 of FIG. 28. For example, the received data is processed to determine whether an earlier detected threaded state of a nanopore can be statistically deemed not representative and not reported. For example, under certain sampling conditions multiple changes of a threaded state within one bright period can be statistically deemed not representative. This may further reduce the amount of data to be outputted by a biochip. For example, rather than outputting data indicating a threaded state and then later outputting data that indicates cancelation of the threaded state detection, the nanopore state changes back and forth are not reported.

At 3102 is it detected that a received data indicates that a state of a nanopore has changed from a threaded state to an open-channel state prior to an end of a bright period. Once a tag is inserted in the nanopore during a bright period of the AC voltage cycle, the tag is expected to stay inside the nanopore until the end of the bright period and the beginning of the dark period of the AC voltage cycle under certain sampling conditions (e.g., when the electrical modulation bright/dark AC signal is fast compared to the speed of the biological events). In the event the reported state of the nanopore changes from open-channel to a threaded state and then back to the open-channel state during a single bright period prior to the end of the bright period of a cycle of an AC voltage source signal for certain sampling conditions, the earlier detected state change to the threaded state is determined to be statistically insignificant (e.g., earlier detection of the threaded state may be due to noise).

At 3104, an earlier received data that indicated the threaded state of the nanopore is modified to no longer indicate the threaded state. For example, an indication included in the received data is modified and/or a corresponding measurement value included in the earlier received data is dropped/removed. This may reduce the amount of the data to be outputted from the biochip. The earlier received data may be in the process of being analyzed using the process of FIG. 28, awaiting to be placed in an output buffer (e.g., awaiting end of bright period in the case of threaded state detection error) or included in the output buffer (e.g., in buffer 2514 of FIG. 25).

At 3106, data indicating a nanopore state change from the threaded state to the open-channel state is not outputted, if applicable. For example, because the earlier received data indicating the threaded state has been modified to not report the threaded state, the data indicating the change back to the open-channel state does not have to be outputted. For example, a state change indicator reporting the change from the threaded state to the open-channel state is modified in the received data to indicate that a state change has not been detected (e.g., indicate open-channel state has been maintained).

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system, comprising:

a circuit configured to generate a measurement value corresponding to a state of a nanopore; and a component configured to:

identify, based at least in part on a nanopore state change indicator, whether the measurement value indicates a change in the state of the nanopore, responsive to determining that the measurement value does not indicate a change in the state of the nanopore, removing the measurement value from output data to reduce a size of the output data; or responsive to determining that the measurement value indicates a change in the state of the nanopore, compressing the output data based at least in part on characteristics of the output data.

2. The system of claim 1, wherein the system is included in a biochip of a nanopore sequencing instrument.

3. The system of claim 1, wherein the measurement value is based on a difference in voltage outputs of a pair of analog storage capacitors.

4. The system of claim 3, wherein the component is further configured to reset the nanopore state change indicator responsive to determining that the difference is below a threshold.

5. The system of claim 4, wherein the measurement value is not included in the output data.

6. The system of claim 1, wherein the nanopore state change indicator is a one bit indicator.

7. The system of claim 1, wherein the change in the state of the nanopore is a change from an open-channel state to a threaded state.

8. The system of claim 1, wherein the change in the state of the nanopore is a change from a first threaded state to a second threaded state or to an open-channel state.

9. The system of claim 1, wherein compressing the output data comprises selecting a compression technique from a plurality of compression techniques based on at least one of a profile or a content of the output data.

10. The system of claim 1, wherein the plurality of compression techniques include at least one lossy compression technique and at least one lossless compression technique.

11. The system of claim 1, wherein the component is further configured to filter the output data responsive to determining that a size of the compressed output data is larger than a threshold.

12. The system of claim 11, wherein filtering the output data comprises removing the measurement value from the output data and resetting a status report identifier in a state memory to enable reporting of a subsequent measurement value for the nanopore during a current bright period of a reference AC voltage source signal.

13. The system of claim 1, wherein the component is further configured to:

determine an entropy of received data including measurement sample values from a plurality of nanopores; and select a compression technique based on the entropy.

14. The system of claim 13, wherein the selected compression technique is a run-length encoding compression technique responsive to determining the entropy is below a threshold.

15. The system of claim 13, wherein the selected compression technique is a Lempel-Ziv-based compression technique responsive to determining the entropy is above a threshold.

* * * * *